(12) United States Patent
Zagar et al.

(10) Patent No.: US 6,277,790 B1
(45) Date of Patent: Aug. 21, 2001

(54) SUBSTITUTED HERBICIDE TETRAZOLINONECARBOXYLIC ACID AMIDES

(75) Inventors: Cyrill Zagar, Ludswigshafen; Gerhard Hamprecht, Weinheim; Markus Menges, Bensheim; Olaf Menke, Altleiningen; Robert Reinhard, Ludwigshafen; Peter Schäfer, Ottersheim; Karl-Otto Westphalen, Speyer; Martina Otten, Ludwigshafen; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/463,828
(22) PCT Filed: Jul. 20, 1998
(86) PCT No.: PCT/EP98/04480
  § 371 Date: Feb. 1, 2000
  § 102(e) Date: Feb. 1, 2000
(87) PCT Pub. No.: WO99/07702
  PCT Pub. Date: Feb. 18, 1999

(30) Foreign Application Priority Data

Aug. 6, 1997 (DE) .............................. 197 33 989

(51) Int. Cl.[7] .................. A61N 43/713; C07D 257/04; C07D 261/06; C07D 401/10
(52) U.S. Cl. .................. 504/253; 504/261; 504/269; 504/271; 546/268.4; 548/245; 548/214; 548/251
(58) Field of Search .................. 548/251, 214, 548/245; 504/261, 253, 269, 271, 289, 294; 546/268.4; 549/68, 480

(56) References Cited

U.S. PATENT DOCUMENTS 4,666,502 * 5/1987 Seekinger et al. .................. 71/90
5,874,586 * 2/1999 Lantzsch et al. .................. 548/251

FOREIGN PATENT DOCUMENTS 146 279   6/1985 (EP) .
202 929   11/1986 (EP) .
612 735   8/1994 (EP) .
646 577   4/1995 (EP) .
672 663   9/1995 (EP) .
692 482   1/1996 (EP) .
695 748   2/1996 (EP) .
708 097   4/1996 (EP) .
711 761   5/1996 (EP) .
712 850   5/1996 (EP) .
728 750   8/1996 (EP) .
732 326   9/1996 (EP) .
733 624   9/1996 (EP) .
733 625   9/1996 (EP) .
98/35961  8/1998 (WO) .

* cited by examiner

Primary Examiner—Joseph K. McKane
Assistant Examiner—Sonya N. Wright
(74) Attorney, Agent, or Firm—Keil & Weinkauf

(57) ABSTRACT

Tetrazolinonecarboxamides of formula I

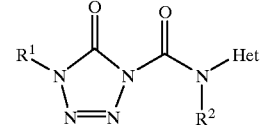

wherein
 Het is oxetan-3-yl, thietan-3-yl, tetrahydrofuran-3-yl, furan-3-yl, tetrahydrothiophen-3-yl, thiophen-3-yl, tetrahydro-2H-pyran-3-yl, tetrahydro-2H-thiopyran-3-yl, tetrahydro-2H-pyran-4-yl or tetrahydro-2H-thiopyran-4-yl, in each case with or without substitution;
 $R^1$ is optionally substituted alkyl, alkenyl, alkynyl, cycloalkyl, cycloalkenyl, phenyl, or 3- to 7-membered heterocyclyl;
 $R^2$ is hydrogen, alkyl, haloalkyl, alkenyl, haloalkenyl, alkynyl, or is optionally substituted cycloalkyl, cycloalkylalkyl, phenyl, phenylalkyl, 3- to 7-membered heterocyclyl, or 3- to 7-membered heterocyclylalkyl, their preparation and herbicidal compositions comprising them.

15 Claims, No Drawings

SUBSTITUTED HERBICIDE TETRAZOLINONECARBOXYLIC ACID AMIDES

This application is a 371 of PCT/EP98/04480 filed Jul. 20, 1998.

The present invention relates to novel substituted tetrazolinonecarboxamides of the formula I

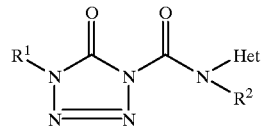

where the variables have the following meaning:

Het is oxetan-3-yl, thietan-3-yl, tetrahydrofuran-3-yl, furan-3-yl, tetrahydrothiophen-3-yl, thiophen-3-yl, tetrahydro-2H-pyran-3-yl, tetrahydro-2H-thiopyran-3-yl, tetrahydro-2H-pyran-4-yl or tetrahydro-2H-thiopyran-4-yl, where the abovementioned heterocycles may carry one or two substituents selected from a group consisting of halogen, $C_1$–$C_6$-alkyl or $C_1$–$C_6$-haloalkyl;

$R^1$ is $C_1$–$C_6$-alkyl, $C_1$–$C_6$-haloalkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_1$–$C_4$-alkylthio-C-$C_4$-alkyl, $C_1$–$C_4$-haloalkylthio-$C_1$–$C_4$-alkyl, $C_1$–$C_4$-alkylsulfonyl-$C_1$–$C_4$-alkyl, $C_1C_4$-haloalkylsulfonyl-$C_1$–$C_4$-alkyl, $C_2$–$C_6$-alkenyl, cyano-$C_3$–$C_6$-alkenyl, $C_2$–$C_6$-haloalkenyl, $C_3$–$C_6$-alkynyl, $C_3$–$C_8$-cycloalkyl, $C_3$–$C_8$-cycloalkyl-$C_1$–$C_4$-alkyl, $C_5$–$C_8$-cycloalkenyl, $C_5$–$C_8$-cycloalkenyl-$C_1$–$C_4$-alkyl, phenyl, phenyl-$C_1$–$C_4$-alkyl, 3- to 7-membered heterocyclyl, which may contain a carbonyl or thiocarbonyl ring member, or 3- to 7-membered heterocyclyl-$C_1$–$C_4$-alkyl, which may contain a carbonyl or thiocarbonyl ring member;

where the cycloalkyl rings, cycloalkenyl rings, phenyl rings or heterocyclyl rings may in each case be unsubstituted or carry one to four substituents, in each case selected from the group consisting of halogen, cyano, nitro, $C_1$–$C_4$-alkyl, $C_2$–$C_6$-alkenyl, $C_2$–$C_6$-alkynyl, $C_1$–$C_4$-haloalkyl, $C_1$–$C_4$-alkoxy, $C_1$–$C_4$-haloalkoxy, $C_3$–$C_6$-alkenyloxy, $C_3$–$C_6$-alkynyloxy, $C_1$–$C_4$-alkoxycarbonyl-$C_1$–$C_4$-alkoxy, $C_1$–$C_4$-alkylthio, $C_1$–$C_4$-haloalkylthio, $C_1$–$C_4$-alkylsulfonyl, $C_1$–$C_4$-haloalkylsulfonyl, $C_1$–$C_4$-alkoxycarbonyl, $C_1$–$C_4$-alkylcarbonyl, $C_1$–$C_4$-haloalkylcarbonyl, $C_1$–$C_4$-alkylcarbonyloxy and $C_1$–$C_4$-haloalkylcarbonyloxy; heterocyclyl- $C_1$–$C_4$-alkyl which may contain a carbonyl or thiocarbonyl ring member, the cycloalkyl rings, phenyl rings or heterocyclyl rings being with or without substitution, and herbicidal compositions comprising the tetrazolinonecarboxamides I.

$R^2$ is hydrogen, $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl, which may contain a carbonyl or thiocarbonyl ring member, or 3- to 7-membered heterocyclyl-$C_1$–$C_4$-alkyl, which may contain a carbonyl or thiocarbonyl ring member, where the cycloalkyl rings, phenyl rings or heterocyclyl rings are in each case unsubstituted or carry one to four substituents, in each case selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, $C_1$–$C_4$-alkoxycarbonyl, $C_1$–$C_4$-alkylcarbonyl, $C_1$–$C_4$-haloalkylcarbonyl, $C_1$–$C_4$-alkylcarbonyloxy and $C_1$–$C_4$-haloalkylcarbonyloxy.

Furthermore, the invention relates to processes for preparing substituted tetrazolinonecarboxamides of the formula I, to their use as herbicides, to herbicidal compositions comprising the substituted tetrazolinonecarboxamides of the formula I as active substances, to processes for preparing these herbicidal compositions and to methods for controlling undesirable vegetation.

Herbicidally active tetrazolinonecarboxamides are described, for example, in EP-A-146 279. Tetrazolinonecarboxamides which are cycloalkyl- substituted at the amide nitrogen and have herbicidal activity are disclosed, for example, in EP-A-692 482, EP-A-672 663, EP-A-612 735, EP-A-732 326, EP-A-202 929, EP-A-712 850, EP-A-711 761, EP-A-708 097, EP-A-728 750, EP-A-695 748, EP-A-733 625, EP-A-733 624.

However, the herbicidal properties of the known herbicides with respect to harmful plants are not entirely satisfactory.

It is an object of the present invention to provide novel herbicidally active compounds which allow better control of undesirable plants.

We have found that this object is achieved by the present substituted tetrazolinonecarboxamides of the formula I and their herbicidal activity.

Furthermore, we have found herbicidal compositions comprising the compounds I and having very good herbicidal activity. Furthermore, we have found processes for preparing these compositions and methods for controlling undesirable vegetation using the compounds I.

Depending on the substitution pattern, the compounds of the formula I can contain one or more chiral centers, in which case they exist in the form of enantiomer or diastereomer mixtures. This invention provides both the pure enantiomers or diastereomers and mixtures thereof.

The organic moieties mentioned for the substituents Het, $R^1$, $R^2$ or as radicals on cycloalkyl, phenyl or heterocyclyl rings are collective terms for the individual listings of the individual group members. All hydrocarbon chains, i.e. all alkyl, haloalkyl, alkoxy, haloalkoxy, alkylthio, haloalkylthio, alkylsulfonyl, haloalkylsulfonyl, cyanoalkyl, phenylalkyl, heterocyclylalkyl, alkylcarbonyl, haloalkylcarbonyl, alkylcarbonyloxy, haloalkylcarbonyloxy, alkoxycarbonyl, alkenyl, haloalkenyl, cyanoalkenyl and alkynyl groups can be straight-chain or branched. Halogenated substituents preferably carry one to five identical or different halogen atoms.

The term halogen represents in each case fluorine, chlorine, bromine or iodine, in particular fluorine or chlorine.

Examples of other meanings are:

$C_1$–$C_4$-alkyl: $CH_3$, $C_2H_5$, n-propyl, $CH(CH_3)_2$, n-butyl, 1-methylpropyl, 2-methylpropyl or $C(CH_3)_3$; in particular $CH_3$ or $C_2H_5$;

$C_1$–$C_6$-alkyl: $C_1$–$C_4$-alkyl as mentioned above, or, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; in particular $CH_3$, $C_2H_5$, n-propyl, $CH(CH_3)_2$, n-butyl, $C(CH_3)_3$, n-pentyl or n-hexyl;

$C_1$–$C_4$-haloalkyl: a $C_1$–$C_4$-alkyl radical as mentioned above which is partially or fully substituted by fluorine, chlorine, bromine and/or iodine, i.e. for example $CH_2Cl$, $CH(Cl)_2$, $C(Cl)_3$, $CH_2F$, $CHF_2$, $CF_3$, $CHFCl$, $CF(Cl)_2$, $CF_2Cl$, $CF_2Br$, 1-fluoroethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 1,2-dichloroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl; in particular chloromethyl, fluoromethyl, difluoromethyl, trifluoromethyl, 2-fluoroethyl, 2-chloroethyl, 1,2-dichloroethyl, 2,2,2-trifluoroethyl or pentafluoroethyl;

$C_1$–$C_6$-haloalkyl: $C_1$–$C_6$-alkyl as mentioned above, which is partially or fully substituted by fluorine, chlorine and/or bromine, i.e. for example one of the abovementioned $C_1$–$C_4$-haloalkyl radicals, or 5-fluoropentyl, 5-chloropentyl, 5-bromopentyl, 5-iodopentyl, 5,5,5-trichloropentyl, undecafluoropentyl, 6-fluorohexyl, 6-chlorohexyl, 6-bromohexyl, 6-iodohexyl, 6,6,6-trichlorohexyl or dodecafluorohexyl; in particular fluoromethyl, difluoromethyl, trifluoromethyl, chloromethyl, 2-fluoroethyl, 2-chloroethyl or 2,2,2-trifluoroethyl;

$C_3$–$C_8$-cycloalkyl: cyclopropyl, cyclobutyl, cyclopentyl, cyclohexyl, cycloheptyl or cyclooctyl; in particular cyclopentyl or cyclohexyl;

$C_5$–$C_8$-cycloalkenyl: cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl or cyclooct-4-enyl; in particular cyclopent-1-enyl or cyclohex-1-enyl;

$C_1$–$C_4$-alkoxy and the alkoxy radicals of alkoxycarbonylalkoxy: $OCH_3$, $OC_2H_5$, n-propoxy, $OCH(CH_3)_2$, n-butoxy, 1-methylpropoxy, 2-methylpropoxy or $OC(CH_3)_3$; in particular $OCH_3$, $OC_2H_5$, $OCH(CH_3)_2$ or $OC(CH_3)_3$;

$C_1$–$C_4$-haloalkoxy: $C_1$–$C_4$-alkoxy as mentioned above which is partially or fully substituted by fluorine, chlorine, bromine and/or iodine, i.e. for example $OCH_2Cl$, $OCH(Cl)_2$, $OC(Cl)_3$, $OCH_2F$, $OCHF_2$, $OCF_3$, $OCHFCl$, $OCF(Cl)_2$, $OCF_2Cl$, $OCF_2Br$, 1-fluoroethoxy, 2-fluoroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 1,2-dichloroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy; in particular chloromethoxy, fluoromethoxy, difluoromethoxy, trifluoromethoxy, 2-fluoroethoxy, 2-chloroethoxy, 1,2-dichloroethoxy, 2,2,2-trifluoroethoxy or pentafluoroethoxy;

$C_1$–$C_4$-alkylthio: $SCH_3$, $SC_2H_5$, n-propylthio, $SCH(CH_3)_2$, n-butylthio, 1-methylpropylthio, 2-methylpropylthio or $SC(CH_3)_3$; in particular $SCH_3$ or $SC_2H_5$;

$C_1$–$C_4$-haloalkylthio: $C_1$–$C_4$-alkylthio as mentioned above which is partially or fully substituted by fluorine, chlorine, bromine and/or iodine, i.e. for example $SCH_2Cl$, $SCH(Cl)_2$, $SC(Cl)_3$, $SCH_2F$, $SCHF_2$, $SCF_3$, $SCHFCl$, $SCF(Cl)_2$, $SCF_2Cl$, $SCF_2Br$, 1-fluoroethylthio, 2-fluoroethylthio, 2-chloroethylthio, 2-bromoethylthio, 2-iodoethylthio, 2,2-difluoroethylthio, 2,2,2-trifluoroethylthio, 1,2-dichloroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutoxy; in particular chloromethylthio, fluoromethylthio, difluoromethylthio, trifluoromethylthio, 2-fluoroethylthio, 2-chloroethylthio, 1,2-dichloroethylthio, 2,2,2-trifluoroethylthio or pentafluoroethylthio;

$C_1$–$C_4$-alkylsulfonyl: $SO_2CH_3$, $SO_2C_2H_5$, n-propylsulfonyl, $SO_2CH(CH_3)_2$, n-butylsulfonyl, 1-methylpropylsulfonyl, 2-methylpropylsulfonyl or $SO_2C(CH_3)_3$; in particular $SO_2CH_3$ or $SO_2C_2H_5$;

$C_1$–$C_4$-haloalkylsulfonyl: a $C_1$–$C_4$-alkylsulfonyl radical as mentioned above which is partially or fully substituted by fluorine, chlorine, bromine and/or iodine, i.e. for example chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 1,2-dichloroethylsulfonyl, 2,2,2-trichloroethylsulfonyl, pentafluoroethylsulfonyl, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl or nonafluorobutylsulfonyl; in particular chloromethylsulfonyl, fluoromethylsulfonyl, difluoromethylsulfonyl, trifluoromethylsulfonyl, 2-fluoroethylsulfonyl, 2-chloroethylsulfonyl, 1,2-dichloroethylsulfonyl, 2,2,2-trifluoroethylsulfonyl or pentafluoroethylsulfonyl;

cyano-$C_1$–$C_4$-alkyl: for example $CH_2CN$, 1-cyanoethyl, 2-cyanoethyl, 1-cyanoprop-1-yl, 2-cyanoprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-($CH_2CN$)eth-1-yl, 1-($CH_2CN$)-1-($CH_3$)eth-1-yl or 1-($CH_2CN$)prop-1-yl; in particular $CH_2CN$ or 2-cyanoethyl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl)eth-1-yl or 1-(phenylmethyl)prop-1-yl; in particular benzyl or 2-phenylethyl;

$C_3$–$C_8$-cycloalkyl-$C_1$–$C_4$-alkyl: cyclopropylmethyl, 1-cyclopropylethyl, 2-cyclopropylethyl, 1-cyclopropylprop-1-yl, 2-cyclopropylprop-1-yl, 3-cyclopropylprop-1-yl, 1-cyclopropylbut-1-yl, 2-cyclopropylbut-1-yl, 3-cyclopropyl-but-1-yl, 4-cyclopropylbut-1-yl, 1-cyclopropylbut-2-yl, 2-cyclopropylbut-2-yl, 3-cyclopropylbut-2-yl, 3-cyclopropyl-but-2-yl, 4-cyclopropylbut-2-yl, 1-(cyclopropylmethyl)-eth-1-yl, 1-(cyclopropylmethyl)-1-($CH_3$)-eth-1-yl, 1-(cyclopropylmethyl)prop-1-yl, cyclobutylmethyl, 1-cyclobutylethyl, 2-cyclobutylethyl, 1-cyclobutylprop-1-yl, 2-cyclobutylprop-1-yl, 3-cyclobutylprop-1-yl, 1-cyclobutylbut-1-yl, 2-cyclobutylbut-1-yl, 3-cyclobutylbut-1-yl, 4-cyclobutylbut-1-yl, 1-cyclobutylbut-2-yl, 2-cyclobutylbut-2-yl, 3-cyclobutylbut-2-yl, 3-cyclobutylbut-2-yl, 4-cyclobutylbut-2-yl, 1-(cyclobutylmethyl)eth-1-yl, 1-(cyclobutylmethyl)-1-(methyl)eth-1-yl, 1-(cyclobutylmethyl)prop-1-yl, cyclopentylmethyl, 1-cyclopentylethyl, 2-cyclopentylethyl, 1-cyclopentylprop-1-yl, 2-cyclopentylprop-1-yl, 3-cyclopentylprop-1-yl, 1-cyclopentylbut-1-yl, 2-cyclopentylbut-1-yl, 3-cyclopentylbut-1-yl, 4-cyclopentylbut-1-yl, 1-cyclopentylbut-2-yl, 2-cyclopentylbut-2-yl, 3-cyclopentylbut-2-yl, 3-cyclopentylbut-2-yl, 4-cyclopentylbut-2-yl, 1-(cyclopentylmethyl)eth-1-yl, 1-(cyclopentylmethyl)-1-(methyl)eth-1-yl, 1-(cyclopentylmethyl)prop-1-yl, cyclohexylmethyl, 1-cyclohexylethyl, 2-cyclohexylethyl, 1-cyclohexylprop-1-yl, 2-cyclohexylprop-1-yl, 3-cyclohexylprop-1-yl, 1-cyclohexylbut-1-yl, 2-cyclohexylbut-1-yl, 3-cyclohexylbut-1-yl, 4-cyclohexylbut-1-yl, 1-cyclohexylbut-2-yl, 2-cyclohexylbut-2-yl, 3-cyclohexylbut-2-yl, 3-cyclohexylbut-2-yl, 4-cyclohexylbut-2-yl, 1-(cyclohexylmethyl)eth-1-yl, 1-(cyclohexylmethyl)-1-(methyl)eth-1-yl, 1-(cyclohexylmethyl)prop-1-yl, cycloheptylmethyl, 1-cycloheptylethyl, 2-cycloheptylethyl, 1-cycloheptylprop-1-yl, 2-cycloheptylprop-1-yl, 3-cycloheptylprop-1-yl, 1-cycloheptylbut-1-yl, 2-cycloheptylbut-1-yl, 3-cycloheptylbut-1-yl, 4-cycloheptylbut-1-yl, 1-cycloheptylbut-2-yl, 2-cycloheptylbut-2-yl, 3-cycloheptylbut-2-yl, 3-cycloheptylbut-2-yl, 4-cycloheptylbut-2-yl, 1-(cycloheptylmethyl)eth-1-yl, 1-(cycloheptylmethyl)-1-(methyl)eth-1-yl, 1-(cycloheptylmethyl)prop-1-yl, cyclooctylmethyl, 1-cyclooctylethyl, 2-cyclooctylethyl, 1-cyclooctylprop-1-yl, 2-cyclooctylprop-1-yl, 3-cyclooctylprop-1-yl, 1-cyclooctylbut-1-yl, 2-cyclooctylbut-1-yl, 3-cyclooctylbut-1-yl, 4-cyclooctylbut-1-yl, 1-cyclooctylbut-2-yl, 2-cyclooctylbut-2-yl, 3-cyclooctylbut-2-yl, 3-cyclooctylbut-2-yl, 4-cyclooctylbut-2-yl, 1-(cyclooctylmethyl)eth-1-yl, 1-(cyclooctylmethyl)-1-(methyl)-eth-1-yl or 1-(cyclooctylmethyl)prop-1-yl; in particular $C_3$-$C_6$-cycloalkylmethyl;

$C_5$–$C_8$-cycloalkenyl-$C_1$–$C_4$-alkyl: (cyclopent-1-enyl)methyl, (cyclopent-2-enyl)methyl, (cyclopent-3-enyl)methyl, 1-(cyclopent-1-enyl)ethyl, 1-(cyclopent-2-enyl)ethyl, 1-(cyclopent-3-enyl)ethyl, 2-(cyclopent-1-enyl)ethyl, 2-(cyclopent-2-enyl)ethyl, 2-(cyclopent-3-enyl)ethyl, 1-(cyclopent-1-enyl)prop-1-yl, 1-(cyclopent-2-enyl)prop-1-yl, 1-(cyclopent-3-enyl)prop-1-yl, 2-(cyclopent-1-enyl)prop-1-yl, 2-(cyclopent-2-enyl)prop-1-yl, 2-(cyclopent-3-enyl)prop-1-yl, 3-(cyclopent-1-enyl)prop-1-yl, 3-(cyclopent-2-enyl)prop-1-yl, 3-(cyclopent-3-enyl)prop-1-yl, 1-(cyclopent-1-enyl)but-1-yl, 1-(cyclopent-2-enyl)but-1-yl, 1-(cyclopent-3-enyl)but-1-yl, 2-(cyclopent-1-enyl)but-1-yl, 2-(cyclopent-2-enyl)but-1-yl, 2-(cyclopent-3-enyl)but-1-yl, 3-(cyclopent-1-enyl)but-1-yl, 3-(cyclopent-2-enyl)but-1-yl, 3-(cyclopent-3-enyl)but-1-yl, 4-(cyclopent-1-enyl)but-1-yl, 4-(cyclopent-2-enyl)but-1-yl, 4-(cyclopent-3-enyl)but-1-yl, 1-(cyclopent-1-enyl)but-2-yl, 1-(cyclopent-2-enyl)but-2-yl, 1-(cyclopent-3-enyl)but-2-yl, 2-(cyclopent-1-enyl)but-2-yl, 2-(cyclopent-2-enyl)but-2-yl, 2-(cyclopent-3-enyl)but-2-yl, 3-(cyclopent-1-enyl)but-2-yl, 3-(cyclopent-2-enyl)but-2-yl, 3-(cyclopent-3-enyl)but-2-yl, 4-(cyclopent-1-enyl)but-2-yl, 4-(cyclopent-2-enyl)but-2-yl, 4-(cyclopent-3-enyl)but-2-yl, 1-((cyclopent-1-enyl)-methyl)eth-1-yl, 1-((cyclopent-2-enyl)methyl)eth-1-yl, 1-((cyclopent-3-enyl)-methyl)eth-1-yl, 1-((cyclopent-1-enyl)methyl)-1-(methyl)eth-1-yl, 1-((cyclopent-2-enyl)-methyl)-1-(methyl)eth-1-yl, 1-((cyclopent-3-enyl)-methyl)-1-(methyl)eth-1-yl, 1-((cyclopent-1-enyl)-methyl)-prop-1-yl, 1-((cyclopent-2-enyl)methyl)prop-1-yl, 1-((cyclopent-3-enyl)methyl)prop-1-yl, (cyclohex-1-enyl)methyl, (cyclohex-2-enyl)methyl, (cyclohex-3-enyl)methyl, 1-(cyclohex-1-enyl)ethyl, 1-(cyclohex-2-enyl)ethyl, 1-(cyclohex-3-enyl)ethyl, 2-(cyclohex-1-enyl)ethyl, 2-(cyclohex-2-enyl)-ethyl, 2-(cyclohex-3-enyl)ethyl, 1-(cyclohex-1-enyl)prop-1-yl, 1-(cyclohex-2-enyl)prop-1-yl, 1-(cyclohex-3-enyl)prop-1-yl, 2-(cyclohex-1-enyl)prop-1-yl, 2-(cyclohex-2-enyl)prop-1-yl, 2-(cyclohex-3-enyl)prop-1-yl, 3-(cyclohex-1-enyl)prop-1-yl, 3-(cyclohex-2-enyl)prop-1-yl, 3-(cyclohex-3-enyl)prop-1-yl, 1-(cyclohex-1-enyl)but-1-yl, 1-(cyclohex-2-enyl)but-1-yl, 1-(cyclohex-3-enyl)but-1-yl, 2-(cyclohex-1-enyl)but-1-yl, 2-(cyclohex-2-enyl)but-1-yl, 2-(cyclohex-3-enyl)but-1-yl, 3-(cyclohex-1-enyl)but-1-yl, 3-(cyclohex-2-enyl)but-1-yl, 3-(cyclohex-3-enyl)but-1-yl, 4-(cyclohex-1-enyl)but-1-yl, 4-(cyclohex-2-enyl)but-1-yl, 4-(cyclohex-3-enyl)but-1-yl, 1-(cyclohex-1-enyl)but-2-yl, 1-(cyclohex-2-enyl)but-2-yl, 1-(cyclohex-3-enyl)but-2-yl, 2-(cyclohex-1-enyl)but-2-yl, 2-(cyclohex-2-enyl)but-2-yl, 2-(cyclohex-3-enyl)but-2-yl, 3-(cyclohex-1-enyl)but-2-yl, 3-(cyclohex-2-enyl)but-2-yl, 3-(cyclohex-3-enyl)but-2-yl, 4-(cyclohex-1-enyl)but-2-yl, 4-(cyclohex-2-enyl)but-2-yl, 4-(cyclohex-3-enyl)but-2-yl 1-((cyclohex-1-enyl)methyl)eth-1-yl, 1-(cyclohex-2-enyl)methyl)eth-1-yl, 1-((cyclohex-3-enyl)methyl)eth-1-yl, 1-((cyclohex-1-enyl)methyl)-1-(methyl)eth-1-yl, 1-((cyclohex-2-enyl)methyl)-1-(methyl)eth-1-yl, 1-((cyclohex-3-enyl)methyl)-1-(methyl)eth-1-yl, 1-((cyclohex-1-enyl)methyl)prop-1-yl, 1-((cyclohex-2-enyl)methyl)prop-1-yl, 1-((cyclohex-3-enyl)methyl)prop-1-yl,(cyclohept-1-enyl)methyl, (cyclohept-2-enyl)methyl, (cyclohept-3-enyl)methyl, (cyclohept-4-enyl)methyl, 1-(cyclohept-1-enyl)ethyl, 1-(cyclohept-2-enyl)ethyl, 1-(cyclohept-3-enyl)ethyl, 1-(cyclohept-4-enyl)ethyl, 2-(cyclohept-1-enyl)ethyl, 2-(cyclohept-2-enyl)ethyl, 2-(cyclohept-3-enyl)ethyl, 2-(cyclohept-4-enyl)ethyl, 1-(cyclohept-1-enyl)prop-1-yl, 1-(cyclohept-2-enyl)prop-1-yl, 1-(cyclohept-3-enyl)prop-1-yl, 1-(cyclohept-4-enyl)prop-1-yl, 2-(cyclohept-1-enyl)prop-1-yl, 2-(cyclohept-2-enyl)prop-1-yl, 2-(cyclohept-3-enyl)prop-1-yl, 2-(cyclohept-4-enyl)prop-1-yl, 3-(cyclohept-1-enyl)prop-1-yl, 3-(cyclohept-2-enyl)prop-1-yl, 3-(cyclohept-3-enyl)prop-1-yl, 3-(cyclohept-4-enyl)prop-1-yl, 1-(cyclohept-1-enyl)but-1-yl, 1-(cyclohept-2-enyl)but-1-yl, 1-(cyclohept-3-enyl)but-1-yl, 1-(cyclohept-4-enyl)but-1-yl, 2-(cyclohept-1-enyl)but-1-yl, 2-(cyclohept-2-enyl)but-1-yl, 2-(cyclohept-3-enyl)but-1-yl, 2-(cyclohept-4-enyl)but-1-yl, 3-(cyclohept-3-enyl)but-1-yl, 3-(cyclohept-2-enyl)but-1-yl, 3-(cyclohept-3-enyl)but-1-yl, 3-(cyclohept-4-enyl)but-1-yl, 4-(cyclohept-1-enyl)but-1-yl, 4-(cyclohept-2-enyl)but-1-yl, 4-(cyclohept-3-enyl)but-1-yl, 4-(cyclohept-4-enyl)but-1-yl, 1-(cyclohept-1-enyl)but-2-yl, 1-(cyclohept-2-enyl)but-2-yl, 1-(cyclohept-3-enyl)but-2-yl, 1-(cyclohept-4-enyl)but-2-yl, 2-(cyclohept-3-enyl)but-2-yl, 2-(cyclohept-2-enyl)but-2-yl, 2-(cyclohept-3-enyl)but-2-yl, 2-(cyclohept-4-enyl)but-2-yl, 3-(cyclohept-1-enyl)but-2-yl, 3-(cyclohept-2-enyl)but-2-yl, 3-(cyclohept-3-enyl)but-2-yl, 3-(cyclohept-4-enyl)but-2-yl, 4-(cyclohept-3-enyl)but-2-yl, 4-3(cyclohept-2-enyl)but-2-yl, 4-(cyclohept-3-enyl)but-2-yl, 4-(cyclohept-4-enyl)but-2-yl, 1-((cyclohept-1-enyl)methyl)eth-1-yl, 1-((cyclohept-2-enyl)methyl)eth-1-yl, 1-((cyclohept-3-enyl)methyl)eth-1-yl, 1-((cyclohept-4-enyl)methyl)eth-1-yl, 1-((cyclohept-1-enyl)methyl)-1-(methyl)eth-1-yl, 1-((cyclohept-2-enyl)methyl)-1-(methyl)eth-1-yl, 1-((cyclohept-3-enyl)methyl)-1-(methyl)eth-1-yl, 1-((cyclohept-4-enyl)methyl)-1-(methyl)eth-1-yl, 1-((cyclohept-1-enyl)methyl)prop-1-yl, 1-((cyclohept-2-enyl)methyl)prop-1-yl, 1-((cyclohept-3-enyl)methyl)prop-1-yl, 1-((cyclohept-4-enyl)methyl)prop-1-yl, (cyclooct-1-enyl)methyl, (cyclooct-2-enyl)methyl, (cyclooct-3-enyl)methyl, (cyclooct-4-enyl)methyl, 1-(cyclooct-1-enyl)ethyl, 1-(cyclooct-2-enyl)ethyl, 1-(cyclooct-3-enyl)ethyl, 1-(cyclooct-4-enyl)ethyl, 2-(cyclooct-1-enyl)ethyl, 2-(cyclooct-2-enyl)ethyl, 2-(cyclo-oct-3-enyl)ethyl, 2-(cyclooct-4-enyl)ethyl, 1-(cyclooct-1-enyl)prop-1-yl, 1-(cyclooct-2-enyl)prop-1-yl, 1-(cyclooct-3-enyl)prop-1-yl, 1-(cyclooct-4-enyl)prop-1-yl, 2-(cyclooct-1-enyl)prop-1-yl, 2-(cyclooct-2-enyl)prop-1-yl, 2-(cyclooct-3-enyl)prop-1-yl, 2-(cyclooct-4-enyl)prop-1-yl, 3-(cyclooct-1-enyl)prop-1-yl, 3-(cyclooct-2-enyl)prop-1-yl, 3-(cyclooct-3-enyl) prop-1-yl, 3-(cyclooct-4-enyl)prop-1-yl, 1-(cyclooct-1-enyl)but-1-yl, 1-(cyclooct-2-enyl)but-1-yl, 1-(cyclooct-3-enyl)but-1-yl, 1-(cyclooct-4-enyl)but-1-yl, 2-(cyclooct-1-enyl)but-1-yl, 2-(cyclooct-2-enyl)but-1-yl, 2-(cyclooct-3-enyl)but-1-yl, 2-(cyclooct-4-enyl)but-1-yl, 3-(cyclooct-1-enyl)but-1-yl, 3-(cyclooct-2-enyl)but-1-yl, 3-(cyclooct-3-enyl)but-1-yl, 3-(cyclooct-4-enyl)but-1-yl, 4-(cyclooct-1-enyl)but-1-yl, 4-(cyclooct-2-enyl)but-1-yl, 4-(cyclooct-3-enyl)but-1-yl, 4-(cyclooct-4-enyl)but-1-yl, 1-(cyclooct-3-enyl)but-2-yl, 1-(cyclooct-2-enyl)but-2-yl, 1-(cyclooct-3-enyl)but-2-yl, 1-(cyclooct-4-enyl)but-2-yl, 2-(cyclooct-1-enyl)but-2-yl, 2-(cyclooct-2-enyl)but-2-yl, 2-(cyclooct-3-enyl)but-2-yl, 2-(cyclooct-4-enyl)but-2-yl, 3-(cyclooct-3-enyl)but-2-yl, 3-(cyclooct-2-enyl)but-2-yl, 3-(cyclooct-3-enyl)but-2-yl, 3-(cyclooct-4-enyl)but-2-yl, 4-(cyclooct-3-enyl)but-2-yl, 4-(cyclooct-2-enyl)but-2-yl, 4-(cyclooct-3-enyl)but-2-yl, 4-(cyclooct-4-enyl)but-2-yl, 1-((cyclooct-1-enyl)methyl)eth-1-yl, 1-((cyclooct-2-enyl)methyl)eth-1-yl, 1-((cyclooct-3-enyl)methyl)eth-1-yl, 1-((cyclooct-4-enyl)methyl)eth-1-yl, 1-((cyclooct-1-enyl)methyl)-1-($CH_3$)-eth-1-yl, 1-((cyclooct-2-enyl)methyl)-1-($CH_3$)eth-1-yl, 1-((cyclooct-3-enyl)methyl)-1-($CH_3$)-eth-1-yl, 1-((cyclooct-4-enyl)methyl)-1-($CH_3$)eth-1-yl, 1-((cyclooct-1-enyl)methyl)prop-1-yl, 1-((cyclooct-2-enyl)methyl)prop-1-yl, 1-((cyclooct-3-enyl)methyl) prop-1-yl, 1-((cyclooct-4-enyl)methyl)prop-1-yl; in particular $C_5$–$C_6$-cycloalkenylmethyl;

heterocyclyl-$C_1$–$C_4$-alkyl: heterocyclylmethyl, 1-(heterocyclyl)ethyl, 2-(heterocyclyl)ethyl, 1-(heterocyclyl)prop-1-yl, 2-(heterocyclyl)prop-1-yl, 3-(heterocyclyl)prop-1-yl, 1-(heterocyclyl)but-1-yl, 2-(heterocyclyl)but-1-yl, 3-(heterocyclyl)but-1-yl, 4-(heterocyclyl)but-1-yl, 1-(heterocyclyl)but-2-yl, 2-(heterocyclyl)but-2-yl, 3-(heterocyclyl)but-2-yl, 3-(heterocyclyl)but-2-yl, 4-(heterocyclyl)but-2-yl, 1-(heterocyclylmethyl)eth-1-yl, 1-(heterocyclylmethyl)-1-($CH_3$)-eth-1-yl or 1-(heterocyclylmethyl)prop-1-yl; in particular heterocyclylmethyl or 2-(heterocyclyl)ethyl, $C_1$–$C_4$-alkoxy-$C_1$–$C_4$-alkyl: $C_1$–$C_4$-alkyl which is substituted by $C_1$–$C_4$-alkoxy as mentioned above, i.e. for example $CH_2OCH_3$, $CH_2OC_2H_5$, n-propoxymethyl, (1-methylethoxy)methyl, n-butoxy-methyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-($OCH_3$)propyl, 2-($OC_2H_5$) propyl, 2-(n-propoxy)propyl, 2-(1-methylethoxy) propyl, 2-(n-butoxy)propyl, 2-(1-methylpropoxy) propyl, 2-(2-methylpropoxy)propyl, 2-(1,1-dimethylethoxy)propyl, 3-($OCH_3$)propyl, 3-($OC_2H_5$) propyl, 3-(n-propoxy)propyl, 3-(1-methylethoxy) propyl, 3-(n-butoxy)propyl, 3-(1-methylpropoxy) propyl, 3-(2-methylpropoxy)propyl, 3-(1,1-dimethylethoxy)propyl, 2-($OCH_3$)butyl, 2-($OC_2H_5$) butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-($OCH_3$)butyl, 3-($OC_2H_5$)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-($OCH_3$)butyl, 4-($OC_2H_5$)

butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl; in particular methoxymethyl or 2-methoxyethyl;

$C_1$–$C_4$-haloalkoxy-$C_1$–$C_4$-alkyl: $C_1$–$C_4$-alkyl which is substituted by $C_1$–$C_4$-haloalkoxy as mentioned above, i.e. for example 2-(difluoromethoxy)ethyl, 2-(trifluoromethoxy)ethyl or 2-(pentafluoroethoxy)ethyl;

$C_1$–$C_4$-alkylthio-$C_1$–$C_4$-alkyl: $C_1$–$C_4$-alkyl which is substituted by $C_1$–$C_4$-alkylthio as mentioned above, i.e. for example $CH_2SCH_3$, $CH_2SC_2H_5$, n-propylthiomethyl, $CH_2SCH(CH_3)_2$, n-butylthiomethyl, (1-methylpropylthio)methyl, (2-methylpropylthio)methyl, $CH_2SC(CH_3)_3$, 2-methylthioethyl, 2-ethylthioethyl, 2-(n-propylthio)ethyl, 2-(1-methylethylthio)ethyl, 2-(n-butylthio)ethyl-2-(-methylpropylthio)ethyl, 2-(2-methylpropylthio)ethyl, 2-(1,1-dimethylethylthio)ethyl, 2-($SCH_3$)propyl, 3-($SCH_3$)propyl, 2-($SC_2H_5$)propyl, 3-($SC_2H_5$)propyl, 3-(propylthio)propyl, 3-(butylthio)propyl, 4-($SCH_3$)butyl, 4-($SC_2H_5$)butyl, 4-(n-propylthio)butyl or 4-(n-butylthio)butyl; in particular $CH_2SCH_3$ or (2-methylthio)ethyl;

$C_1$–$C_4$-haloalkylthio-$C_1$–$C_4$-alkyl: $C_1$–$C_4$-alkyl which is substituted by $C_1$–$C_4$-haloalkylthio as mentioned above, i.e. for example 2-(difluoromethylthio)ethyl, 2-(trifluoromethylthio)ethyl or 2-(pentafluoroethylthio)ethyl;

$C_1$–$C_4$-alkylsulfonyl-$C_1$–$C_4$-alkyl: $C_1$–$C_4$-alkyl which is substituted by $C_1$–$C_4$-alkylsulfonyl as mentioned above, i.e. for example $CH_2SO_2CH_3$, $CH_2SO_2C_2H_5$, n-propylsulfonylmethyl, (1-methylethylsulfonyl)methyl, n-butylsulfonylmethyl, (1-methylpropylsulfonyl)methyl, (2-methylpropylsulfonyl)methyl, (1,1-dimethylethylsulfonyl)methyl, 2-methylsulfonylethyl, 2-ethylsulfonylethyl, 2-(n-propylsulfonyl)ethyl, 2-(1-methylethylsulfonyl)ethyl, 2-(n-butylsulfonyl)ethyl, 2-(1-methylpropylsulfonyl)ethyl, 2-(2-methylpropylsulfonyl)ethyl, 2-(1,1-dimethylethylsulfonyl)ethyl, 2-($SO_2CH_3$)propyl, 3-($SO_2CH_3$)propyl, 2-($SO_2C_2H_5$)propyl, 3-($SO_2C_2H_5$)propyl, 3-(propylsulfonyl)propyl, 3-(butylsulfonyl)propyl, 4-($SO_2CH_3$)butyl, 4-($SO_2C_2H_5$)butyl, 4-(n-propylsulfonyl)butyl or 4-(n-butylsulfonyl)butyl; in particular 2-($SO_2CH_3$)ethyl or 2-($SO2C_2H_5$)ethyl;

$C_1$–$C_4$-haloalkylsulfonyl-$C_1$–$C_4$-alkyl: $C_1$–$C_4$-alkyl which is substituted by $C_1$–$C_4$-haloalkylsulfonyl as mentioned above, i.e. for example 2-(2,2,2-trifluoroethylsulfonyl)ethyl;

($C_1$–$C_4$-alkyl)carbonyl: $COCH_3$, $COC_2H_5$, n-propylcarbonyl, $COCH(CH_3)_2$, n-butylcarbonyl, 1-methylpropylcarbonyl, 2-methylpropylcarbonyl or $COC(CH_3)_3$; in particular $COCH_3$, $COC_2H_5$ or $COC(CH_3)_3$;

($C_1$–$C_4$-haloalkyl)carbonyl: ($C_1$–$C_4$-alkyl)carbonyl as mentioned above which is partially or fully substituted by fluorine, chlorine, bromine and/or iodine, i.e. for example $COCH_2Cl$, $COCH(Cl)_2$, $COC(Cl)_3$, $COCH_2F$, $COCHF_2$, $COCF_3$ $COCHFCl$, $COCF(Cl)_2$, $COCF_2Cl$, $COCF_2Br$, 1-fluoroethylcarbonyl, 2-fluoroethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 1,2-dichloroethylcarbonyl, 2,2,2-trichloroethylcarbonyl, $COC_2F_5$, 3-chloropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl; in particular $COCH_2Cl$, $COCH_2F$, $COCHF_2$, $COCF_3$, 2-fluoroethylcarbonyl, 2-chloroethylcarbonyl, 1,2-dichloroethylcarbonyl, 2,2,2-trifluoroethylcarbonyl or $COC_2F_5$;

$C_1$–$C_4$-alkylcarbonyloxy: O—$COCH_3$, O—$COC_2H_5$, n-propyl-carbonyloxy, O—$COCH(CH_3)_2$, n-butylcarbonyloxy, 1-methylpropylcarbonyloxy, 2-methylpropylcarbonyloxy or O—$COC(CH_3)_3$; in particular O—$COCH_3$, O—$COC_2H_5$ or O—$COC(CH_3)_3$;

($C_1$–$C_4$-haloalkyl)carbonyloxy: ($C_1$–$C_4$-alkyl)carbonyloxy as mentioned above which is partially or fully substituted by fluorine, chlorine, bromine and/or iodine, i.e. for example O—$COCH_2Cl$, )—$COCH(Cl)_2$, O—$COC(Cl)_3$, O—$COCH_2F$, O—$COCHF_2$, O—$COCF_3$, O—$COCHFCl$, O—$COCF(Cl)_2$, O—$COCF_2Cl$, O—$COCF_2Br$, 1-fluoroethylcarbonyloxy, 2-fluoroethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 1,2-dichloroethylcarbonyloxy, 2,2,2tri-chloroethylcarbonyloxy, O—$COC_2F_5$, 3-chloropropylcarbonyloxy, heptafluoropropylcarbonyloxy, 1-(fluoromethyl)-2-fluoroethylcarbonyloxy, 1-(chloromethyl)-2-chloroethylcarbonyloxy, 1-(bromomethyl)-2-bromoethylcarbonyloxy, 4-fluorobutylcarbonyloxy, 4-chlorobutylcarbonyloxy, 4-bromobutylcarbonyloxy or nonafluorobutylcarbonyloxy; in particular O—$COCH_2Cl$, O—$COCH_2F$, O—$COCHF_2$, O—$COCF_3$, 2-fluoroethylcarbonyloxy, 2-chloroethylcarbonyloxy, 1,2-dichloroethylcarbonyloxy, 2,2,2-trifluoroethylcarbonyloxy or O—$COC_2F_5$;

($C_1$–$C_4$-alkoxy)carbonyl and the alkoxycarbonyl radicals of alkoxycarbonylalkoxy: $COOCH_3$, $COOC_2H_5$, n-propoxycarbonyl, $COOCH(CH_3)_2$, n-butoxycarbonyl, 1-(methylpropoxy)carbonyl, 2-(methylpropoxy)carbonyl or $COOC(CH_3)_3$; in particular $COOCH_3$, $COOC_2H_5$ or $COOC(CH_3)_3$;

$C_3$–$C_6$-alkenyl and the alkenyl radicals of alkenyloxy: prop-1-en-1-yl, prop-2-en-1-yl, 1-methyl- ethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1, 3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl; in particular allyl or 2-buten-1-yl;

$C_2$–$C_6$-alkenyl: $C_3$–$C_6$-alkenyl as mentioned above and ethenyl;

$C_3$–$C_6$-haloalkenyl: $C_3$–$C_6$-alkenyl as mentioned above which is partially or fully substituted by fluorine, chlorine, bromine and/or iodine, i.e. for example 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl; in particular 2-chloroallyl, 3-chloroallyl or 3,3-dichloroallyl;

$C_2$–$C_6$-haloalkenyl: $C_3$–$C_6$-haloalkenyl as mentioned above and 2-Cl-ethenyl;

cyano-$C_3$–$C_6$-alkenyl: for example 2-cyanoallyl, 3-cyanoallyl, 4-cyanobut-2-enyl, 4-cyanobut-3-enyl or 5-cyanopent-4-enyl in particular 3-cyanoallyl or 4-cyanobut-2-enyl;

$C_3$—$C_6$-alkynyl and the alkynyl radicals of alkynyloxy: prop-1-yn-1-yl, propargyl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-yn-3-yl, 3-methylbut-r-yn-4-ylg n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2 -yn-4 -yl, n-hex-2-yn-5-yl, n-hex-2-yn-6 -yl, n-hex-3-yn-1-yl, n-hex-3-yn-2 -yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl or 4-methyl-pent-2-yn-5-yl; in particular propargyl 3- to 7-membered heterocyclyl is a saturated, partially or fully unsaturated or aromatic heterocycle having one to three hetero atoms selected from a group consisting of one to three nitrogen atoms, one or two oxygen atoms and one or two sulfur atoms.

Examples of saturated heterocycles which may contain a carbonyl or thiocarbonyl ring member are: oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-4-yl, 1,3-dithiepan-5-yl, 1,3-dithiepan-6-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl;

Examples of unsaturated heterocycles which may contain a carbonyl or thiocarbonyl ring member are:

dihydrofuran-2-yl, 1,2-oxazolin-3-yl, 1,2-oxazolin-5-yl, 1,3-oxazolin-2-yl;

Preferred heteroaromatics are the 5- and 6-membered heteroaromatics, i.e. for example furyl such as 2-furyl and 3-furyl, thienyl such as 2-thienyl and 3-thienyl, pyrrolyl such as 2-pyrrolyl and 3-pyrrolyl, isoxazolyl such as 3-isoxazolyl, 4-isoxazolyl and 5-isoxazolyl, isothiazolyl such as 3-isothiazolyl, 4-isothiazolyl and 5-isothiazolyl, pyrazolyl such as 3-pyrazolyl, 4-pyrazolyl and 5-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl and 5-pyrimidinyl, furthermore 2-pyrazinyl, 1,3,5-triazin-2-yl and 1,2,4-triazin-3-yl; in particular pyridyl, pyrimidyl, furanyl and thienyl.

With a view to the use as herbicies, preference is given to those substituted tetrazolinonecarboxamides of the formula I where the variables have the following meaning, in each case either alone or in combination:

Het is tetrahydrofuran-3-yl, furan-3-yl, 2,4-dimethylfuran-3-yl, tetrahydrothiophen-3-yl, thiophen-3-yl, 2,4-dimethylthiophen-3-yl, tetra-hydro-2H-pyran-3-yl, tetrahydro-2H-thiopyran-3-yl, tetra-hydro-2H-pyran-4-yl or tetrahydro-2H-thiopyran-4-yl; particularly preferably tetrahydrofuran-3-yl, tetrahydrothiophen-3-yl, tetrahydro-2H-pyran-3-yl, tetrahydro-2H-thiopyran-3-yl, tetrahydro-2H-pyran-4-yl or tetrahydro-2H-thiopyran-4-yl;

$R^1$ is $C_1$–$C_6$-alkyl, $C_1$–$C_6$-haloalkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_1$–$C_4$-alkylthio-$C_1$–$C_4$-alkyl, $C_1$–$C_4$- haloalkylthio-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, $C_3$–$C_8$-cycloalkyl, $C_3$–$C_8$-cycloalkyl-$C_1$–$C_4$-alkyl, $C_5$–$C_8$-cycloalkenyl, $C_5$–$C_8$-cycloalkenyl-$C_1$–$C_4$-alkyl, phenyl, phenyl-$C_1$–$C_4$-alkyl, 3- to 7-membered heterocyclyl which may contain a carbonyl or thiocarbonyl ring member, or 3- to 7-membered heterocyclyl-$C_1$–$C_4$-alkyl which may contain a carbonyl or thiocarbonyl ring member, where the cycloalkyl rings, cycloalkenyl rings, phenyl rings or heterocyclyl rings may in each case be unsubstituted or may carry one to four substituents, in each case selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, $C_1$–$C_4$-alkoxycarbonyl, $C_1$–$C_4$-alkylcarbonyl, $C_1$–$C_4$-haloalkylcarbonyl, $C_1$–$C_4$-alkylcarbonyloxy and $C_1$–$C_4$-haloalkylcarbonyloxy, particularly preferably $C_1$–$C_6$-alkyl, $C_1$–$C_6$-haloalkyl, cyano-$C_1$–$C_4$-alkyl, $C_3$–$C_6$-alkenyl, $C_3$–$C_6$-haloalkenyl, $C_3$–$C_6$-alkynyl, $C_3$–$C_8$-cycloalkyl, $C_3$–$C_8$-cycloalkyl-$C_1$–$C_4$-alkyl, $C_5$–$C_8$-cycloalkenyl, $C_5$–$C_8$-cycloalkenyl-$C_1$–$C_4$-alkyl, phenyl, phenyl-$C_1$–$C_4$-alkyl, 3- to 7-membered heterocyclyl which may contain a carbonyl or thiocarbonyl ring member, or 3- to 7-membered heterocyclyl-$C_1$–$C_4$-alkyl which may contain a carbonyl or thiocarbonyl ring member, where the cycloalkyl rings, cycloalkenyl rings, phenyl rings or heterocyclyl rings are in each case unsubstituted or may carry one to four substituents, in each case selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl or $C_1$–$C_4$-alkylcarbonyl;

particularly preferably $C_1$–$C_6$-alkyl, $C_1$–$C_6$-haloalkyl, $C_2$–$C_6$-alkenyl, $C_2$–$C_6$-haloalkenyl, $C_3$–$C_8$-cycloalkyl, $C_5$–$C_8$-cycloalkenyl, phenyl, phenyl-$C_1$–$C_4$-alkyl or $C_3$–$C_7$-membered heterocyclyl which may contain a carbonyl or thiocarbonyl ring member, where the cycloalkyl rings, cycloalkenyl rings, phenyl rings or heterocyclyl rings may in each case be unsubstituted or may carry one to four substituents, in each case selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl or $C_1$–$C_4$-alkylcarbonyl;

most particularly preferably $C_1$–$C_6$-alkyl, $C_1$–$C_6$-haloalkyl, $C_3$–$C_8$-cycloalkyl, $C_5$–$C_8$-cycloalkenyl, phenyl or $C_3$–$C_7$-membered heterocyclyl which may contain a carbonyl or thiocarbonyl ring member, where the cycloalkyl rings, cycloalkenyl rings, phenyl rings or heterocyclyl rings may in each case be unsubstituted or may carry one to four substituents, in each case selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl or $C_1$–$C_4$-alkylcarbonyl;

most particularly preferably phenyl which is unsubstituted or carries one to four substituents, in each case selected from the group consisting of halogen, cyano, nitro, $C_1$–$C_4$-alkyl, $C_1$–$C_4$-halo-alkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl or $C_1$–$C_4$-alkylcarbonyl; in particular the substituents Xn listed individually in Table 1;

likewise most particularly preferred are the definitions listed individually for $R^1$ in Table 2;

$R^2$ is hydrogen, $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, phenyl or benzyl; particularly preferably $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, phenyl or benzyl;

particularly preferably the definitions listed individually for $R^2$ in Tables 1 and 2.

Very particular preference is given to the compounds Ia (=I where Het=tetrahydro-2H-pyran-4-yl and $R^1$=phenyl with or without substitution) listed in Table 1 below

TABLE 1

Ia

| No. | $X_n$ | $R^2$ |
|---|---|---|
| Ia.1 | H | $CH_3$ |
| Ia.2 | H | $C_2H_5$ |
| Ia.3 | H | n-$C_3H_7$ |
| Ia.4 | H | i-$C_3H_7$ |
| Ia.5 | H | n-$C_4H_9$ |
| Ia.6 | H | $CH_2$—CH=$CH_2$ |
| Ia.7 | H | $CH_2$—C≡CH |
| Ia.8 | H | phenyl |
| Ia.9 | H | benzyl |
| Ia.10 | 2-F | $CH_3$ |
| Ia.11 | 2-F | $C_2H_5$ |
| Ia.12 | 2-F | n-$C_3H_7$ |
| Ia.13 | 2-F | i-$C_3H_7$ |
| Ia.14 | 2-F | n-$C_4H_9$ |
| Ia.15 | 2-F | $CH_2$—CH=$CH_2$ |
| Ia.16 | 2-F | $CH_2$—C≡CH |
| Ia.17 | 2-F | phenyl |
| Ia.18 | 2-F | benzyl |
| Ia.19 | 2-Cl | $CH_3$ |
| Ia.20 | 2-Cl | $C_2H_5$ |
| Ia.21 | 2-Cl | n-$C_3H_7$ |
| Ia.22 | 2-Cl | i-$C_3H_7$ |
| Ia.23 | 2-Cl | n-$C_4H_9$ |
| Ia.24 | 2-Cl | $CH_2$—CH=$CH_2$ |
| Ia.25 | 2-Cl | $CH_2$—C≡CH |
| Ia.26 | 2-Cl | phenyl |
| Ia.27 | 2-Cl | benzyl |
| Ia.28 | 2-Br | $CH_3$ |
| Ia.29 | 2-Br | $C_2H_5$ |
| Ia.30 | 2-Br | n-$C_3H_7$ |
| Ia.31 | 2-Br | i-$C_3H_7$ |
| Ia.32 | 2-Br | n-$C_4H_9$ |
| Ia.33 | 2-Br | $CH_2$—CH=$CH_2$ |
| Ia.34 | 2-Br | $CH_2$—C≡CH |
| Ia.35 | 2-Br | phenyl |
| Ia.36 | 2-Br | benzyl |
| Ia.37 | 2-$CH_3$ | $CH_3$ |
| Ia.38 | 2-$CH_3$ | $C_2H_5$ |
| Ia.39 | 2-$CH_3$ | n-$C_3H_7$ |
| Ia.40 | 2-$CH_3$ | i-$C_3H_7$ |
| Ia.41 | 2-$CH_3$ | n-$C_4H_9$ |
| Ia.42 | 2-$CH_3$ | $CH_2$—CH=$CH_2$ |
| Ia.43 | 2-$CH_3$ | $CH_2$—C≡CH |

TABLE 1-continued

Ia

| No. | $X_n$ | $R^2$ |
|---|---|---|
| Ia.44 | 2-CH$_3$ | phenyl |
| Ia.45 | 2-CH$_3$ | benzyl |
| Ia.46 | 2-C$_2$H$_5$ | CH$_3$ |
| Ia.47 | 2-C$_2$H$_5$ | C$_2$H$_5$ |
| Ia.48 | 2-C$_2$H$_5$ | n-C$_3$H$_7$ |
| Ia.49 | 2-C$_2$H$_5$ | i-C$_3$H$_7$ |
| Ia.50 | 2-C$_2$H$_5$ | n-C$_4$H$_9$ |
| Ia.51 | 2-C$_2$H$_5$ | CH$_2$—CH=CH$_2$ |
| Ia.52 | 2-C$_2$H$_5$ | CH$_2$—C≡CH |
| Ia.53 | 2-C$_2$H$_5$ | phenyl |
| Ia.54 | 2-C$_2$H$_5$ | benzyl |
| Ia.55 | 2-OCH$_3$ | CH$_3$ |
| Ia.56 | 2-OCH$_3$ | C$_2$H$_5$ |
| Ia.57 | 2-OCH$_3$ | n-C$_3$H$_7$ |
| Ia.58 | 2-OCH$_3$ | i-C$_3$H$_7$ |
| Ia.59 | 2-OCH$_3$ | n-C$_4$H$_9$ |
| Ia.60 | 2-OCH$_3$ | CH$_2$—CH=CH$_2$ |
| Ia.61 | 2-OCH$_3$ | CH$_2$—C≡CH |
| Ia.62 | 2-OCH$_3$ | phenyl |
| Ia.63 | 2-OCH$_3$ | benzyl |
| Ia.64 | 2-OC$_2$H$_5$ | CH$_3$ |
| Ia.65 | 2-OC$_2$H$_5$ | C$_2$H$_5$ |
| Ia.66 | 2-OC$_2$H$_5$ | n-C$_3$H$_7$ |
| Ia.67 | 2-OC$_2$H$_5$ | i-C$_3$H$_7$ |
| Ia.68 | 2-OC$_2$H$_5$ | n-C$_4$H$_9$ |
| Ia.69 | 2-OC$_2$H$_5$ | CH$_2$—CH=CH$_2$ |
| Ia.70 | 2-OC$_2$H$_5$ | CH$_2$—C≡CH |
| Ia.71 | 2-OC$_2$H$_5$ | phenyl |
| Ia.72 | 2-OC$_2$H$_5$ | benzyl |
| Ia.73 | 2-SCH$_3$ | CH$_3$ |
| Ia.74 | 2-SCH$_3$ | C$_2$H$_5$ |
| Ia.75 | 2-SCH$_3$ | n-C$_3$H$_7$ |
| Ia.76 | 2-SCH$_3$ | i-C$_3$H$_7$ |
| Ia.77 | 2-SCH$_3$ | n-C$_4$H$_9$ |
| Ia.78 | 2-SCH$_3$ | CH$_2$—CH=CH$_2$ |
| Ia.79 | 2-SCH$_3$ | CH$_2$—C≡CH |
| Ia.80 | 2-SCH$_3$ | phenyl |
| Ia.81 | 2-SCH$_3$ | benzyl |
| Ia.82 | 2-OCHF$_2$ | CH$_3$ |
| Ia.83 | 2-OCHF$_2$ | C$_2$H$_5$ |
| Ia.84 | 2-OCHF$_2$ | n-C$_3$H$_7$ |
| Ia.85 | 2-OCHF$_2$ | i-C$_3$H$_7$ |
| Ia.86 | 2-OCHF$_2$ | n-C$_4$H$_9$ |
| Ia.87 | 2-OCHF$_2$ | CH$_2$—CH=CH$_2$ |
| Ia.88 | 2-OCHF$_2$ | CH$_2$—C≡CH |
| Ia.89 | 2-OCHF$_2$ | phenyl |
| Ia.90 | 2-OCHF$_2$ | benzyl |
| Ia.91 | 2-OCF$_3$ | CH$_3$ |
| Ia.92 | 2-OCF$_3$ | C$_2$H$_5$ |
| Ia.93 | 2-OCF$_3$ | n-C$_3$H$_7$ |
| Ia.94 | 2-OCF$_3$ | i-C$_3$H$_7$ |
| Ia.95 | 2-OCF$_3$ | n-C$_4$H$_9$ |
| Ia.96 | 2-OCF$_3$ | CH$_2$—CH=CH$_2$ |
| Ia.97 | 2-OCF$_3$ | CH$_2$—C≡CH |
| Ia.98 | 2-OCF$_3$ | phenyl |
| Ia.99 | 2-OCF$_3$ | benzyl |
| Ia.100 | 2-SO$_2$CH$_3$ | CH$_3$ |
| Ia.101 | 2-SO$_2$CH$_3$ | C$_2$H$_5$ |
| Ia.102 | 2-SO$_2$CH$_3$ | n-C$_3$H$_7$ |
| Ia.103 | 2-SO$_2$CH$_3$ | i-C$_3$H$_7$ |
| Ia.104 | 2-SO$_2$CH$_3$ | n-C$_4$H$_9$ |
| Ia.105 | 2-SO$_2$CH$_3$ | CH$_2$—CH=CH$_2$ |
| Ia.106 | 2-SO$_2$CH$_3$ | CH$_2$—C≡CH |
| Ia.107 | 2-SO$_2$CH$_3$ | phenyl |
| Ia.108 | 2-SO$_2$CH$_3$ | benzyl |
| Ia.109 | 3-Cl | CH$_3$ |
| Ia.110 | 3-Cl | C$_2$H$_5$ |
| Ia.111 | 3-Cl | n-C$_3$H$_7$ |
| Ia.112 | 3-Cl | i-C$_3$H$_7$ |
| Ia.113 | 3-Cl | n-C$_4$H$_9$ |
| Ia.114 | 3-Cl | CH$_2$—CH=CH$_2$ |
| Ia.115 | 3-Cl | CH$_2$—C≡CH |
| Ia.116 | 3-Cl | phenyl |
| Ia.117 | 3-Cl | benzyl |
| Ia.118 | 4-Cl | CH$_3$ |
| Ia.119 | 4-Cl | C$_2$H$_5$ |
| Ia.120 | 4-Cl | n-C$_3$H$_7$ |
| Ia.121 | 4-Cl | i-C$_3$H$_7$ |
| Ia.122 | 4-Cl | n-C$_4$H$_9$ |
| Ia.123 | 4-Cl | CH$_2$—CH=CH$_2$ |
| Ia.124 | 4-Cl | CH$_2$—C≡CH |
| Ia.125 | 4-Cl | phenyl |
| Ia.126 | 4-Cl | benzyl |
| Ia.127 | 3-CH$_3$ | CH$_3$ |
| Ia.128 | 3-CH$_3$ | C$_2$H$_5$ |
| Ia.129 | 3-CH$_3$ | n-C$_3$H$_7$ |
| Ia.130 | 3-CH$_3$ | i-C$_3$H$_7$ |
| Ia.131 | 3-CH$_3$ | n-C$_4$H$_9$ |
| Ia.132 | 3-CH$_3$ | CH$_2$—CH=CH$_2$ |
| Ia.133 | 3-CH$_3$ | CH$_2$—C≡CH |
| Ia.134 | 3-CH$_3$ | phenyl |
| Ia.135 | 3-CH$_3$ | benzyl |
| Ia.136 | 4-CH$_3$ | CH$_3$ |
| Ia.137 | 4-CH$_3$ | C$_2$H$_5$ |
| Ia.138 | 4-CH$_3$ | n-C$_3$H$_7$ |
| Ia.139 | 4-CH$_3$ | i-C$_3$H$_7$ |
| Ia.140 | 4-CH$_3$ | n-C$_4$H$_9$ |
| Ia.141 | 4-CH$_3$ | CH$_2$—CH=CH$_2$ |
| Ia.142 | 4-CH$_3$ | CH$_2$—C≡CH |
| Ia.143 | 4-CH$_3$ | phenyl |
| Ia.144 | 4-CH$_3$ | benzyl |
| Ia.145 | 2,6-F$_2$ | CH$_3$ |
| Ia.146 | 2,6-F$_2$ | C$_2$H$_5$ |
| Ia.147 | 2,6-F$_2$ | n-C$_3$H$_7$ |
| Ia.148 | 2,6-F$_2$ | i-C$_3$H$_7$ |
| Ia.149 | 2,6-F$_2$ | n-C$_4$H$_9$ |
| Ia.150 | 2,6-F$_2$ | CH$_2$—CH=CH$_2$ |
| Ia.151 | 2,6-F$_2$ | CH$_2$—C≡CH |
| Ia.152 | 2,6-F$_2$ | phenyl |
| Ia.153 | 2,6-F$_2$ | benzyl |
| Ia.154 | 2,6-Cl$_2$ | CH$_3$ |
| Ia.155 | 2,6-Cl$_2$ | C$_2$H$_5$ |
| Ia.156 | 2,6-Cl$_2$ | n-C$_3$H$_7$ |
| Ia.157 | 2,6-Cl$_2$ | i-C$_3$H$_7$ |
| Ia.158 | 2,6-Cl$_2$ | n-C$_4$H$_9$ |
| Ia.159 | 2,6-Cl$_2$ | CH$_2$—CH=CH$_2$ |
| Ia.160 | 2,6-Cl$_2$ | CH$_2$—C≡CH |
| Ia.161 | 2,6-Cl$_2$ | phenyl |
| Ia.162 | 2,6-Cl$_2$ | benzyl |
| Ia.163 | 2,6-Br$_2$ | CH$_3$ |
| Ia.164 | 2,6-Br$_2$ | C$_2$H$_5$ |
| Ia.165 | 2,6-Br$_2$ | n-C$_3$H$_7$ |
| Ia.166 | 2,6-Br$_2$ | i-C$_3$H$_7$ |
| Ia.167 | 2,6-Br$_2$ | n-C$_4$H$_9$ |
| Ia.168 | 2,6-Br$_2$ | CH$_2$—CH=CH$_2$ |
| Ia.169 | 2,6-Br$_2$ | CH$_2$—C≡CH |
| Ia.170 | 2,6-Br$_2$ | phenyl |
| Ia.171 | 2,6-Br$_2$ | benzyl |
| Ia.172 | 2,6-(CH$_3$)$_2$ | CH$_3$ |
| Ia.173 | 2,6-(CH$_3$)$_2$ | C$_2$H$_5$ |
| Ia.174 | 2,6-(CH$_3$)$_2$ | n-C$_3$H$_7$ |
| Ia.175 | 2,6-(CH$_3$)$_2$ | i-C$_3$H$_7$ |
| Ia.176 | 2,6-(CH$_3$)$_2$ | n-C$_4$H$_9$ |
| Ia.177 | 2,6-(CH$_3$)$_2$ | CH$_2$—CH=CH$_2$ |

TABLE 1-continued

| No. | $X_n$ | $R^2$ |
|---|---|---|
| Ia.178 | 2,6-(CH$_3$)$_2$ | CH$_2$—C≡CH |
| Ia.179 | 2,6-(CH$_3$)$_2$ | phenyl |
| Ia.180 | 2,6-(CH$_3$)$_2$ | benzyl |
| Ia.181 | 2-Cl, 6-Br | CH$_3$ |
| Ia.182 | 2-Cl, 6-Br | C$_2$H$_5$ |
| Ia.183 | 2-Cl, 6-Br | n-C$_3$H$_7$ |
| Ia.184 | 2-Cl, 6-Br | i-C$_3$H$_7$ |
| Ia.185 | 2-Cl, 6-Br | n-C$_4$H$_9$ |
| Ia.186 | 2-Cl, 6-Br | CH$_2$—CH=CH$_2$ |
| Ia.187 | 2-Cl, 6-Br | CH$_2$—C≡CH |
| Ia.188 | 2-Cl, 6-Br | phenyl |
| Ia.189 | 2-Cl, 6-Br | benzyl |
| Ia.190 | 2-Cl, 6-F | CH$_3$ |
| Ia.191 | 2-Cl, 6-F | C$_2$H$_5$ |
| Ia.192 | 2-Cl, 6-F | n-C$_3$H$_7$ |
| Ia.193 | 2-Cl, 6-F | i-C$_3$H$_7$ |
| Ia.194 | 2-Cl, 6-F | n-C$_4$H$_9$ |
| Ia.195 | 2-Cl, 6-F | CH$_2$—CH=CH$_2$ |
| Ia.196 | 2-Cl, 6-F | CH$_2$—C≡CH |
| Ia.197 | 2-Cl, 6-F | phenyl |
| Ia.198 | 2-Cl, 6-F | benzyl |
| Ia.199 | 2-Cl, 6-CH$_3$ | CH$_3$ |
| Ia.200 | 2-Cl, 6-CH$_3$ | C$_2$H$_5$ |
| Ia.201 | 2-Cl, 6-CH$_3$ | n-C$_3$H$_7$ |
| Ia.202 | 2-Cl, 6-CH$_3$ | i-C$_3$H$_7$ |
| Ia.203 | 2-Cl, 6-CH$_3$ | n-C$_4$H$_9$ |
| Ia.204 | 2-Cl, 6-CH$_3$ | CH$_2$—CH=CH$_2$ |
| Ia.205 | 2-Cl, 6-CH$_3$ | CH$_2$—C≡CH |
| Ia.206 | 2-Cl, 6-CH$_3$ | phenyl |
| Ia.207 | 2-Cl, 6-CH$_3$ | benzyl |
| Ia.208 | 2-Br, 6-CH$_3$ | CH$_3$ |
| Ia.209 | 2-Br, 6-CH$_3$ | C$_2$H$_5$ |
| Ia.210 | 2-Br, 6-CH$_3$ | n-C$_3$H$_7$ |
| Ia.211 | 2-Br, 6-CH$_3$ | i-C$_3$H$_7$ |
| Ia.212 | 2-Br, 6-CH$_3$ | n-C$_4$H$_9$ |
| Ia.213 | 2-Br, 6-CH$_3$ | CH$_2$—CH=CH$_2$ |
| Ia.214 | 2-Br, 6-CH$_3$ | CH$_2$—C≡CH |
| Ia.215 | 2-Br, 6-CH$_3$ | phenyl |
| Ia.216 | 2-Br, 6-CH$_3$ | benzyl |
| Ia.217 | 2-Br, 6-C$_2$H$_5$ | CH$_3$ |
| Ia.218 | 2-Br, 6-C$_2$H$_5$ | C$_2$H$_5$ |
| Ia.219 | 2-Br, 6-C$_2$H$_5$ | n-C$_3$H$_7$ |
| Ia.220 | 2-Br, 6-C$_2$H$_5$ | i-C$_3$H$_7$ |
| Ia.221 | 2-Br, 6-C$_2$H$_5$ | n-C$_4$H$_9$ |
| Ia.222 | 2-Br, 6-C$_2$H$_5$ | CH$_2$—CH=CH$_2$ |
| Ia.223 | 2-Br, 6-C$_2$H$_5$ | CH$_2$—C≡CH |
| Ia.224 | 2-Br, 6-C$_2$H$_5$ | phenyl |
| Ia.225 | 2-Br, 6-C$_2$H$_5$ | benzyl |
| Ia.226 | 3-Cl, 4-i-C$_3$H$_7$ | CH$_3$ |
| Ia.227 | 3-Cl, 4-i-C$_3$H$_7$ | C$_2$H$_5$ |
| Ia.228 | 3-Cl, 4-i-C$_3$H$_7$ | n-C$_3$H$_7$ |
| Ia.229 | 3-Cl, 4-i-C$_3$H$_7$ | i-C$_3$H$_7$ |
| Ia.230 | 3-Cl, 4-i-C$_3$H$_7$ | n-C$_4$H$_9$ |
| Ia.231 | 3-Cl, 4-i-C$_3$H$_7$ | CH$_2$—CH=CH$_2$ |
| Ia.232 | 3-Cl, 4-i-C$_3$H$_7$ | CH$_2$—C≡CH |
| Ia.233 | 3-Cl, 4-i-C$_3$H$_7$ | phenyl |
| Ia.234 | 3-Cl, 4-i-C$_3$H$_7$ | benzyl |
| Ia.235 | 3-Cl, 4-O-i-C$_3$H$_7$ | CH$_3$ |
| Ia.236 | 3-Cl, 4-O-i-C$_3$H$_7$ | C$_2$H$_5$ |
| Ia.237 | 3-Cl, 4-O-i-C$_3$H$_7$ | n-C$_3$H$_7$ |
| Ia.238 | 3-Cl, 4-O-i-C$_3$H$_7$ | i-C$_3$H$_7$ |
| Ia.239 | 3-Cl, 4-O-i-C$_3$H$_7$ | n-C$_4$H$_9$ |
| Ia.240 | 3-Cl, 4-O-i-C$_3$H$_7$ | CH$_2$—CH=CH$_2$ |
| Ia.241 | 3-Cl, 4-O-i-C$_3$H$_7$ | CH$_2$—C≡CH |
| Ia.242 | 3-Cl, 4-O-i-C$_3$H$_7$ | phenyl |
| Ia.243 | 3-Cl, 4-O-i-C$_3$H$_7$ | benzyl |
| Ia.244 | 3-Cl, 4-CH$_3$ | CH$_3$ |
| Ia.245 | 3-Cl, 4-CH$_3$ | C$_2$H$_5$ |
| Ia.246 | 3-Cl, 4-CH$_3$ | n-C$_3$H$_7$ |
| Ia.247 | 3-Cl, 4-CH$_3$ | i-C$_3$H$_7$ |
| Ia.248 | 3-Cl, 4-CH$_3$ | n-C$_4$H$_9$ |
| Ia.249 | 3-Cl, 4-CH$_3$ | CH$_2$—CH=CH$_2$ |
| Ia.250 | 3-Cl, 4-CH$_3$ | CH$_2$—C≡CH |
| Ia.251 | 3-Cl, 4-CH$_3$ | phenyl |
| Ia.252 | 3-Cl, 4-CH$_3$ | benzyl |
| Ia.253 | 3-Cl, 4-CF$_3$ | CH$_3$ |
| Ia.254 | 3-Cl, 4-CF$_3$ | C$_2$H$_5$ |
| Ia.255 | 3-Cl, 4-CF$_3$ | n-C$_3$H$_7$ |
| Ia.256 | 3-Cl, 4-CF$_3$ | i-C$_3$H$_7$ |
| Ia.257 | 3-Cl, 4-CF$_3$ | n-C$_4$H$_9$ |
| Ia.258 | 3-Cl, 4-CF$_3$ | CH$_2$—CH=CH$_2$ |
| Ia.259 | 3-Cl, 4-CF$_3$ | CH$_2$—C≡CH |
| Ia.260 | 3-Cl, 4-CF$_3$ | phenyl |
| Ia.261 | 3-Cl, 4-CF$_3$ | benzyl |
| Ia.262 | 3-Cl, 4-OCF$_3$ | CH$_3$ |
| Ia.263 | 3-Cl, 4-OCF$_3$ | C$_2$H$_5$ |
| Ia.264 | 3-Cl, 4-OCF$_3$ | n-C$_3$H$_7$ |
| Ia.265 | 3-Cl, 4-OCF$_3$ | i-C$_3$H$_7$ |
| Ia.266 | 3-Cl, 4-OCF$_3$ | n-C$_4$H$_9$ |
| Ia.267 | 3-Cl, 4-OCF$_3$ | CH$_2$—CH=CH$_2$ |
| Ia.268 | 3-Cl, 4-OCF$_3$ | CH$_2$—C≡CH |
| Ia.269 | 3-Cl, 4-OCF$_3$ | phenyl |
| Ia.270 | 3-Cl, 4-OCF$_3$ | benzyl |
| Ia.271 | 3-Cl, 4-SCF$_3$ | CH$_3$ |
| Ia.272 | 3-Cl, 4-SCF$_3$ | C$_2$H$_5$ |
| Ia.273 | 3-Cl, 4-SCF$_3$ | n-C$_3$H$_7$ |
| Ia.274 | 3-Cl, 4-SCF$_3$ | i-C$_3$H$_7$ |
| Ia.275 | 3-Cl, 4-SCF$_3$ | n-C$_4$H$_9$ |
| Ia.276 | 3-Cl, 4-SCF$_3$ | CH$_2$—CH=CH$_2$ |
| Ia.277 | 3-Cl, 4-SCF$_3$ | CH$_2$—C≡CH |
| Ia.278 | 3-Cl, 4-SCF$_3$ | phenyl |
| Ia.279 | 3-Cl, 4-SCF$_3$ | benzyl |
| Ia.280 | 3-Br, 4-CH$_3$ | CH$_3$ |
| Ia.281 | 3-Br, 4-CH$_3$ | C$_2$H$_5$ |
| Ia.282 | 3-Br, 4-CH$_3$ | n-C$_3$H$_7$ |
| Ia.283 | 3-Br, 4-CH$_3$ | i-C$_3$H$_7$ |
| Ia.284 | 3-Br, 4-CH$_3$ | n-C$_4$H$_9$ |
| Ia.285 | 3-Br, 4-CH$_3$ | CH$_2$—CH=CH$_2$ |
| Ia.286 | 3-Br, 4-CH$_3$ | CH$_2$—C≡CH |
| Ia.287 | 3-Br, 4-CH$_3$ | phenyl |
| Ia.288 | 3-Br, 4-CH$_3$ | benzyl |
| Ia.289 | 3-F, 4-CH$_3$ | CH$_3$ |
| Ia.290 | 3-F, 4-CH$_3$ | C$_2$H$_5$ |
| Ia.291 | 3-F, 4-CH$_3$ | n-C$_3$H$_7$ |
| Ia.292 | 3-F, 4-CH$_3$ | i-C$_3$H$_7$ |
| Ia.293 | 3-F, 4-CH$_3$ | n-C$_4$H$_9$ |
| Ia.294 | 3-F, 4-CH$_3$ | CH$_2$—CH=CH$_2$ |
| Ia.295 | 3-F, 4-CH$_3$ | CH$_2$—C≡CH |
| Ia.296 | 3-F, 4-CH$_3$ | phenyl |
| Ia.297 | 3-F, 4-CH$_3$ | benzyl |
| Ia.298 | 2,3-Cl$_2$ | CH$_3$ |
| Ia.299 | 2,3-Cl$_2$ | C$_2$H$_5$ |
| Ia.300 | 2,3-Cl$_2$ | n-C$_3$H$_7$ |
| Ia.301 | 2,3-Cl$_2$ | i-C$_3$H$_7$ |
| Ia.302 | 2,3-Cl$_2$ | n-C$_4$H$_9$ |
| Ia.303 | 2,3-Cl$_2$ | CH$_2$—CH=CH$_2$ |
| Ia.304 | 2,3-Cl$_2$ | CH$_2$—C≡CH |
| Ia.305 | 2,3-Cl$_2$ | phenyl |
| Ia.306 | 2,3-Cl$_2$ | benzyl |
| Ia.307 | 2,4-Cl$_2$ | CH$_3$ |
| Ia.308 | 2,4-Cl$_2$ | C$_2$H$_5$ |
| Ia.309 | 2,4-Cl$_2$ | n-C$_3$H$_7$ |
| Ia.310 | 2,4-Cl$_2$ | i-C$_3$H$_7$ |
| Ia.311 | 2,4-Cl$_2$ | n-C$_4$H$_9$ |

TABLE 1-continued

Ia

| No. | $X_n$ | $R^2$ |
|---|---|---|
| Ia.312 | 2,4-Cl$_2$ | CH$_2$—CH=CH$_2$ |
| Ia.313 | 2,4-Cl$_2$ | CH$_2$—C≡CH |
| Ia.314 | 2,4-Cl$_2$ | phenyl |
| Ia.315 | 2,4-Cl$_2$ | benzyl |
| Ia.316 | 2,5-Cl$_2$ | CH$_3$ |
| Ia.317 | 2,5-Cl$_2$ | C$_2$H$_5$ |
| Ia.318 | 2,5-Cl$_2$ | n-C$_3$H$_7$ |
| Ia.319 | 2,5-Cl$_2$ | i-C$_3$H$_7$ |
| Ia.320 | 2,5-Cl$_2$ | n-C$_4$H$_9$ |
| Ia.321 | 2,5-Cl$_2$ | CH$_2$—CH=CH$_2$ |
| Ia.322 | 2,5-Cl$_2$ | CH$_2$—C≡CH |
| Ia.323 | 2,5-Cl$_2$ | phenyl |
| Ia.324 | 2,5-Cl$_2$ | benzyl |
| Ia.325 | 2,3-(CH$_3$)$_2$ | CH$_3$ |
| Ia.326 | 2,3-(CH$_3$)$_2$ | C$_2$H$_5$ |
| Ia.327 | 2,3-(CH$_3$)$_2$ | n-C$_3$H$_7$ |
| Ia.328 | 2,3-(CH$_3$)$_2$ | i-C$_3$H$_7$ |
| Ia.329 | 2,3-(CH$_3$)$_2$ | n-C$_4$H$_9$ |
| Ia.330 | 2,3-(CH$_3$)$_2$ | CH$_2$—CH=CH$_2$ |
| Ia.331 | 2,3-(CH$_3$)$_2$ | CH$_2$—C≡CH |
| Ia.332 | 2,3-(CH$_3$)$_2$ | phenyl |
| Ia.333 | 2,3-(CH$_3$)$_2$ | benzyl |
| Ia.334 | 2,4-(CH$_3$)$_2$ | CH$_3$ |
| Ia.335 | 2,4-(CH$_3$)$_2$ | C$_2$H$_5$ |
| Ia.336 | 2,4-(CH$_3$)$_2$ | n-C$_3$H$_7$ |
| Ia.337 | 2,4-(CH$_3$)$_2$ | i-C$_3$H$_7$ |
| Ia.338 | 2,4-(CH$_3$)$_2$ | n-C$_4$H$_9$ |
| Ia.339 | 2,4-(CH$_3$)$_2$ | CH$_2$—CH=CH$_2$ |
| Ia.340 | 2,4-(CH$_3$)$_2$ | CH$_2$—C≡CH |
| Ia.341 | 2,4-(CH$_3$)$_2$ | phenyl |
| Ia.342 | 2,4-(CH$_3$)$_2$ | benzyl |
| Ia.343 | 2,5-(CH$_3$)$_2$ | CH$_3$ |
| Ia.344 | 2,5-(CH$_3$)$_2$ | C$_2$H$_5$ |
| Ia.345 | 2,5-(CH$_3$)$_2$ | n-C$_3$H$_7$ |
| Ia.346 | 2,5-(CH$_3$)$_2$ | i-C$_3$H$_7$ |
| Ia.347 | 2,5-(CH$_3$)$_2$ | n-C$_4$H$_9$ |
| Ia.348 | 2,5-(CH$_3$)$_2$ | CH$_2$—CH=CH$_2$ |
| Ia.349 | 2,5-(CH$_3$)$_2$ | CH$_2$—C≡CH |
| Ia.350 | 2,5-(CH$_3$)$_2$ | phenyl |
| Ia.351 | 2,5-(CH$_3$)$_2$ | benzyl |
| Ia.352 | 2,3-(OCH$_3$)$_2$ | CH$_3$ |
| Ia.353 | 2,3-(OCH$_3$)$_2$ | C$_2$H$_5$ |
| Ia.354 | 2,3-(OCH$_3$)$_2$ | n-C$_3$H$_7$ |
| Ia.355 | 2,3-(OCH$_3$)$_2$ | i-C$_3$H$_7$ |
| Ia.356 | 2,3-(OCH$_3$)$_2$ | n-C$_4$H$_9$ |
| Ia.357 | 2,3-(OCH$_3$)$_2$ | CH$_2$—CH=CH$_2$ |
| Ia.358 | 2,3-(OCH$_3$)$_2$ | CH$_2$—C≡CH |
| Ia.359 | 2,3-(OCH$_3$)$_2$ | phenyl |
| Ia.360 | 2,3-(OCH$_3$)$_2$ | benzyl |
| Ia.361 | 2,4-(OCH$_3$)$_2$ | CH$_3$ |
| Ia.362 | 2,4-(OCH$_3$)$_2$ | C$_2$H$_5$ |
| Ia.363 | 2,4-(OCH$_3$)$_2$ | n-C$_3$H$_7$ |
| Ia.364 | 2,4-(OCH$_3$)$_2$ | i-C$_3$H$_7$ |
| Ia.365 | 2,4-(OCH$_3$)$_2$ | n-C$_4$H$_9$ |
| Ia.366 | 2,4-(OCH$_3$)$_2$ | CH$_2$—CH=CH$_2$ |
| Ia.367 | 2,4-(OCH$_3$)$_2$ | CH$_2$—C≡CH |
| Ia.368 | 2,4-(OCH$_3$)$_2$ | phenyl |
| Ia.369 | 2,4-(OCH$_3$)$_2$ | benzyl |
| Ia.370 | 2,5-(OCH$_3$)$_2$ | CH$_3$ |
| Ia.371 | 2,5-(OCH$_3$)$_2$ | C$_2$H$_5$ |
| Ia.372 | 2,5-(OCH$_3$)$_2$ | n-C$_3$H$_7$ |
| Ia.373 | 2,5-(OCH$_3$)$_2$ | i-C$_3$H$_7$ |
| Ia.374 | 2,5-(OCH$_3$)$_2$ | n-C$_4$H$_9$ |
| Ia.375 | 2,5-(OCH$_3$)$_2$ | CH$_2$—CH=CH$_2$ |
| Ia.376 | 2,5-(OCH$_3$)$_2$ | CH$_2$—C≡CH |
| Ia.377 | 2,5-(OCH$_3$)$_2$ | phenyl |
| Ia.378 | 2,5-(OCH$_3$)$_2$ | benzyl |
| Ia.379 | 2,6-(OCH$_3$)$_2$ | CH$_3$ |
| Ia.380 | 2,6-(OCH$_3$)$_2$ | C$_2$H$_5$ |
| Ia.381 | 2,6-(OCH$_3$)$_2$ | n-C$_3$H$_7$ |
| Ia.382 | 2,6-(OCH$_3$)$_2$ | i-C$_3$H$_7$ |
| Ia.383 | 2,6-(OCH$_3$)$_2$ | n-C$_4$H$_9$ |
| Ia.384 | 2,6-(OCH$_3$)$_2$ | CH$_2$—CH=CH$_2$ |
| Ia.385 | 2,6-(OCH$_3$)$_2$ | CH$_2$—C≡CH |
| Ia.386 | 2,6-(OCH$_3$)$_2$ | phenyl |
| Ia.387 | 2,6-(OCH$_3$)$_2$ | benzyl |
| Ia.388 | 2-CF$_3$ | CH$_3$ |
| Ia.389 | 2-CF$_3$ | C$_2$H$_5$ |
| Ia.390 | 2-CF$_3$ | n-C$_3$H$_7$ |
| Ia.391 | 2-CF$_3$ | i-C$_3$H$_7$ |
| Ia.392 | 2-CF$_3$ | n-C$_4$H$_9$ |
| Ia.393 | 2-CF$_3$ | CH$_2$—CH=CH$_2$ |
| Ia.394 | 2-CF$_3$ | CH$_2$—C≡CH |
| Ia.395 | 2-CF$_3$ | phenyl |
| Ia.396 | 2-CF$_3$ | benzyl |

Furthermore, particular preference is given to the substituted tetrazolinonecarboxamides below:

The compounds Ib.1–Ib.396 which differ from the corresponding compounds Ia.1–Ia.396 only in that Het is tetrahydrofuran-3-yl:

Ib

The compounds Ic.1–Ic.396, which differ from the corresponding compounds Ia.1–Ia.396 only in that Het is furan-3-yl:

Ic

The compounds Id.1–Id.396 which differ from the corresponding compounds Ia.1–Ia.396 only in that Het is 2,4-dimethylfuran-3-yl:

Id

The compounds Ie.1–Ie.396 which differ from the corresponding compounds Ia.1–Ia.396 only in that Het is tetrahydro-2H-thio-pyran-4-yl:

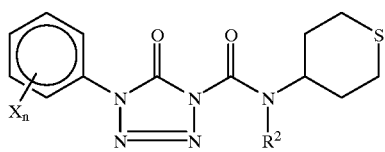

Ie

The compounds If.1–Id.396 which differ from the corresponding compounds Ia.1–Ia.396 only in that Het is tetrahydrothiophen-3-yl:

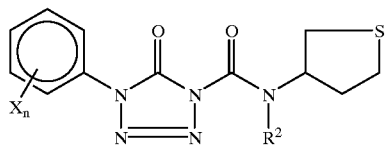

If

The compounds Ig.1–Ig.396 which differ from the corresponding compounds Ia.1–Ia.396 in that Het is thiophen-3-yl:

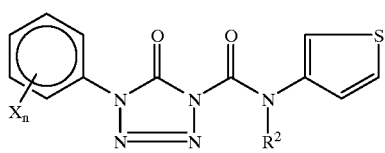

Ig

The compounds Ih.1–Ih.396 which differ from the corresponding compounds Ia.1–Ia.396 in that Het is 2,4-dimethylthiophen-3-yl:

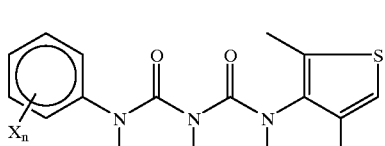

Ih

Moreover, very particular preference is given to the compounds Ii (=I where Het=tetrahydro-2H-pyran-4-yl) listed in Table 2 below:

TABLE 2

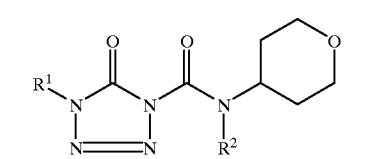

Ii

| No. | $R^1$ | $R^2$ |
|---|---|---|
| Ii.1 | $CH_3$ | $CH_3$ |
| Ii.2 | $CH_3$ | $C_2H_5$ |
| Ii.3 | $CH_3$ | n-$C_3H_7$ |
| Ii.4 | $CH_3$ | i-$C_3H_7$ |
| Ii.5 | $CH_3$ | n-$C_4H_9$ |

TABLE 2-continued

Ii

| No. | $R^1$ | $R^2$ |
|---|---|---|
| Ii.6 | $CH_3$ | $CH_2$—CH=$CH_2$ |
| Ii.7 | $CH_3$ | $CH_2$—C≡CH |
| Ii.8 | $CH_3$ | phenyl |
| Ii.9 | $CH_3$ | benzyl |
| Ii.10 | $C_2H_5$ | $CH_3$ |
| Ii.11 | $C_2H_5$ | $C_2H_5$ |
| Ii.12 | $C_2H_5$ | n-$C_3H_7$ |
| Ii.13 | $C_2H_5$ | i-$C_3H_7$ |
| Ii.14 | $C_2H_5$ | n-$C_4H_9$ |
| Ii.15 | $C_2H_5$ | $CH_2$—CH=$CH_2$ |
| Ii.16 | $C_2H_5$ | $CH_2$—C≡CH |
| Ii.17 | $C_2H_5$ | phenyl |
| Ii.18 | $C_2H_5$ | benzyl |
| Ii.19 | n-$C_3H_7$ | $CH_3$ |
| Ii.20 | n-$C_3H_7$ | $C_2H_5$ |
| Ii.21 | n-$C_3H_7$ | n-$C_3H_7$ |
| Ii.22 | n-$C_3H_7$ | i-$C_3H_7$ |
| Ii.23 | n-$C_3H_7$ | n-$C_4H_9$ |
| Ii.24 | n-$C_3H_7$ | $CH_2$—CH=$CH_2$ |
| Ii.25 | n-$C_3H_7$ | $CH_2$—C≡CH |
| Ii.26 | n-$C_3H_7$ | phenyl |
| Ii.27 | n-$C_3H_7$ | benzyl |
| Ii.28 | i-$C_3H_7$ | $CH_3$ |
| Ii.29 | i-$C_3H_7$ | $C_2H_5$ |
| Ii.30 | i-$C_3H_7$ | n-$C_3H_7$ |
| Ii.31 | i-$C_3H_7$ | i-$C_3H_7$ |
| Ii.32 | i-$C_3H_7$ | n-$C_4H_9$ |
| Ii.33 | i-$C_3H_7$ | $CH_2$—CH=$CH_2$ |
| Ii.34 | i-$C_3H_7$ | $CH_2$—C≡CH |
| Ii.35 | i-$C_3H_7$ | phenyl |
| Ii.36 | i-$C_3H_7$ | benzyl |
| Ii.37 | n-$C_4H_9$ | $CH_3$ |
| Ii.38 | n-$C_4H_9$ | $C_2H_5$ |
| Ii.39 | n-$C_4H_9$ | n-$C_3H_7$ |
| Ii.40 | n-$C_4H_9$ | i-$C_3H_7$ |
| Ii.41 | n-$C_4H_9$ | n-$C_4H_9$ |
| Ii.42 | n-$C_4H_9$ | $CH_2$—CH=$CH_2$ |
| Ii.43 | n-$C_4H_9$ | $CH_2$—C≡CH |
| Ii.44 | n-$C_4H_9$ | phenyl |
| Ii.45 | n-$C_4H_9$ | benzyl |
| Ii.46 | $CH_2$—$CH_2$—Cl | $CH_3$ |
| Ii.47 | $CH_2$—$CH_2$—Cl | $C_2H_5$ |
| Ii.48 | $CH_2$—$CH_2$—Cl | n-$C_3H_7$ |
| Ii.49 | $CH_2$—$CH_2$—Cl | i-$C_3H_7$ |
| Ii.50 | $CH_2$—$CH_2$—Cl | n-$C_4H_9$ |
| Ii.51 | $CH_2$—$CH_2$—Cl | $CH_2$—CH=$CH_2$ |
| Ii.52 | $CH_2$—$CH_2$—Cl | $CH_2$—C≡CH |
| Ii.53 | $CH_2$—$CH_2$—Cl | phenyl |
| Ii.54 | $CH_2$—$CH_2$—Cl | benzyl |
| Ii.55 | $CH_2$—$CF_3$ | $CH_3$ |
| Ii.56 | $CH_2$—$CF_3$ | $C_2H_5$ |
| Ii.57 | $CH_2$—$CF_3$ | n-$C_3H_7$ |
| Ii.58 | $CH_2$—$CF_3$ | i-$C_3H_7$ |
| Ii.59 | $CH_2$—$CF_3$ | n-$C_4H_9$ |
| Ii.60 | $CH_2$—$CF_3$ | $CH_2$—CH=$CH_2$ |
| Ii.61 | $CH_2$—$CF_3$ | $CH_2$—C≡CH |
| Ii.62 | $CH_2$—$CF_3$ | phenyl |
| Ii.63 | $CH_2$—$CF_3$ | benzyl |
| Ii.64 | CH=$CH_2$ | $CH_3$ |
| Ii.65 | CH=$CH_2$ | $C_2H_5$ |
| Ii.78 | $CH_2$—CH=$CH_2$ | $CH_2$—CH=$CH_2$ |
| Ii.79 | $CH_2$—CH=$CH_2$ | $CH_2$—C≡CH |
| Ii.80 | $CH_2$—CH=$CH_2$ | phenyl |
| Ii.81 | $CH_2$—CH=$CH_2$ | benzyl |
| Ii.82 | CH=CH—$CH_3$ | $CH_3$ |
| Ii.83 | CH=CH—$CH_3$ | $C_2H_5$ |

TABLE 2-continued

Ii structure: R¹ attached to N of a tetrazolinone-carboxamide with N-R² and tetrahydropyran-4-yl group

| No. | R¹ | R² |
|---|---|---|
| Ii.84 | CH=CH—CH₃ | n-C₃H₇ |
| Ii.85 | CH=CH—CH₃ | i-C₃H₇ |
| Ii.86 | CH=CH—CH₃ | n-C₄H₉ |
| Ii.87 | CH=CH—CH₃ | CH₂—CH=CH₂ |
| Ii.88 | CH=CH—CH₃ | CH₂—C≡CH |
| Ii.89 | CH=CH—CH₃ | phenyl |
| Ii.90 | CH=CH—CH₃ | benzyl |
| Ii.91 | CH=CH—Cl | CH₃ |
| Ii.92 | CH=CH—Cl | C₂H₅ |
| Ii.93 | CH=CH—Cl | n-C₃H₇ |
| Ii.94 | CH=CH—Cl | i-C₃H₇ |
| Ii.95 | CH=CH—Cl | n-C₄H₉ |
| Ii.96 | CH=CH—Cl | CH₂—CH=CH₂ |
| Ii.97 | CH=CH—Cl | CH₂—C≡CH |
| Ii.98 | CH=CH—Cl | |
| Ii.112 | 1-methylcyclopropyl | i-C₃H₇ |
| Ii.113 | 1-methylcyclopropyl | n-C₄H₉ |
| Ii.114 | 1-methylcyclopropyl | CH₂—CH=CH₂ |
| Ii.115 | 1-methylcyclopropyl | CH₂—C≡CH |
| Ii.116 | 1-methylcyclopropyl | phenyl |
| Ii.117 | 1-methylcyclopropyl | benzyl |
| Ii.118 | 2-methylcyclopropyl | CH₃ |
| Ii.119 | 2-methylcyclopropyl | C₂H₅ |
| Ii.120 | 2-methylcyclopropyl | n-C₃H₇ |
| Ii.121 | 2-methylcyclopropyl | i-C₃H₇ |
| Ii.122 | 2-methylcyclopropyl | n-C₄H₉ |
| Ii.123 | 2-methylcyclopropyl | CH₂—CH=CH₂ |
| Ii.124 | 2-methylcyclopropyl | CH₂—C≡CH |
| Ii.125 | 2-methylcyclopropyl | phenyl |
| Ii.126 | 2-methylcyclopropyl | benzyl |
| Ii.127 | 2,2-dichlorocyclopropyl | CH₃ |
| Ii.128 | 2,2-dichlorocyclopropyl | C₂H₅ |
| Ii.129 | 2,2-dichlorocyclopropyl | n-C₃H₇ |
| Ii.130 | 2,2-dichlorocyclopropyl | i-C₃H₇ |
| Ii.131 | 2,2-dichlorocyclopropyl | n-C₄H₉ |
| Ii.132 | 2,2-dichlorocyclopropyl | CH₂—CH=CH₂ |
| Ii.133 | 2,2-dichlorocyclopropyl | CH₂—C≡CH |
| Ii.134 | 2,2-dichlorocyclopropyl | phenyl |
| Ii.135 | 2,2-dichlorocyclopropyl | benzyl |
| Ii.136 | 2,2-difluorocyclopropyl | CH₃ |
| Ii.137 | 2,2-difluorocyclopropyl | C₂H₅ |
| Ii.138 | 2,2-difluorocyclopropyl | n-C₃H₇ |
| Ii.139 | 2,2-difluorocyclopropyl | i-C₃H₇ |
| Ii.140 | 2,2-difluorocyclopropyl | n-C₄H₉ |
| Ii.141 | 2,2-difluorocyclopropyl | CH₂—CH=CH₂ |
| Ii.142 | 2,2-difluorocyclopropyl | CH₂—C≡CH |
| Ii.143 | 2,2-difluorocyclopropyl | phenyl |
| Ii.144 | 2,2-difluorocyclopropyl | benzyl |
| Ii.145 | 2,2-difluoro-1-methylcyclopropyl | CH₃ |
| Ii.146 | 2,2-difluoro-1-methylcyclopropyl | C₂H₅ |
| Ii.147 | 2,2-difluoro-1-methylcyclopropyl | n-C₃H₇ |
| Ii.148 | 2,2-difluoro-1-methylcyclopropyl | i-C₃H₇ |
| Ii.149 | 2,2-difluoro-1-methylcyclopropyl | n-C₄H₉ |
| Ii.150 | 2,2-difluoro-1-methylcyclopropyl | CH₂—CH=CH₂ |
| Ii.151 | 2,2-difluoro-1-methylcyclopropyl | CH₂—C≡CH |
| Ii.152 | 2,2-difluoro-1-methylcyclopropyl | phenyl |
| Ii.153 | 2,2-difluoro-1-methylcyclopropyl | benzyl |
| Ii.154 | 2,2-dichloro-1-methylcyclopropyl | CH₃ |
| Ii.155 | 2,2-dichloro-1-methylcyclopropyl | C₂H₅ |
| Ii.156 | 2,2-dichloro-1-methylcyclopropyl | n-C₃H₇ |
| Ii.157 | 2,2-dichloro-1-methylcyclopropyl | i-C₃H₇ |
| Ii.158 | 2,2-dichloro-1-methylcyclopropyl | n-C₄H₉ |
| Ii.159 | 2,2-dichloro-1-methylcyclopropyl | CH₂—CH=CH₂ |
| Ii.160 | 2,2-dichloro-1-methylcyclopropyl | CH₂—C≡CH |
| Ii.161 | 2,2-dichloro-1-methylcyclopropyl | phenyl |
| Ii.162 | 2,2-dichloro-1-methylcyclopropyl | benzyl |
| Ii.163 | cyclobutyl | CH₃ |
| Ii.164 | cyclobutyl | C₂H₅ |
| Ii.165 | cyclobutyl | n-C₃H₇ |
| Ii.166 | cyclobutyl | i-C₃H₇ |
| Ii.167 | cyclobutyl | n-C₄H₉ |
| Ii.168 | cyclobutyl | CH₂—CH=CH₂ |
| Ii.169 | cyclobutyl | CH₂—C≡CH |
| Ii.170 | cyclobutyl | phenyl |
| Ii.171 | cyclobutyl | benzyl |
| Ii.172 | 1-methylcyclobutyl | CH₃ |
| Ii.173 | 1-methylcyclobutyl | C₂H₅ |
| Ii.174 | 1-methylcyclobutyl | n-C₃H₇ |
| Ii.175 | 1-methylcyclobutyl | i-C₃H₇ |
| Ii.176 | 1-methylcyclobutyl | n-C₄H₉ |
| Ii.177 | 1-methylcyclobutyl | CH₂—CH=CH₂ |
| Ii.178 | 1-methylcyclobutyl | CH₂—C≡CH |
| Ii.179 | 1-methylcyclobutyl | phenyl |
| Ii.180 | 1-methylcyclobutyl | benzyl |
| Ii.181 | cyclopentyl | CH₃ |
| Ii.182 | cyclopentyl | C₂H₅ |
| Ii.183 | cyclopentyl | n-C₃H₇ |
| Ii.184 | cyclopentyl | i-C₃H₇ |
| Ii.185 | cyclopentyl | n-C₄H₉ |
| Ii.186 | cyclopentyl | CH₂—CH=CH₂ |
| Ii.187 | cyclopentyl | CH₂—C≡CH |
| Ii.188 | cyclopentyl | phenyl |
| Ii.189 | cyclopentyl | benzyl |
| Ii.190 | 1-methylcyclopentyl | CH₃ |
| Ii.191 | 1-methylcyclopentyl | C₂H₅ |
| Ii.192 | 1-methylcyclopentyl | n-C₃H₇ |
| Ii.193 | 1-methylcyclopentyl | i-C₃H₇ |
| Ii.194 | 1-methylcyclopentyl | n-C₄H₉ |
| Ii.195 | 1-methylcyclopentyl | CH₂—CH=CH₂ |
| Ii.196 | 1-methylcyclopentyl | CH₂—C≡CH |
| Ii.197 | 1-methylcyclopentyl | phenyl |
| Ii.198 | 1-methylcyclopentyl | benzyl |
| Ii.199 | cyclohexyl | CH₃ |
| Ii.200 | cyclohexyl | C₂H₅ |
| Ii.201 | cyclohexyl | n-C₃H₇ |
| Ii.202 | cyclohexyl | i-C₃H₇ |
| Ii.203 | cyclohexyl | n-C₄H₉ |
| Ii.204 | cyclohexyl | CH₂—CH=CH₂ |
| Ii.205 | cyclohexyl | CH₂—C≡CH |
| Ii.206 | cyclohexyl | phenyl |
| Ii.207 | cyclohexyl | benzyl |
| Ii.208 | 1-methylcyclohexyl | CH₃ |
| Ii.209 | 1-methylcyclohexyl | C₂H₅ |
| Ii.210 | 1-methylcyclohexyl | n-C₃H₇ |
| Ii.211 | 1-methylcyclohexyl | i-C₃H₇ |
| Ii.212 | 1-methylcyclohexyl | n-C₄H₉ |
| Ii.213 | 1-methylcyclohexyl | CH₂—CH=CH₂ |
| Ii.214 | 1-methylcyclohexyl | CH₂—C≡CH |
| Ii.215 | 1-methylcyclohexyl | phenyl |
| Ii.216 | 1-methylcyclohexyl | benzyl |
| Ii.217 | 2-methylcyclohexyl | CH₃ |
| Ii.218 | 2-methylcyclohexyl | C₂H₅ |
| Ii.219 | 2-methylcyclohexyl | n-C₃H₇ |
| Ii.220 | 2-methylcyclohexyl | i-C₃H₇ |
| Ii.221 | 2-methylcyclohexyl | n-C₄H₉ |
| Ii.222 | 2-methylcyclohexyl | CH₂—CH=CH₂ |
| Ii.223 | 2-methylcyclohexyl | CH₂—C≡CH |
| Ii.224 | 2-methylcyclohexyl | phenyl |
| Ii.225 | 2-methylcyclohexyl | benzyl |
| Ii.226 | 3-methylcyclohexyl | CH₃ |
| Ii.227 | 3-methylcyclohexyl | C₂H₅ |
| Ii.228 | 3-methylcyclohexyl | n-C₃H₇ |
| Ii.229 | 3-methylcyclohexyl | i-C₃H₇ |
| Ii.230 | 3-methylcyclohexyl | n-C₄H₉ |

TABLE 2-continued

Ii

| No. | R¹ | R² |
|---|---|---|
| Ii.231 | 3-methylcyclohexyl | $CH_2-CH=CH_2$ |
| Ii.232 | 3-methylcyclohexyl | $CH_2-C\equiv CH$ |
| Ii.233 | 3-methylcyclohexyl | phenyl |
| Ii.234 | 3-methylcyclohexyl | benzyl |
| Ii.235 | 4-methylcyclohexyl | $CH_3$ |
| Ii.236 | 4-methylcyclohexyl | $C_2H_5$ |
| Ii.237 | 4-methylcyclohexyl | $n-C_3H_7$ |
| Ii.238 | 4-methylcyclohexyl | $i-C_3H_7$ |
| Ii.239 | 4-methylcyclohexyl | $n-C_4H_9$ |
| Ii.240 | 4-methylcyclohexyl | $CH_2-CH=CH_2$ |
| Ii.241 | 4-methylcyclohexyl | $CH_2-C\equiv CH$ |
| Ii.242 | 4-methylcyclohexyl | phenyl |
| Ii.243 | 4-methylcyclohexyl | benzyl |
| Ii.244 | 2,3-dimethylcyclohexyl | $CH_3$ |
| Ii.245 | 2,3-dimethylcyclohexyl | $C_2H_5$ |
| Ii.246 | 2,3-dimethylcyclohexyl | $n-C_3H_7$ |
| Ii.247 | 2,3-dimethylcyclohexyl | $i-C_3H_7$ |
| Ii.248 | 2,3-dimethylcyclohexyl | $n-C_4H_9$ |
| Ii.249 | 2,3-dimethylcyclohexyl | $CH_2-CH=CH_2$ |
| Ii.250 | 2,3-dimethylcyclohexyl | $CH_2-C\equiv CH$ |
| Ii.251 | 2,3-dimethylcyclohexyl | phenyl |
| Ii.252 | 2,3-dimethylcyclohexyl | benzyl |
| Ii.253 | 2,6-dimethylcyclohexyl | $CH_3$ |
| Ii.254 | 2,6-dimethylcyclohexyl | $C_2H_5$ |
| Ii.255 | 2,6-dimethylcyclohexyl | $n-C_3H_7$ |
| Ii.256 | 2,6-dimethylcyclohexyl | $i-C_3H_7$ |
| Ii.257 | 2,6-dimethylcyclohexyl | $n-C_4H_9$ |
| Ii.258 | 2,6-dimethylcyclohexyl | $CH_2-CH=CH_2$ |
| Ii.259 | 2,6-dimethylcyclohexyl | $CH_2-C\equiv CH$ |
| Ii.260 | 2,6-dimethylcyclohexyl | phenyl |
| Ii.261 | 2,6-dimethylcyclohexyl | benzyl |
| Ii.262 | 1-cyclopentenyl | $CH_3$ |
| Ii.263 | 1-cyclopentenyl | $C_2H_5$ |
| Ii.264 | 1-cyclopentenyl | $n-C_3H_7$ |
| Ii.265 | 1-cyclopentenyl | $i-C_3H_7$ |
| Ii.266 | 1-cyclopentenyl | $n-C_4H_9$ |
| Ii.267 | 1-cyclopentenyl | $CH_2-CH=CH_2$ |
| Ii.268 | 1-cyclopentenyl | $CH_2-C\equiv CH$ |
| Ii.269 | 1-cyclopentenyl | phenyl |
| Ii.270 | 1-cyclopentenyl | benzyl |
| Ii.271 | 2-chloro-1-cyclopentenyl | $CH_3$ |
| Ii.272 | 2-chloro-1-cyclopentenyl | $C_2H_5$ |
| Ii.273 | 2-chloro-1-cyclopentenyl | $n-C_3H_7$ |
| Ii.274 | 2-chloro-1-cyclopentenyl | $i-C_3H_7$ |
| Ii.275 | 2-chloro-1-cyclopentenyl | $n-C_4H_9$ |
| Ii.276 | 2-chloro-1-cyclopentenyl | $CH_2-CH=CH_2$ |
| Ii.277 | 2-chloro-1-cyclopentenyl | $CH_2-C\equiv CH$ |
| Ii.278 | 2-chloro-1-cyclopentenyl | phenyl |
| Ii.279 | 2-chloro-1-cyclopentenyl | benzyl |
| Ii.280 | 1-cyclohexenyl | $CH_3$ |
| Ii.281 | 1-cyclohexenyl | $C_2H_5$ |
| Ii.282 | 1-cyclohexenyl | $n-C_3H_7$ |
| Ii.283 | 1-cyclohexenyl | $i-C_3H_7$ |
| Ii.284 | 1-cyclohexenyl | $n-C_4H_9$ |
| Ii.285 | 1-cyclohexenyl | $CH_2-CH=CH_2$ |
| Ii.286 | 1-cyclohexenyl | $CH_2-C\equiv CH$ |
| Ii.287 | 1-cyclohexenyl | phenyl |
| Ii.288 | 1-cyclohexenyl | benzyl |
| Ii.289 | 2-chloro-1-cyclohexenyl | $CH_3$ |
| Ii.290 | 2-chloro-1-cyclohexenyl | $C_2H_5$ |
| Ii.291 | 2-chloro-1-cyclohexenyl | $n-C_3H_7$ |
| Ii.292 | 2-chloro-1-cyclohexenyl | $i-C_3H_7$ |
| Ii.293 | 2-chloro-1-cyclohexenyl | $n-C_4H_9$ |
| Ii.294 | 2-chloro-1-cyclohexenyl | $CH_2-CH=CH_2$ |
| Ii.295 | 2-chloro-1-cyclohexenyl | $CH_2-C\equiv CH$ |
| Ii.296 | 2-chloro-1-cyclohexenyl | phenyl |
| Ii.297 | 2-chloro-1-cyclohexenyl | benzyl |
| Ii.298 | benzyl | $CH_3$ |
| Ii.299 | benzyl | $C_2H_5$ |
| Ii.300 | benzyl | $n-C_3H_7$ |
| Ii.301 | benzyl | $i-C_3H_7$ |
| Ii.302 | benzyl | $n-C_4H_9$ |
| Ii.303 | benzyl | $CH_2-CH=CH_2$ |
| Ii.304 | benzyl | $CH_2-C\equiv CH$ |
| Ii.305 | benzyl | phenyl |
| Ii.306 | benzyl | benzyl |
| Ii.307 | 2-chlorobenzyl | $CH_3$ |
| Ii.308 | 2-chlorobenzyl | $C_2H_5$ |
| Ii.309 | 2-chlorobenzyl | $n-C_3H_7$ |
| Ii.310 | 2-chlorobenzyl | $i-C_3H_7$ |
| Ii.311 | 2-chlorobenzyl | $n-C_4H_9$ |
| Ii.312 | 2-chlorobenzyl | $CH_2-CH=CH_2$ |
| Ii.313 | 2-chlorobenzyl | $CH_2-C\equiv CH$ |
| Ii.314 | 2-chlorobenzyl | phenyl |
| Ii.315 | 2-chlorobenzyl | benzyl |
| Ii.316 | 2-methylbenzyl | $CH_3$ |
| Ii.317 | 2-methylbenzyl | $C_2H_5$ |
| Ii.318 | 2-methylbenzyl | $n-C_3H_7$ |
| Ii.319 | 2-methylbenzyl | $i-C_3H_7$ |
| Ii.320 | 2-methylbenzyl | $n-C_4H_9$ |
| Ii.321 | 2-methylbenzyl | $CH_2-CH=CH_2$ |
| Ii.322 | 2-methylbenzyl | $CH_2-C\equiv CH$ |
| Ii.323 | 2-methylbenzyl | phenyl |
| Ii.324 | 2-methylbenzyl | benzyl |
| Ii.325 | 2,6-dimethylbenzyl | $CH_3$ |
| Ii.326 | 2,6-dimethylbenzyl | $C_2H_5$ |
| Ii.327 | 2,6-dimethylbenzyl | $n-C_3H_7$ |
| Ii.328 | 2,6-dimethylbenzyl | $i-C_3H_7$ |
| Ii.329 | 2,6-dimethylbenzyl | $n-C_4H_9$ |
| Ii.330 | 2,6-dimethylbenzyl | $CH_2-CH=CH_2$ |
| Ii.331 | 2,6-dimethylbenzyl | $CH_2-C\equiv CH$ |
| Ii.332 | 2,6-dimethylbenzyl | phenyl |
| Ii.333 | 2,6-dimethylbenzyl | benzyl |
| Ii.334 | 2,6-dichlorobenzyl | $CH_3$ |
| Ii.335 | 2,6-dichlorobenzyl | $C_2H_5$ |
| Ii.336 | 2,6-dichlorobenzyl | $n-C_3H_7$ |
| Ii.337 | 2,6-dichlorobenzyl | $i-C_3H_7$ |
| Ii.338 | 2,6-dichlorobenzyl | $n-C_4H_9$ |
| Ii.339 | 2,6-dichlorobenzyl | $CH_2-CH=CH_2$ |
| Ii.340 | 2,6-dichlorobenzyl | $CH_2-C\equiv CH$ |
| Ii.341 | 2,6-dichlorobenzyl | phenyl |
| Ii.342 | 2,6-dichlorobenzyl | benzyl |
| Ii.343 | 2-methyl-3-furyl | $CH_3$ |
| Ii.344 | 2-methyl-3-furyl | $C_2H_5$ |
| Ii.345 | 2-methyl-3-furyl | $n-C_3H_7$ |
| Ii.346 | 2-methyl-3-furyl | $i-C_3H_7$ |
| Ii.347 | 2-methyl-3-furyl | $n-C_4H_9$ |
| Ii.348 | 2-methyl-3-furyl | $CH_2-CH=CH_2$ |
| Ii.349 | 2-methyl-3-furyl | $CH_2-C\equiv CH$ |
| Ii.350 | 2-methyl-3-furyl | phenyl |
| Ii.351 | 2-methyl-3-furyl | benzyl |
| Ii.352 | 2,4-dimethyl-3-furyl | $CH_3$ |
| Ii.353 | 2,4-dimethyl-3-furyl | $C_2H_5$ |
| Ii.354 | 2,4-dimethyl-3-furyl | $n-C_3H_7$ |
| Ii.355 | 2,4-dimethyl-3-furyl | $i-C_3H_7$ |
| Ii.356 | 2,4-dimethyl-3-furyl | $n-C_4H_9$ |
| Ii.357 | 2,4-dimethyl-3-furyl | $CH_2-CH=CH_2$ |
| Ii.358 | 2,4-dimethyl-3-furyl | $CH_2-C\equiv CH$ |
| Ii.359 | 2,4-dimethyl-3-furyl | phenyl |
| Ii.360 | 2,4-dimethyl-3-furyl | benzyl |
| Ii.361 | 2,5-dimethyl-3-furyl | $CH_3$ |
| Ii.362 | 2,5-dimethyl-3-furyl | $C_2H_5$ |
| Ii.363 | 2,5-dimethyl-3-furyl | $n-C_3H_7$ |
| Ii.364 | 2,5-dimethyl-3-furyl | $i-C_3H_7$ |

TABLE 2-continued

Ii

[Structure: R¹-N-N=N-N(C(=O))-C(=O)-N(R²)-tetrahydropyran-4-yl, a 1,2,3,4-tetrazol-5(4H)-one ring with carboxamide]

| No. | R¹ | R² |
|---|---|---|
| Ii.365 | 2,5-dimethyl-3-furyl | n-$C_4H_9$ |
| Ii.366 | 2,5-dimethyl-3-furyl | $CH_2$—CH=$CH_2$ |
| Ii.367 | 2,5-dimethyl-3-furyl | $CH_2$—C≡CH |
| Ii.368 | 2,5-dimethyl-3-furyl | phenyl |
| Ii.369 | 2,5-dimethyl-3-furyl | benzyl |
| Ii.370 | thiophen-2-yl | $CH_3$ |
| Ii.371 | thiophen-2-yl | $C_2H_5$ |
| Ii.372 | thiophen-2-yl | n-$C_3H_7$ |
| Ii.373 | thiophen-2-yl | i-$C_3H_7$ |
| Ii.374 | thiophen-2-yl | n-$C_4H_9$ |
| Ii.375 | thiophen-2-yl | $CH_2$—CH=$CH_2$ |
| Ii.376 | thiophen-2-yl | $CH_2$—C≡CH |
| Ii.377 | thiophen-2-yl | phenyl |
| Ii.378 | thiophen-2-yl | benzyl |
| Ii.379 | thiophen-3-yl | $CH_3$ |
| Ii.380 | thiophen-3-yl | $C_2H_5$ |
| Ii.381 | thiophen-3-yl | n-$C_3H_7$ |
| Ii.382 | thiophen-3-yl | i-$C_3H_7$ |
| Ii.383 | thiophen-3-yl | n-$C_4H_9$ |
| Ii.384 | thiophen-3-yl | $CH_2$—CH=$CH_2$ |
| Ii.385 | thiophen-3-yl | $CH_2$—C≡CH |
| Ii.386 | thiophen-3-yl | phenyl |
| Ii.387 | thiophen-3-yl | benzyl |
| Ii.388 | 3-chlorothiophen-2-yl | $CH_3$ |
| Ii.389 | 3-chlorothiophen-2-yl | $C_2H_5$ |
| Ii.390 | 3-chlorothiophen-2-yl | n-$C_3H_7$ |
| Ii.391 | 3-chlorothiophen-2-yl | i-$C_3H_7$ |
| Ii.392 | 3-chlorothiophen-2-yl | n-$C_4H_9$ |
| Ii.393 | 3-chlorothiophen-2-yl | $CH_2$—CH=$CH_2$ |
| Ii.394 | 3-chlorothiophen-2-yl | $CH_2$—C≡CH |
| Ii.395 | 3-chlorothiophen-2-yl | phenyl |
| Ii.396 | 3-chlorothiophen-2-yl | benzyl |
| Ii.397 | 3-methylthiophen-2-yl | $CH_3$ |
| Ii.398 | 3-methylthiophen-2-yl | $C_2H_5$ |
| Ii.399 | 3-methylthiophen-2-yl | n-$C_3H_7$ |
| Ii.400 | 3-methylthiophen-2-yl | i-$C_3H_7$ |
| Ii.401 | 3-methylthiophen-2-yl | n-$C_4H_9$ |
| Ii.402 | 3-methylthiophen-2-yl | $CH_2$—CH=$CH_2$ |
| Ii.403 | 3-methylthiophen-2-yl | $CH_2$—C≡CH |
| Ii.404 | 3-methylthiophen-2-yl | phenyl |
| Ii.405 | 3-methylthiophen-2-yl | benzyl |
| Ii.406 | 5-chlorothiophen-2-yl | $CH_3$ |
| Ii.407 | 5-chlorothiophen-2-yl | $C_2H_5$ |
| Ii.408 | 5-chlorothiophen-2-yl | n-$C_3H_7$ |
| Ii.409 | 5-chlorothiophen-2-yl | i-$C_3H_7$ |
| Ii.410 | 5-chlorothiophen-2-yl | n-$C_4H_9$ |
| Ii.411 | 5-chlorothiophen-2-yl | $CH_2$—CH=$CH_2$ |
| Ii.412 | 5-chlorothiophen-2-yl | $CH_2$—C≡CH |
| Ii.413 | 5-chlorothiophen-2-yl | phenyl |
| Ii.414 | 5-chlorothiophen-2-yl | benzyl |
| Ii.415 | 1-methyl-2-pyrrolyl | $CH_3$ |
| Ii.416 | 1-methyl-2-pyrrolyl | $C_2H_5$ |
| Ii.417 | 1-methyl-2-pyrrolyl | n-$C_3H_7$ |
| Ii.418 | 1-methyl-2-pyrrolyl | i-$C_3H_7$ |
| Ii.419 | 1-methyl-2-pyrrolyl | n-$C_4H_9$ |
| Ii.420 | 1-methyl-2-pyrrolyl | $CH_2$—CH=$CH_2$ |
| Ii.421 | 1-methyl-2-pyrrolyl | $CH_2$—C≡CH |
| Ii.422 | 1-methyl-2-pyrrolyl | phenyl |
| Ii.423 | 1-methyl-2-pyrrolyl | benzyl |
| Ii.424 | 3,5-dimethyl-4-isoxazolyl | $CH_3$ |
| Ii.425 | 3,5-dimethyl-4-isoxazolyl | $C_2H_5$ |
| Ii.426 | 3,5-dimethyl-4-isoxazolyl | n-$C_3H_7$ |
| Ii.427 | 3,5-dimethyl-4-isoxazolyl | i-$C_3H_7$ |
| Ii.428 | 3,5-dimethyl-4-isoxazolyl | n-$C_4H_9$ |
| Ii.429 | 3,5-dimethyl-4-isoxazolyl | $CH_2$—CH=$CH_2$ |
| Ii.430 | 3,5-dimethyl-4-isoxazolyl | $CH_2$—C≡CH |
| Ii.431 | 3,5-dimethyl-4-isoxazolyl | phenyl |
| Ii.432 | 3,5-dimethyl-4-isoxazolyl | benzyl |
| Ii.433 | 5-methyl-3-isoxazolyl | $CH_3$ |
| Ii.434 | 5-methyl-3-isoxazolyl | $C_2H_5$ |
| Ii.435 | 5-methyl-3-isoxazolyl | n-$C_3H_7$ |
| Ii.436 | 5-methyl-3-isoxazolyl | i-$C_3H_7$ |
| Ii.437 | 5-methyl-3-isoxazolyl | n-$C_4H_9$ |
| Ii.438 | 5-methyl-3-isoxazolyl | $CH_2$—CH=$CH_2$ |
| Ii.439 | 5-methyl-3-isoxazolyl | $CH_2$—C≡CH |
| Ii.440 | 5-methyl-3-isoxazolyl | phenyl |
| Ii.441 | 5-methyl-3-isoxazolyl | benzyl |
| Ii.442 | 2,4-dimethyl-5-thiazolyl | $CH_3$ |
| Ii.443 | 2,4-dimethyl-5-thiazolyl | $C_2H_5$ |
| Ii.444 | 2,4-dimethyl-5-thiazolyl | n-$C_3H_7$ |
| Ii.445 | 2,4-dimethyl-5-thiazolyl | i-$C_3H_7$ |
| Ii.446 | 2,4-dimethyl-5-thiazolyl | n-$C_4H_9$ |
| Ii.447 | 2,4-dimethyl-5-thiazolyl | $CH_2$—CH=$CH_2$ |
| Ii.448 | 2,4-dimethyl-5-thiazolyl | $CH_2$—C≡CH |
| Ii.449 | 2,4-dimethyl-5-thiazolyl | phenyl |
| Ii.450 | 2,4-dimethyl-5-thiazolyl | benzyl |
| Ii.451 | 3-methyl-5-isothiazolyl | $CH_3$ |
| Ii.452 | 3-methyl-5-isothiazolyl | $C_2H_5$ |
| Ii.453 | 3-methyl-5-isothiazolyl | n-$C_3H_7$ |
| Ii.454 | 3-methyl-5-isothiazolyl | i-$C_3H_7$ |
| Ii.455 | 3-methyl-5-isothiazolyl | n-$C_4H_9$ |
| Ii.456 | 3-methyl-5-isothiazolyl | $CH_2$—CH=$CH_2$ |
| Ii.457 | 3-methyl-5-isothiazolyl | $CH_2$—C≡CH |
| Ii.458 | 3-methyl-5-isothiazolyl | phenyl |
| Ii.459 | 3-methyl-5-isothiazolyl | benzyl |
| Ii.460 | 1,3,5-trimethyl-4-pyrazolyl | $CH_3$ |
| Ii.461 | 1,3,5-trimethyl-4-pyrazolyl | $C_2H_5$ |
| Ii.462 | 1,3,5-trimethyl-4-pyrazolyl | n-$C_3H_7$ |
| Ii.463 | 1,3,5-trimethyl-4-pyrazolyl | i-$C_3H_7$ |
| Ii.464 | 1,3,5-trimethyl-4-pyrazolyl | n-$C_4H_9$ |
| Ii.465 | 1,3,5-trimethyl-4-pyrazolyl | $CH_2$—CH=$CH_2$ |
| Ii.466 | 1,3,5-trimethyl-4-pyrazolyl | $CH_2$—C≡CH |
| Ii.467 | 1,3,5-trimethyl-4-pyrazolyl | phenyl |
| Ii.468 | 1,3,5-trimethyl-4-pyrazolyl | benzyl |
| Ii.469 | 5-chloro-1,3-dimethyl-4-pyrazolyl | $CH_3$ |
| Ii.470 | 5-chloro-1,3-dimethyl-4-pyrazolyl | $C_2H_5$ |
| Ii.471 | 5-chloro-1,3-dimethyl-4-pyrazolyl | n-$C_3H_7$ |
| Ii.472 | 5-chloro-1,3-dimethyl-4-pyrazolyl | i-$C_3H_7$ |
| Ii.473 | 5-chloro-1,3-dimethyl-4-pyrazolyl | n-$C_4H_9$ |
| Ii.474 | 5-chloro-1,3-dimethyl-4-pyrazolyl | $CH_2$—CH=$CH_2$ |
| Ii.475 | 5-chloro-1,3-dimethyl-4-pyrazolyl | $CH_2$—C≡CH |
| Ii.476 | 5-chloro-1,3-dimethyl-4-pyrazolyl | phenyl |
| Ii.477 | 5-chloro-1,3-dimethyl-4-pyrazolyl | benzyl |
| Ii.478 | 1,4-dimethyl-3-pyrazolyl | $CH_3$ |
| Ii.479 | 1,4-dimethyl-3-pyrazolyl | $C_2H_5$ |
| Ii.480 | 1,4-dimethyl-3-pyrazolyl | n-$C_3H_7$ |
| Ii.481 | 1,4-dimethyl-3-pyrazolyl | i-$C_3H_7$ |
| Ii.482 | 1,4-dimethyl-3-pyrazolyl | n-$C_4H_9$ |
| Ii.483 | 1,4-dimethyl-3-pyrazolyl | $CH_2$—CH=$CH_2$ |
| Ii.484 | 1,4-dimethyl-3-pyrazolyl | $CH_2$—C≡CH |
| Ii.485 | 1,4-dimethyl-3-pyrazolyl | phenyl |
| Ii.486 | 1,4-dimethyl-3-pyrazolyl | benzyl |
| Ii.487 | 2-pyridyl | $CH_3$ |
| Ii.488 | 2-pyridyl | $C_2H_5$ |
| Ii.489 | 2-pyridyl | n-$C_3H_7$ |
| Ii.490 | 2-pyridyl | i-$C_3H_7$ |
| Ii.491 | 2-pyridyl | n-$C_4H_9$ |
| Ii.492 | 2-pyridyl | $CH_2$—CH=$CH_2$ |
| Ii.493 | 2-pyridyl | $CH_2$—C≡CH |
| Ii.494 | 2-pyridyl | phenyl |
| Ii.495 | 2-pyridyl | benzyl |
| Ii.496 | 3-pyridyl | $CH_3$ |
| Ii.497 | 3-pyridyl | $C_2H_5$ |
| Ii.498 | 3-pyridyl | n-$C_3H_7$ |

TABLE 2-continued

Ii $$R^1-N(C=O)-N(C=O)-N(R^2)-\text{(tetrahydropyran-4-yl)}, \text{tetrazolinone}$$

| No. | R¹ | R² |
|---|---|---|
| Ii.499 | 3-pyridyl | i-C₃H₇ |
| Ii.500 | 3-pyridyl | n-C₄H₉ |
| Ii.501 | 3-pyridyl | CH₂—CH=CH₂ |
| Ii.502 | 3-pyridyl | CH₂—C≡CH |
| Ii.503 | 3-pyridyl | phenyl |
| Ii.504 | 3-pyridyl | benzyl |
| Ii.505 | 4-pyridyl | CH₃ |
| Ii.506 | 4-pyridyl | C₂H₅ |
| Ii.507 | 4-pyridyl | n-C₃H₇ |
| Ii.508 | 4-pyridyl | i-C₃H₇ |
| Ii.509 | 4-pyridyl | n-C₄H₉ |
| Ii.510 | 4-pyridyl | CH₂—CH=CH₂ |
| Ii.511 | 4-pyridyl | CH₂—C≡CH |
| Ii.512 | 4-pyridyl | phenyl |
| Ii.513 | 4-pyridyl | benzyl |
| Ii.514 | 2-chloro-3-pyridyl | CH₃ |
| Ii.515 | 2-chloro-3-pyridyl | C₂H₅ |
| Ii.516 | 2-chloro-3-pyridyl | n-C₃H₇ |
| Ii.517 | 2-chloro-3-pyridyl | i-C₃H₇ |
| Ii.518 | 2-chloro-3-pyridyl | n-C₄H₉ |
| Ii.519 | 2-chloro-3-pyridyl | CH₂—CH=CH₂ |
| Ii.520 | 2-chloro-3-pyridyl | CH₂—C≡CH |
| Ii.521 | 2-chloro-3-pyridyl | phenyl |
| Ii.522 | 2-chloro-3-pyridyl | benzyl |
| Ii.523 | 2-chloro-5-pyridyl | CH₃ |
| Ii.524 | 2-chloro-5-pyridyl | C₂H₅ |
| Ii.525 | 2-chloro-5-pyridyl | n-C₃H₇ |
| Ii.526 | 2-chloro-5-pyridyl | i-C₃H₇ |
| Ii.527 | 2-chloro-5-pyridyl | n-C₄H₉ |
| Ii.528 | 2-chloro-5-pyridyl | CH₂—CH=CH₂ |
| Ii.529 | 2-chloro-5-pyridyl | CH₂—C≡CH |
| Ii.530 | 2-chloro-5-pyridyl | phenyl |
| Ii.531 | 2-chloro-5-pyridyl | benzyl |
| Ii.532 | 2-chloro-4-pyridyl | CH₃ |
| Ii.533 | 2-chloro-4-pyridyl | C₂H₅ |
| Ii.534 | 2-chloro-4-pyridyl | n-C₃H₇ |
| Ii.535 | 2-chloro-4-pyridyl | i-C₃H₇ |
| Ii.536 | 2-chloro-4-pyridyl | n-C₄H₉ |
| Ii.537 | 2-chloro-4-pyridyl | CH₂—CH=CH₂ |
| Ii.538 | 2-chloro-4-pyridyl | CH₂—C≡CH |
| Ii.539 | 2-chloro-4-pyridyl | phenyl |
| Ii.540 | 2-chloro-4-pyridyl | benzyl |
| Ii.541 | 3-chloro-4-pyridyl | CH₃ |
| Ii.542 | 3-chloro-4-pyridyl | C₂H₅ |
| Ii.543 | 3-chloro-4-pyridyl | n-C₃H₇ |
| Ii.544 | 3-chloro-4-pyridyl | i-C₃H₇ |
| Ii.545 | 3-chloro-4-pyridyl | n-C₄H₉ |
| Ii.546 | 3-chloro-4-pyridyl | CH₂—CH=CH₂ |
| Ii.547 | 3-chloro-4-pyridyl | CH₂—C≡CH |
| Ii.548 | 3-chloro-4-pyridyl | phenyl |
| Ii.549 | 3-chloro-4-pyridyl | benzyl |
| Ii.550 | 2-methyl-3-pyridyl | CH₃ |
| Ii.551 | 2-methyl-3-pyridyl | C₂H₅ |
| Ii.552 | 2-methyl-3-pyridyl | n-C₃H₇ |
| Ii.553 | 2-methyl-3-pyridyl | i-C₃H₇ |
| Ii.554 | 2-methyl-3-pyridyl | n-C₄H₉ |
| Ii.555 | 2-methyl-3-pyridyl | CH₂—CH=CH₂ |
| Ii.556 | 2-methyl-3-pyridyl | CH₂—C≡CH |
| Ii.557 | 2-methyl-3-pyridyl | phenyl |
| Ii.558 | 2-methyl-3-pyridyl | benzyl |
| Ii.559 | 2-(methylthio)-3-pyridyl | CH₃ |
| Ii.560 | 2-(methylthio)-3-pyridyl | C₂H₅ |
| Ii.561 | 2-(methylthio)-3-pyridyl | n-C₃H₇ |
| Ii.562 | 2-(methylthio)-3-pyridyl | i-C₃H₇ |
| Ii.563 | 2-(methylthio)-3-pyridyl | n-C₄H₉ |
| Ii.564 | 2-(methylthio)-3-pyridyl | CH₂—CH=CH₂ |
| Ii.565 | 2-(methylthio)-3-pyridyl | CH₂—C≡CH |
| Ii.566 | 2-(methylthio)-3-pyridyl | phenyl |
| Ii.567 | 2-(methylthio)-3-pyridyl | benzyl |
| Ii.568 | 4-(trifluoromethyl)-3-pyridyl | CH₃ |
| Ii.569 | 4-(trifluoromethyl)-3-pyridyl | C₂H₅ |
| Ii.570 | 4-(trifluoromethyl)-3-pyridyl | n-C₃H₇ |
| Ii.571 | 4-(trifluoromethyl)-3-pyridyl | i-C₃H₇ |
| Ii.572 | 4-(trifluoromethyl)-3-pyridyl | n-C₄H₉ |
| Ii.573 | 4-(trifluoromethyl)-3-pyridyl | CH₂—CH=CH₂ |
| Ii.574 | 4-(trifluoromethyl)-3-pyridyl | CH₂—C≡CH |
| Ii.575 | 4-(trifluoromethyl)-3-pyridyl | phenyl |
| Ii.576 | 4-(trifluoromethyl)-3-pyridyl | benzyl |
| Ii.577 | 2,6-dichloro-3-pyridyl | CH₃ |
| Ii.578 | 2,6-dichloro-3-pyridyl | C₂H₅ |
| Ii.579 | 2,6-dichloro-3-pyridyl | n-C₃H₇ |
| Ii.580 | 2,6-dichloro-3-pyridyl | i-C₃H₇ |
| Ii.581 | 2,6-dichloro-3-pyridyl | n-C₄H₉ |
| Ii.582 | 2,6-dichloro-3-pyridyl | CH₂—CH=CH₂ |
| Ii.583 | 2,6-dichloro-3-pyridyl | CH₂—C≡CH |
| Ii.584 | 2,6-dichloro-3-pyridyl | phenyl |
| Ii.585 | 2,6-dichloro-3-pyridyl | benzyl |
| Ii.586 | 2,6-dichloro-4-pyridyl | CH₃ |
| Ii.587 | 2,6-dichloro-4-pyridyl | C₂H₅ |
| Ii.588 | 2,6-dichloro-4-pyridyl | n-C₃H₇ |
| Ii.589 | 2,6-dichloro-4-pyridyl | i-C₃H₇ |
| Ii.590 | 2,6-dichloro-4-pyridyl | n-C₄H₉ |
| Ii.591 | 2,6-dichloro-4-pyridyl | CH₂—CH=CH₂ |
| Ii.592 | 2,6-dichloro-4-pyridyl | CH₂—C≡CH |
| Ii.593 | 2,6-dichloro-4-pyridyl | phenyl |
| Ii.594 | 2,6-dichloro-4-pyridyl | benzyl |
| Ii.595 | 2-chloro-4-methyl-3-pyridyl | CH₃ |
| Ii.596 | 2-chloro-4-methyl-3-pyridyl | C₂H₅ |
| Ii.597 | 2-chloro-4-methyl-3-pyridyl | n-C₃H₇ |
| Ii.598 | 2-chloro-4-methyl-3-pyridyl | i-C₃H₇ |
| Ii.599 | 2-chloro-4-methyl-3-pyridyl | n-C₄H₉ |
| Ii.600 | 2-chloro-4-methyl-3-pyridyl | CH₂—CH=CH₂ |
| Ii.601 | 2-chloro-4-methyl-3-pyridyl | CH₂—C≡CH |
| Ii.602 | 2-chloro-4-methyl-3-pyridyl | phenyl |
| Ii.603 | 2-chloro-4-methyl-3-pyridyl | benzyl |

Finally, particular preference is given to the heterocyclic tetrazolinonecarboxamides below:

The compounds Ik.1–Ik.603 which differ from the corresponding compounds Ii.1–Ii.603 only in that Het is tetrahydrofuran-3-yl:

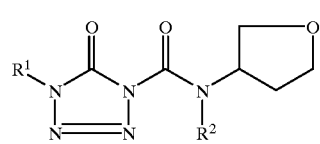

Ik

The compounds Il.1–Il.603 which differ from the corresponding compounds Ii.1–Ii.603 only in that Het is furan-3-yl:

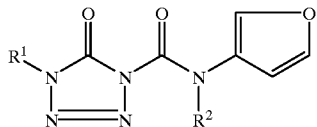

The compounds Im.1–Im.603 which differ from the corresponding compounds Ii.1–Ii.603 only in that Het is 2,4-dimethylfuran-3-yl:

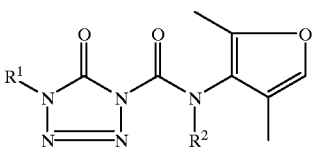

The compounds In.1–In.603 which differ from the corresponding compounds Ii.1–Ii.603 only in that Het is tetrahydro-2H-thio-pyran-4-yl:

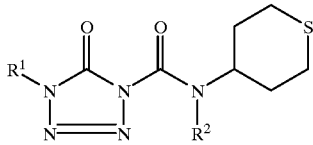

The compounds Io.1–Io.603 which differ from the corresponding compounds Ii.1–Ii.603 only in that Het is tetrahydrothiophen- 3-yl:

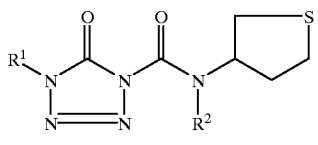

The compounds Ip.1–Ip.603 which differ from the corresponding compounds Ii.1–Ii.603 only in that Het is thiophen-3-yl:

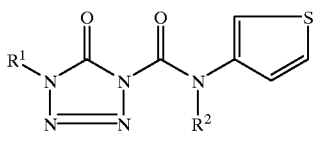

The compounds Iq.1–Iq.603 which differ from the corresponding compounds Ii.1–Ii.603 only in that Het is 2,4-dimethylthiophen-3-yl:

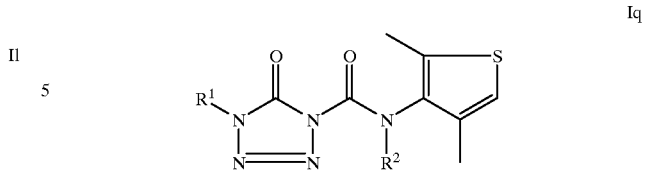

Likewise, very particular preference is given to the substituted tetrazolinecarboxamides of the formula I where the variables have the following meaning:

Het is tetrahydrofuran-3-yl, tetrahydrothiophen-3-yl, 2,4-dimethyltetrahydrothiophen-3-yl, tetrahydro-2H-pyran-4-yl or tetrahydro-2H-thiopyran-4yl;

$R^1$ is $C_1$–$C_6$-haloalkyl or phenyl, which may be unsubstituted or may carry one to four substituents and is in particular unsubstituted or may carry one to two substituents, selected from the group consisting of halogen, $C_1$–$C_4$-alkyl or $C_1$–$C_4$ -haloalkyl;

$R^2$ is $C_1$–$C_6$-alkyl; in particular $C_1$–$C_4$-alkyl.

The substituted tetrazolinonecarboxamides of the formula I can be obtained in a variety of ways, in particular by one of the following processes:

A) Reaction of tetrazolinones of the formula II in the presence of a base with a carbamoyl chloride of the formula III, or initial deprotonation of the tetrazolinone of the formula II with a base and, if desired, isolation of the resulting salt of the formula IV and subsequent reaction with a carbamoyl chloride of the formula III.

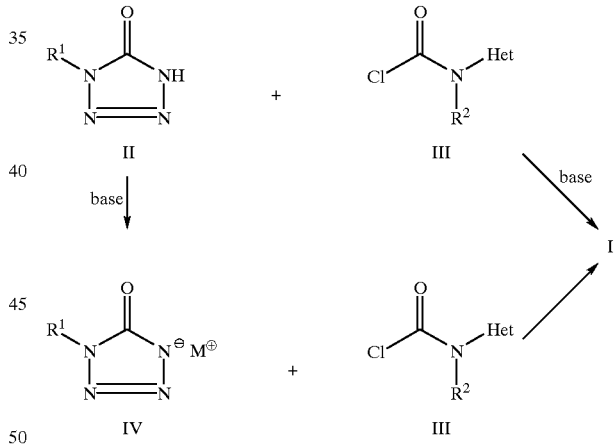

where $M^+$ in the formula IV is a cation derived from the base, for example triethylammonium, tetraethylammonium, $Na^+$, $K^+$ or $Ca^{2+}/2$.

B) Reaction of a tetrazolinonecarbonyl chloride of the formula VI in the presence of a base with an amine of the formula V.

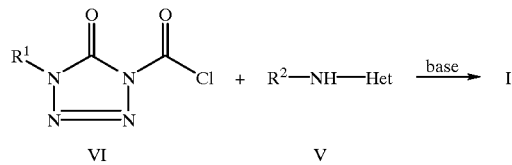

Suitable bases for the two processes A) and B) are amines, such as triethylamine, pyridine and 4-dimethylaminopyridine, tetraalkyl- or tetraarylammonium hydroxides, such as tetraethylammonium hydroxide, alkali metal carbonates, bicarbonates and hydrides, such as sodium carbonate, sodium bicarbonate or sodium hydride, alkali metal hydroxides or alkaline earth metal hydroxides, such as sodium hydroxide, potassium hydroxide or calcium hydroxide.

The salts of the formula IV which are readily isolated, for example as triethylammonium, tetraethylammonium, sodium, potassium or calcium salts, can be obtained by reaction of the the tetrazolinones of the formula II with a base.

The tetrazolinones of the formula II are known per se and can be obtained, for example, by reacting the corresponding aliphatic or aromatic isocyanates with azidotrimethylsilane or with aluminum azide prepared in situ. (Houben-Weyl, Vol. E8d, pages 692–693, Thieme-Verlag Stuttgart 1994).

The carbamoyl chlorides of the formula II where the radical Het has the meanings listed for the compounds of the formula I and $R^2$ has also the meanings listed for the compounds of the formula I, with the exception of hydrogen, are novel.

The carbamoyl chlorides of the formula III having the substituents Het and $R^2$ listed in Table 3 are suitable for preparing the particularly preferred substituted tetrazolinonecarboxamides.

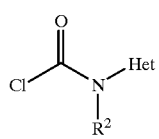

III

TABLE 3

| No. | Het | $R^2$ |
|---|---|---|
| III.1 | tetrahydrofuran-3-yl | $CH_3$ |
| III.2 | tetrahydrofuran-3-yl | $C_2H_5$ |
| III.3 | tetrahydrofuran-3-yl | $n\text{-}C_3H_7$ |
| III.4 | tetrahydrofuran-3-yl | $i\text{-}C_3H_7$ |
| III.5 | tetrahydrofuran-3-yl | $n\text{-}C_4H_9$ |
| III.6 | tetrahydrofuran-3-yl | $CH_2\text{—}CH\text{=}CH_2$ |
| III.7 | tetrahydrofuran-3-yl | $CH_2\text{—}C\text{≡}CH$ |
| III.8 | tetrahydrofuran-3-yl | phenyl |
| III.9 | tetrahydrofuran-3-yl | benzyl |
| III.10 | tetrahydro-2H-pyran-4-yl | $CH_3$ |
| III.11 | tetrahydro-2H-pyran-4-yl | $C_2H_5$ |
| III.12 | tetrahydro-2H-pyran-4-yl | $n\text{-}C_3H_7$ |
| III.13 | tetrahydro-2H-pyran-4-yl | $i\text{-}C_3H_7$ |
| III.14 | tetrahydro-2H-pyran-4-yl | $n\text{-}C_4H_9$ |
| III.15 | tetrahydro-2H-pyran-4-yl | $CH_2\text{—}CH\text{=}CH_2$ |
| III.16 | tetrahydro-2H-pyran-4-yl | $CH_2\text{—}C\text{≡}CH$ |
| III.17 | tetrahydro-2H-pyran-4-yl | phenyl |
| III.18 | tetrahydro-2H-pyran-4-yl | benzyl |
| III.19 | tetrahydrothiophen-3-yl | $CH_3$ |
| III.20 | tetrahydrothiophen-3-yl | $C_2H_5$ |
| III.21 | tetrahydrothiophen-3-yl | $n\text{-}C_3H_7$ |
| III.22 | tetrahydrothiophen-3-yl | $i\text{-}C_3H_7$ |
| III.23 | tetrahydrothiophen-3-yl | $n\text{-}C_4H_9$ |
| III.24 | tetrahydrothiophen-3-yl | $CH_2\text{—}CH\text{=}CH_2$ |
| III.25 | tetrahydrothiophen-3-yl | $CH_2\text{—}C\text{≡}CH$ |
| III.26 | tetrahydrothiophen-3-yl | phenyl |
| III.27 | tetrahydrothiophen-3-yl | benzyl |
| III.28 | tetrahydro-2H-thiopyran-4-yl | $CH_3$ |
| III.29 | tetrahydro-2H-thiopyran-4-yl | $C_2H_5$ |
| III.30 | tetrahydro-2H-thiopyran-4-yl | $n\text{-}C_3H_7$ |
| III.31 | tetrahydro-2H-thiopyran-4-yl | $i\text{-}C_3H_7$ |

TABLE 3-continued

| No. | Het | $R^2$ |
|---|---|---|
| III.32 | tetrahydro-2H-thiopyran-4-yl | $n\text{-}C_4H_9$ |
| III.33 | tetrahydro-2H-thiopyran-4-yl | $CH_2\text{—}CH\text{=}CH_2$ |
| III.34 | tetrahydro-2H-thiopyran-4-yl | $CH_2\text{—}C\text{≡}CH$ |
| III.35 | tetrahydro-2H-thiopyran-4-yl | phenyl |
| III.36 | tetrahydro-2H-thiopyran-4-yl | benzyl |
| III.37 | furan-3-yl | $CH_3$ |
| III.38 | furan-3-yl | $C_2H_5$ |
| III.39 | furan-3-yl | $n\text{-}C_3H_7$ |
| III.40 | furan-3-yl | $i\text{-}C_3H_7$ |
| III.41 | furan-3-yl | $n\text{-}C_4H_9$ |
| III.42 | furan-3-yl | $CH_2\text{—}CH\text{=}CH_2$ |
| III.43 | furan-3-yl | $CH_2\text{—}C\text{≡}CH$ |
| III.44 | furan-3-yl | phenyl |
| III.45 | furan-3-yl | benzyl |
| III.46 | 2,4-dimethylfuran-3-yl | $CH_3$ |
| III.47 | 2,4-dimethylfuran-3-yl | $C_2H_5$ |
| III.48 | 2,4-dimethylfuran-3-yl | $n\text{-}C_3H_7$ |
| III.49 | 2,4-dimethylfuran-3-yl | $i\text{-}C_3H_7$ |
| III.50 | 2,4-dimethylfuran-3-yl | $n\text{-}C_4H_9$ |
| III.51 | 2,4-dimethylfuran-3-yl | $CH_2\text{—}CH\text{=}CH_2$ |
| III.52 | 2,4-dimethylfuran-3-yl | $CH_2\text{—}C\text{≡}CH$ |
| III.53 | 2,4-dimethylfuran-3-yl | phenyl |
| III.54 | 2,4-dimethylfuran-3-yl | benzyl |
| III.55 | thiophen-3-yl | $CH_3$ |
| III.56 | thiophen-3-yl | $C_2H_5$ |
| III.57 | thiophen-3-yl | $n\text{-}C_3H_7$ |
| III.58 | thiophen-3-yl | $i\text{-}C_3H_7$ |
| III.59 | thiophen-3-yl | $n\text{-}C_4H_9$ |
| III.60 | thiophen-3-yl | $CH_2\text{—}CH\text{=}CH_2$ |
| III.61 | thiophen-3-yl | $CH_2\text{—}C\text{≡}CH$ |
| III.62 | thiophen-3-yl | phenyl |
| III.63 | thiophen-3-yl | benzyl |
| III.64 | 2,4-dimethylthiophen-3-yl | $CH_3$ |
| III.65 | 2,4-dimethylthiophen-3-yl | $C_2H_5$ |
| III.66 | 2,4-dimethylthiophen-3-yl | $n\text{-}C_3H_7$ |
| III.67 | 2,4-dimethylthiophen-3-yl | $i\text{-}C_3H_7$ |
| III.68 | 2,4-dimethylthiophen-3-yl | $n\text{-}C_4H_9$ |
| III.69 | 2,4-dimethylthiophen-3-yl | $CH_2\text{—}CH\text{=}CH_2$ |
| III.70 | 2,4-dimethylthiophen-3-yl | $CH_2\text{—}C\text{≡}CH$ |
| III.71 | 2,4-dimethylthiophen-3-yl | phenyl |
| III.72 | 2,4-dimethylthiophen-3-yl | benzyl |

The particularly preferred embodiments of the carbamoyl chlorides of the formula III with respect to the variables $R^2$ and Het correspond to those of the substituted tetrazolinonecarboxamides of the formula I.

The carbamoyl chlorides of the formula III can be prepared, for example, by phosgenation of the corresponding amines of the formula V. Suitable phosgenating agents are phosgene, diphosgene or triphosgene. The phosgenation can alternatively be carried out in the presence or the absence of a base, for example one of the bases mentioned above. It is also possible to convert the amine of the formula V prior to phosgenation by reaction with an acid into the corresponding acid addition salt, for example into the hydrochlorides using hydrogen chloride.

A process suitable for preparing the amines of the formula V is, for example, the reductive amination of heterocyclic ketones of the formula VII with amines of the formula VIII, or, alternatively, the reductive amination of heterocyclic amines of the formula IX with aldehydes or ketones of the formula X. This reaction is well known per se (for example A. F. Abdel-Magid, K. G. Carson, B. D. Harris, C. A. Maryanoff, R. D. Shah, *J. Org. Chem.* 61 (1996), 3849, and the literature cited therein).

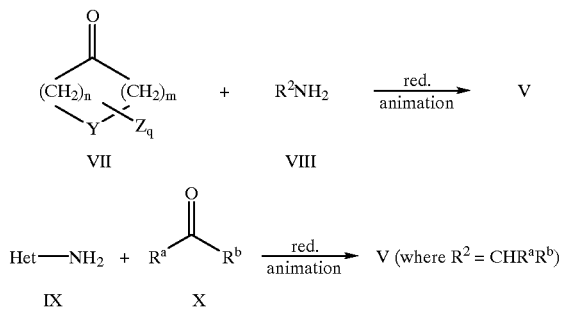

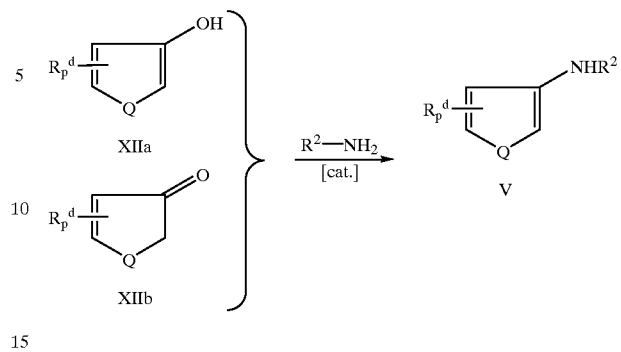

where n,m is the integer 1 or 2;

q is the integer 0, 1 or 2;

Y is O or S;

Z is F, Cl, Br, I, $C_1$–$C_6$-alkyl or $C_1$–$C_6$-haloalkyl;

$R^a$, $R^b$ $R^a$ and $R^b$ together with the CH group to which they are attached form the radical $R^2$ which is, as far as possible, as defined for the compounds of the formula I.

Furthermore, the amines of the formula V can also be prepared by acylation of amines of the formula IX and subsequent reduction of the amides XI, which are formed as intermediate. Both reactions are known per se (see, for example, Houbey-Weyl, Methoden der Organischen Chemie, Georg Thieme Verlag, Vol. E5, Stuttgart 1985, p. 972 ff., p. 977 ff. and Vol. XI/1, Stuttgart 1957, p. 574 ff.).

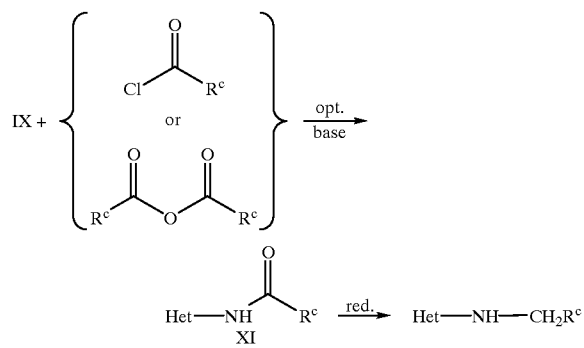

where —$CH_2R^c$ is a radical $R^2$, as defined for the compounds of the formula I.

Furthermore, amines of the formula V where Het=thiophen-3-yl or furan-3-yl with or without substitution can be prepared by reaction of compounds of formula XII, which may for their part be present as tautomers XIIa or XIIb or mixtures thereof, with amines $R^2$—$NH_2$, if desired in the presence of a catalyst, for example acids, such as hydrochloric acid or sulfuric acid or Lewis acids, such as boron trifluoride, zinc chloride or titanium tetrachloride, where p is 0, 1, 2 or 3;

Q is oxygen or sulfur;

$R^d$ is halogen, $C_1$–$C_6$-alkyl or $C_1$–$C_6$-haloalkyl.

The tetrazolinonecarbonyl chlorides of the formula VI which are employed for preparing the substituted tetrazolinonecarboxamides of the formula I according to the invention by process B) can be obtained by phosgenation of the corresponding tetrazolinones of the formula II, as described, for example, in EP-A 764 642.

The reactions to prepare the substituted tetrazolinonecarboxamides of the formula I according to the invention and the intermediates of the formulae II to XII required for their preparation are generally carried out in an inert organic solvent, for example in aliphatic or aromatic hydrocarbons, such as hexane, cyclohexane and toluene, halogenated hydrocarbons, such as dichloromethane or 1,2-dichloroethane, ethers, such as diethyl ether, tetrahydrofuran or dioxane, or in aprotic solvents, such as dimethylformamide, dimethyl sulfoxide and acetonitrile, or else in mixtures of the abovementioned solvents.

For all reactions mentioned, the reaction temperature is between the melting point and the boiling point of the reaction mixture, preferably (unless stated otherwise) between 0 and 100° C. To obtain high conversions, it may be advantageous to carry out the reaction at the boiling point of the reaction mixture. The reaction partners are generally employed in equimolar amounts. However, to obtain a better yield, it may also be advantageous to employ one or more reaction partners in an excess of up to approximately ten times the molar amount. The abovementioned reactions are advantageously carried out under atmospheric pressure or under the inherent pressure of the reaction mixture in question.

The substituted tetrazolinonecarboxamides I can normally be prepared by one of the synthesis methods mentioned above. However, for reasons of economy or process engineering, it may be more expedient to prepare some compounds I from similar tetrazolinonecarboxamides which, however, differ in particular in the meaning of the radical $R^1$ or $R^2$, the preparation being carried out in a manner known per se, e.g. by alkylation, condensation reaction, oxidation, olefination, reduction, etherification, esterification or Wittig reaction.

Those starting compounds for the individual processes which are not already known can be obtained in a manner known per se or by a method similar to one of the processes described.

The reaction mixtures are generally worked up by methods known per se, for example by diluting the reaction solution with water followed by isolation of the product by means of filtration, crystallization or solvent extraction, or by removing the solvent, partitioning the residue in a mixture of water and a suitable organic solvent and working up the organic phase to give the product.

The substituted tetrazolinonecarboxamides I may be obtained from the preparation in the form of isomer mixtures, but, if desired, the latter can be separated into the essentially pure isomers by the methods conventionally used for this purpose, such as crystallization or chromatography, also on an optically active adsorbate. Pure optically active isomers may be prepared advantageously from corresponding optically active starting materials.

The compounds I, both as isomer mixtures and in the form of the pure isomers, are suitable as herbicides. The herbicidal compositions comprising I effect very good control of vegetation on non-crop areas, especially at high rates of application. In crops such as wheat, rice, maize, soybeans and cotton, they act against broad-leaved weeds and grass weeds without damaging the crop plants substantially. This effect is observed especially at low rates of application.

Depending on the application method in question, the compounds I, or the herbicidal compositions comprising them, can additionally be employed in a further number of crop plants for eliminating undesirable plants. Suitable crops are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N. rustica), Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera* and *Zea mays.*

In addition, the compounds I can also be used in crops which tolerate the action of herbicides due to breeding, including genetic engineering methods.

The herbicidal compositions can be applied pre- or post-emergence. If the active ingredients are less well tolerated by certain crop plants, it is possible to use application techniques in which the herbicidal compositions are sprayed, with the aid of the spraying equipment, in such a way that they come into as little contact as possible, if any, with the leaves of the sensitive crop plants while reaching the leaves of undesirable plants which grow underneath, or the bare soil surface (post-directed, lay-by).

The compounds I, or the herbicidal compositions comprising them, can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert auxiliaries are essentially: Mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the compounds I, as such or dissolved in an oil or solvent, can be homogenized in water by means of wetting agent, tackifier, dispersant or emulsifier. Alternatively, it is possible to prepare concentrates from active substance, wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignin-sulfite waste liquors or methylcellulose.

Powders, materials for spreading and dusts can be prepared by mixing or concomitant grinding of the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the active ingredients I in the ready-to-use products can be varied within wide ranges. In general, the formulations comprise from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples which follow illustrate the preparation of the compounds according to the invention:
   I. 20 parts by weight of the compound No. Ia.20 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. Ia.29 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. Ia.155 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. Ia.227 are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the active ingredient No. Ie.19 are mixed with 97 parts by weight of finely divided kaolin. This gives a dust which comprises 3% by weight of the active ingredient.

VI. 20 parts by weight of the active ingredient No. Ie.28 are mixed intimately with 2 parts by weight of calcium dodecylbenzenesulfonate, 8 parts by weight of fatty alcohol polyglylcol ether, 2 parts by weight of the sodium salt of a phenol/urea/formaldehyde condensate and 68 parts by weight of a paraffinic mineral oil. This gives a stable oily dispersion.

VII. 1 part by weight of the active ingredient No. Ia.226 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active ingredient No. Ia.20 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

To widen the spectrum of action and to achieve synergistic effects, the substituted tetrazolinonecarboxamides may be mixed, and applied jointly, with a large number of representatives of other groups of herbicidally or growth-regulating active ingredients. Suitable examples of components in mixtures are 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl/aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4, 5,6-tetrahydrophthalimides, oxadiazoles, oxirans, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds I, alone or in combination with other herbicides, in the form of a mixture with even further crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

Depending on the intended aim, the season, the target plant and the growth stage, the rates of application of active ingredient I are from 0.001 to 3.0, preferably 0.01 to 1.0, kg of active substance (a.s.)/ha.

PREPARATION EXAMPLES

Example 1

N-ethyl-N-(tetrahydro-2H-pyran-4-yl)-4-(2-chlorophenyl)-4,5-dihydro-1H-tetrazol-5-one-1-carboxamide (No. Ia.20)

3.7 g (19 mmol) of 1-(2-chlorophenyl)-1,2-dihydro-5H-tetrazol-5-one, 3.6 g (19 mmol) of N-ethyl-N-(tetrahydro-2H-pyran-4-yl)carbamoyl chloride and 2.6 g (21 mmol) of 4-dimethylaminopyridine in 150 ml of toluene were heated under reflux for 5 hours. The organic phase was washed with water, dried over magnesium sulfate, filtered and concentrated. The residue was purified by silica gel column chromatography (eluent hexane/ethyl acetate 2:1). Yield 5.5 g. $^1H$ NMR (270 MHz, in $CDCl_3$): δ=1.20–1.40 (m, 3H), 1.80–2.05 (m, 4H), 3.30–3.60 (m, 4H), 3.70–4.50 (m, 3H), 7.40–7.60 (m, 4H).

Intermediate 1.1

Ethyl(tetrahydro-2H-pyran-4-yl)amine

At 0° C. and with efficient cooling, 51 g (0.5 mol) of conc. sulfuric acid were added dropwise to a solution of 105 g (2.3 mol) of ethylamine in 0.5 l of methanol. 50 g (0.5 mol) of tetrahydro-2H-pyran-4-one and 18.8 g (0.3 mol) of sodium cyanoborhydride were then added successively. After 16 hours at room temperature, the methanol was distilled off, an excess of 10% strength aqueous sodium hydroxide solution was added and the aqueous phase was extracted three times with dichloromethane. The combined organic phases were washed neutral with water, dried over magnesium sulfate and filtered and the residue was distilled. Bp. 76–82° C. (20 mbar), yield 24 g. $^1H$ NMR (250 MHz, in $CDCl_3$): δ=0.86 (s, 1H), 1.13 (t, 3H), 1.40 (dq, 2H), 1.84 (m, 2H), 2.68 (m, 3H), 3.40 (dt, 2H), 3.98 (m, 2H).

Intermediate 1.2

N-ethyl-N-(tetrahydro-2H-pyran-4-yl)carbamoyl chloride (No. III.11)

At −30° C., a solution of 19 g (0.15 mol) of ethyl (tetrahydro- 2H-pyran-4-yl)amine and 14.8 g (0.15 mol) of triethylamine in 10 ml of dichloromethane was slowly added dropwise to a solution of 44 g (0.44 mol) of phosgene in 100 ml of dichloromethane. The mixture was slowly warmed to room temperature (over a period of approximately 3 hours) and then heated under reflux for 30 minutes, excess phosgene was removed using a nitrogen stream, and the solution was concentrated. 200 ml of hexane were added, the solids were filtered off and the filtrate was concentrated. Yield 25.3 g. MS (m/z): 192 [M+H]$^+$, 156 [M–Cl]$^+$.

Example 2

N-methyl-N-(tetrahydro-2H-thiopyran-4-yl)-4-(2-bromophenyl)-4,5-dihydro-1H-tetrazol-5-one-1-carboxamide (No. Ie.28)

Similarly to the process described in Example 1, 2.5 g (10 mmol) of 1-(2-bromophenyl)-1,2-dihydro-5H-tetrazol-5-one, 2 g (10 mmol) of N-methyl-N-(tetrahydro-2H-thiopyran-4-yl)carbamoyl chloride and 1.5 g (12 mmol) of 4-dimethylaminopyridine were reacted. Yield 2.5 g.

Intermediate 2.1

Methyl(tetrahydro-2H-thiopyran-4-yl)amine

Similarly to the process described in intermediate 1.1, 36.8 g (1.2 mol) of methylamine, 30 g (0.26 mol) of tetrahydro-2H-thiopyran-4-one and 9.7 g (0.15 mol) of sodium cyanoborhydride were reacted. Bp. 98° C. (25 mbar), yield 10 g.

$^1$H NMR (400 MHz, in CDCl$_3$): δ=1.06 (s, 1H), 1.48 (dq, 2H), 2.16 (m, 2H), 2.35 (tt, 1H), 2.42 (s, 3H), 2.60–2.70 (m, 4H).

Intermediate 2.2

N-Methyl-N-(tetrahydro-2H-thiopyran-4-yl) carbamoyl chloride (No. III.28)

Similarly to the method described in intermediate 1.2, 22.8 g (0.23 mol) of phosgene, 10 g (76 mmol) of methyl (tetrahydro-2H-thiopyran-4-yl)amine and 7.8 g (76 mmol) of triethylamine were reacted. Yield 13.4 g. MS (m/z): 193 [M]$^+$, 158 [M–Cl]$^+$.

Example 3

N-(2,4-Dimethylthiophen-3-yl)-N-n-propyl-4,5-dihydro-4-(2-fluoro-phenyl)-1H-tetrazol-5-one-1-carboxamide (No. Ih.12)

1.17g (6.5 mmol) of 1,2-dihydro-1-(2-fluorophenyl)-5H-tetrazol-5-one, 1.5 g (6.5 mmol) of N-(2,4-dimethyl-thiophen-3-yl)-N-n-propylcarbamoyl chloride and 1.19 g (9.7 mmol) of 4-dimethylaminopyridine were reacted by the method of the process described in Example 1. Yield 1.9 g.

Precursor 3.1

2,4-Dimethylthiophen-3-yl-(n-propyl)amine

In an atmosphere of inert gas, 34.6 g (0.59 mol) of propylamine were admixed with 10.6 g (78 mmol) of anhydrous zinc chloride powder in the course of which the temperature of the mixture rose strongly. The solution was then admixed with 50 g (0.39 mol) of 2,4-dimethyl-3-hydroxythiophene, introduced into an autoclave and heated at 1700° C. under pressure (approximately 5 bar) for 16 hours. After cooling, the mixture was made alkaline using 50 ml of 33% strength aqueous sodium hydroxide solution and extracted twice with hexane, the combined organic phases were washed three times with water, dried over magnesium sulfate, filtered and concentrated under water pump vacuum, and the residue was distilled. Yield 31.2 g (47%), b.p. 88° C. (2 mbar). $^1$H NMR (270 MHz in CDCl$_3$):δ=0.96 (t, 3H), 1.56 (sext., 2H), 2.12 (s, 3H), 2.31 (s, 3H), 2.96 (t, 2H), 3.18 (s, 1H), 6.61 (s, 1H).

Intermediate 3.2

N-(2,4-Dimethylthiophen-3-yl)-N-n-propylcarbamoyl chloride (No. III.66)

54.5 g (0.54 mol) of phosgene, 31 g (0.18 mol) of 2,4-dimethylthiophen-3-yl-(n-propyl)amine and 18.5 g (0.18 mol) of triethylamine were reacted similarly to the process described in Intermediate 1.2. Yield 40 g. MS (m/z): 231 [M]$^+$, 202 [M–C$_2$H$_5$]$^+$, 196 [M–Cl]$^+$.

Example 4

N-Methyl-N-(tetrahydro-2H-pyran-4-yl)-4,5-dihydro-4-(2-trifluoro-methylphenyl)-5H-tetrazol-5-one-1-carboxamide (No. Ia.388)

1.94 g (8,45 mmol) of 1,2-dihydro-1-(2-trifluoromethylphenyl)-5H-tetrazol-5-one, 1.5 g (8.5 mmol) of N-methyl-N-(tetrahydro-2H-pyran-4-yl)carbamoyl chloride and 1.55 g (12.7 mmol) of 4-dimethylaminopyridine were reacted by the method of the process described in Example 1. Yield 0.55 g.

Intermediate 4.1

N-Methyl-N-(tetrahydro-2H-pyran-4-yl)amine

At –70° C., 170 g (5.5 mol) of gaseous methylamine were introduced into 1.5 l of methanol. The solution was admixed dropwise with 100 g (1 mol) of sulfuric acid. 100 g (1 mol) of tetrahydro-4H-pyran-4-one and 36.4 g (0.6 mol) of sodium borocyanohydride were added in succession, and the mixture was stirred at room temperature for 3 days, resulting in a white precipitate. The solution was filtered and the filtrate was distilled. B.p. 56–58° C. (12 mm), yield 96 g. $^1$H NMR (270 MHz, in CDCl$_3$): δ=1.30 (s, 1H), 1.38 (dq, 2H), 1.85 (dd, 2H), 2.43 (s, 3H), 2.57 (tt, 1H), 3.41 (dt, 2H), 3.99 (dt, 2H).

Intermediate 4.2

N-Methyl-N-(tetrahydro-2H-pyran-4-yl)carbamoyl chloride (No. III.10)

248 g (2.5 mol) of phosgene, 96 g (0.83 mol) of N-methyl-N-(tetrahydro-2H-pyran-4-yl)amine and 84 g (0.83 mol) of triethylamine were reacted by the method of the process described in Intermediate 1.2. Yield 108 g. $^1$H NMR (250 MHz, in CDCl$_3$): δ=1.60–1.95 (m, 4H), 2.94 and 3.01 (2 s, together 3H), 3.35–3.55 (rm, 2H), 3.95–4.10 (m, 2H), 4.27–4.46 (m, 1H).

Example 5

N-Propyl-N-(tetrahydrofuran-3-yl)-4,5-dihydro-4-(2-fluorophenyl)-1H-tetrazol-5-one-1-carboxamide (No. Ib.12)

1.4 g (7.8 mmol) of 1,2-dihydro-1-(2-fluorophenyl)-5H-tetrazol-5-one, 1.5 g (7.8 mmol) of N-propyl-N-(tetrahydro-furan-3-yl)carbamoyl chloride and 1.29 g (10 mmol) of 4-dimethylaminopyridine were reacted by the method of the process described in Example 1. Yield 2.1 g.

Intermediate 5.1

N-(Tetrahydrofuran-3-yl)propionamide

A solution of 50 g of 3-aminotetrahydrofuran in 200 ml of dichloromethane was mixed with 63.8 g (0.63 mol) of triethylamine. 58.4 g (0.63 mol) of propionyl chloride were added dropwise with ice-cooling. The mixture was stirred at room temperature for 2 days, resulting in a white precipitate. The solution was filtered and the filtrate was distilled. B.p. 145° C. (12 mm), yield 81 g. $^1$H NMR (270 MHz, in CDCl$_3$): δ=1.14 (t, 3 H), 1.83 (m, 1H), 2.22 (q, 2H), 2.31 (m, 1H), 3.64 (dd, 1H), 3.72–3.98 (m, 3H), 4.50 (m, 1H), 6.57 (s, 1H).

Intermediate 5.2

N-Propyl-N-(tetrahydrofuran-3-yl)amine

A suspension of 21.7 g (0.57 mol) of lithium aluminum hydride in 500 ml of THF was admixed dropwise with a solution of 81 g (0.57 mol) of N-(tetrahydrofuran-3-yl) propionamide, and the solution was heated at reflux for 2 h. Excess lithium aluminum hydride was hydrolyzed by dropwise addition of 16 ml of water, 50 ml of 10% strength aqueous sodium hydroxide solution and another 45 ml of water. The white suspension was heated at reflux for one hour, causing the insoluble components to aggregate to a coarse white precipitate. The mixture was filtered off from the precipitate, the precipitate was thoroughly rinsed with ether and the combined filtrates were distilled. B.p. 64° C. (12 mm), yield 41 g. $^1$H NMR (270 MHz, in CDCl$_3$): δ=0.92 (t, 3H), 1.15 (s, 1H), 1.50 (sext., 2H), 1.70 (m, 1H), 2.10 (m, 1H), 2.55 (m, 2H), 3.38 (m, 1H), 3.56 (dd, 1H), 3.70–3.96 (m, 3H).

Intermediate 5.3

N-Propyl-N-(tetrahydrofuran-3-yl)carbamoyl chloride (No. III.3)

94 g (0.95 mol) of phosgene, 41 g (0.32 mol) of N-propyl-N-(tetrahydrofuran-3-yl)amine and 32 g (0.32 mol) of triethylamine were reacted by the method of the process described in Intermediate 1.2. Yield 54 g. $^1$H NMR (270 MHz, in CDCl$_3$): δ=0.92 (t, 3H), 1.70 (sext., 2H), 2.02 (s, 1H), 2.30 (s, 1H), 3.20–3.40 (m, 2H), 3.65–3.85 (m, 3H), 4.05 (m, 1H), 4.50–4.70 and 4.85–5.05 (2 m, together 1H).

The intermediates of the formula V mentioned below were prepared by the methods of the processes described in Intermediates 1.1, 2.1 and 4.1.

n-Propyl(tetrahydro-2H-pyran-4-yl)amine: B.p. 90° C. (12 mm). $^1$H NMR (270 MHz, in CDCl$_3$): δ=0.93 (t, 3H), 1.30–1.60 (m, 5H), 1.83 (dd, 2H), 2.63 (t, 2H), 2.68 (tt, 1H), 3.40 (dt, 2H), 3.99 (dt, 2H).

i-Propyl(tetrahydro-2H-pyran-4-yl)amine: B.p. 104° C. $^1$H NMR (360 MHz, in CDCl$_3$): δ=0.72 (s, 1H), 1.07 (d, 6H), 1.36 (dq, 2H), 1.84 (d, 2H), 2.75 (tt, 1H), 3.00 (sept., 1H), 3.41 (t, 2H), 3.97 (d, 2H).

n-Propyl(tetrahydrothiophen-3-yl)amine: B.p. 104–108° C. (12 mm). $^1$H NMR (270 MHz, in CDCl$_3$): δ=0.94 (t, 3H), 1.26 (s, 1H), 1.51 (sext., 2H), 1.83–2.10 (m, 2H), 2.55–2.70 (m, 3H), 2.87 (t, 2H), 2.96 (dd, 1H), 3.44 (quint., 1H).

Ethyl(tetrahydro-2H-thiopyran-4-yl)amine: B.p. 100° C. (12 mm). $^1$H NMR (270 MHz, in CDCl$_3$): δ=0.96 (s, 1H), 1.11 (t, 3H), 1.40–1.60 (m, 2H), 2.17 (dq, 2H), 2.47 (tt, 1H), 2.60–2.75 (m, 6H).

n-Propyl(tetrahydro-2H-thiopyran-4-yl)amine: B.p. 115° C. (12 mm). $^1$H NMR (270 MHz, in CDCl$_3$): δ=0.93 (t, 3H), 1.05 (s, 1H), 1.40–1.60 (m, 4H), 2.18 (dq, 2H), 2.45 (tt, 1H), 2.60 (t, 2H), 2.62–2.75 (m, 4H).

The intermediates of the formula III mentioned below were prepared by the methods of the processes described in Intermediates 1.2, 2.2, 3.2, 4.2 and 5.3.

N-n-Propyl-N-(tetrahydro-2H-pyran-4-yl)carbamoyl chloride (No. III. 12): $^1$H NMR (270 MHz, in CDCl$_3$): δ=0.93 (t, 3H), 1.55–2.00 (m, 6H), 3.15–3.50 (m, 4H), 3.95–4.10 (m, 2H), 4.10–4.40 (m, 1H).

N-i-Propyl-N-(tetrahydro-2H-pyran-4-yl)carbamoyl chloride (No. III. 13): $^1$H NMR (270 MHz, in CDCl$_3$): δ=1.24 (d, 3H), 1.38 (d, 3H), 1.65–1.95 (m, 4H), 3.30–3.50 (m, 2H), 3.62 (sept., 1H), 3.98–4.12 (m, 2H), 4.25–4.47 (m, 1H).

N-n-Propyl-N-(tetrahydrothiophen-3-yl)carbamoyl chloride (No. III.21): $^1$H NMR (250 MHz, in CDCl$_3$): δ=0.92 (t, 3H), 1.50–1.70 (m, 2H), 2.16 (q, 2H), 2.85–3.05 (m, 2H), 3.47–3.75 (m, 4H), 4.00–4.10 (m, 1H).

N-Ethyl-N-(tetrahydro-2H-thiopyran-4-yl)carbamoyl chloride (No. III.29): $^1$H NMR (250 MHz, in CDCl$_3$): δ=1.15–1.30 (m, 3H), 1.80–2.20 (m, 4H), 2.60–2.86 (m, 4H), 3.30–3.50 (m, 2H), 3.90–4.20 (m, 1H).

N-n-Propyl-N-(tetrahydro-2H-thiopyran-4-yl)carbamoyl chloride (No. III.30): $^1$H NMR (270 MHz, in CDCl$_3$): δ=0.91 (t, 3H), 1.55–2.20 (m, 6H), 2.60–2.90 (m, 4H), 3.15–3.35 (m, 2H), 3.85–4.15 (m, 1H).

In the Tables 4 and 5 below, the physical data of the compounds of the formula I listed above are compiled, and compounds of the formula I are listed which were prepared in a similar manner:

TABLE 4

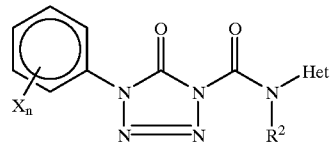

I

| No. | $X_n$ | $R^2$ | Het | $^1$H NMR [ppm]/ MS [m/z] |
|---|---|---|---|---|
| Ia.1 | H | CH$_3$ | tetrahydro-2H-pyran-4-yl | 1.75–2.00(m, 4H), 3.04(s, 3H), 3.30–3.60(m, 2H), 3.70–3.95 and 4.35–4.55(2H, together 1H), 3.97–4.15 (m, 2H), 7.35–7.55 (m, 3H), 7.91(d, 2H) |
| Ia.2 | H | C$_2$H$_5$ | tetrahydro-2H-pyran-4-yl | 1.20–1.40(m, 3H), 1.80–2.10(m, 4H), 3.30–3.60(m, 4H), 3.70–4.40(m, 3H), 7.35–7.58(m, 3H), 7.92(d, 2H) |
| Ia.3 | H | n-C$_3$H$_7$ | tetrahydro-2H-pyran-4-yl | 0.80–1.05(m, 3H), 1.55–2.10(m, 6H), 3.25–3.55(m, 4H), 3.70–4.40(m, 3H), 7.35–7.58(m, 3H), 7.93(d, 2H) |
| Ia.4 | H | i-C$_3$H$_7$ | tetrahydro-2H-pyran-4-yl | 1.45(d, 6H), 1.65–2.40 (m, 4H), 3.40(t, 2H), 3.50–3.70(m, 1H), 3.72–3.95(m, 1H), 4.00–4.10(m, 2H), 7.41(t, 1H), 7.51 (t, 2H), 7.91(d, 2H) |
| Ia.10 | 2-F | CH$_3$ | tetrahydro-2H-pyran-4-yl | 1.80–2.00(m, 4H), 3.05(s, 3H), 3.35–3.60(m, 2H), 3.75–3.90 and 4.40–4.55(2m, together, 1H), 4.00–4.15(m, 2H), 7.28–7.38(m, 2H), 7.50–7.60(m, 2H) |

TABLE 4-continued

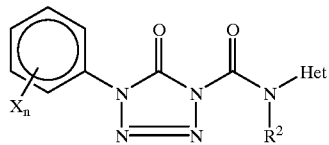

I

| No. | $X_n$ | $R^2$ | Het | $^1$H NMR [ppm]/ MS [m/z] |
|---|---|---|---|---|
| Ia.11 | 2-F | $C_2H_5$ | tetrahydro-2H-pyran-4-yl | 1.20–1.40(m, 3H), 1.80–2.10(m, 4H), 3.30–3.60(m, 4H), 3.70–4.40(m, 3H), 7.20–7.40(m, 2H), 7.45–7.60(m, 2H) |
| Ia.12 | 2-F | n-$C_3H_7$ | tetrahydro-2H-pyran-4-yl | 0.80–1.03(m, 3H), 1.55–2.05(m, 6H), 3.30–3.55(m, 4H), 3.70–4.40(m, 3H), 7.25–7.38(m, 2H), 7.47–7.62(m, 2H) |
| Ia.13 | 2-F | i-$C_3H_7$ | tetrahydro-2H-pyran-4-yl | 1.46(d, 6H), 1.65–2.30 (m, 4H), 3.41(t, 2H), 3.50–3.70(m, 1H), 3.71–3.96(m, 1H), 4.00–4.13(m, 2H), 7.25–7.38(m, 2H), 7.46–7.60(m, 2H), |
| Ia.19 | 2-Cl | $CH_3$ | tetrahydro-2H-pyran-4-yl | 1.75–2.05(m, 4H), 3.06(s, 3H), 3.30–3.60(m, 2H), 3.70–3.90 and 4.40–4.68(2m, together, 1H), 4.00–4.15(m, 2H), 7.40–7.65(m, 4H) |
| Ia.20 | 2-Cl | $C_2H_5$ | tetrahydro-2H-pyran-4-yl | 352 [M+H]$^+$ |
| Ia.21 | 2-Cl | n-$C_3H_7$ | tetrahydro-2H-pyran-4-yl | 0.80–1.00(m, 3H), 1.55–2.05(m, 6H), 3.25–3.55(m, 4H), 3.70–4.45(m, 3H), 7.40–7.65(m, 4H) |
| Ia.22 | 2-Cl | i-$C_3H_7$ | tetrahydro-2H-pyran-4-yl | 1.47(d, 6H), 1.60–2.30 (m, 4H), 3.39(t, 2H), 3.50–3.70(m, 1H), 3.70–3.95(m, 1H), 4.00–4.13(m, 2H), 7.42–7.66(m, 4H) |
| Ia.28 | 2-Br | $CH_3$ | tetrahydro-2H-pyran-4-yl | 1.80–2.00(m, 4H), 3.05(s, 3H), 3.30–3.60(m, 2H), 3.75–3.90 and 4.40–4.55(2m, together 1H), 4.00–4.15(m, 2H), 7.40–7.55(m, 3H), 7.78(d, 1H) |
| Ia.29 | 2-Br | $C_2H_5$ | tetrahydro-2H-pyran-4-yl | 1.20–1.40(m, 3H), 1.80–2.10(m, 4H), 3.30–3.60(m, 4H), 3.70–4.50(m, 3H), 7.40–7.55(m, 3H), 7.79(d, 1H) |
| Ia.30 | 2-Br | n-$C_3H_7$ | tetrahydro-2H-pyran-4-yl | 0.80–1.05(m, 3H), 1.60–2.10(m, 6H), 3.30–3.55(m, 4H), 3.75–4.45(m, 3H), 7.40–7.55(m, 3H), 7.78(d, 1H) |
| Ia.31 | 2-Br | i-$C_3H_7$ | tetrahydro-2H-pyran-4-yl | 1.47(d, 6H), 1.65–2.40 (m, 4H), 3.39(t, 2H), 3.50–3.70(m, 1H), 3.72–3.95(m, 1H), 4.00–4.12(m, 2H), 7.38–7.55(m, 3H), 7.78(d, 1H) |
| Ia.37 | 2-$CH_3$ | $CH_3$ | tetrahydro-2H-pyran-4-yl | 1.75–2.00(m, 4H), 2.31(s, 3H), 3.04 (s, 3H), 3.30–3.60 (m, 2H), 3.70–3.90 and 4.40–4.55(2m, together 1H), 4.00–4.12(m, 2H), 7.30–7.47(m, 4H) |
| Ia.38 | 2-$CH_3$ | $C_2H_5$ | tetrahydro-2H-pyran-4-yl | 1.20–1.40(m, 3H), 1.80–2.10(m, 4H), 2.31(s, 3H), 3.30–3.55(m, 4H), 3.75–4.45(m, 3H), 7.30–7.46(m, 4H) |
| Ia.39 | 2-$CH_3$ | $C_3H_7$ | tetrahydro-2H-pyran-4-yl | 0.80–1.00(m, 3H), 1.55–2.05(m, 6H), 2.31(s, 3H), 3.30–3.60(m, 4H), 3.73–4.45(m, 3H), 7.30–7.48(m, 4H) |
| Ia.40 | 2-$CH_3$ | i-$C_3H_7$ | tetrahydro-2H-pyran-4-yl | 1.46(d, 6H), 1.70–2.40(m, 4H), 2.32(s, 3H), 3.39 (t, 2H), 3.50–3.70 (m, 1H), 3.72–3.95 (m, 1H), 4.00–4.10 (m, 2H), 7.30–7.45 (m, 4H) |
| Ia.155 | 2,6-$Cl_2$ | $C_2H_5$ | tetrahydro-2H-pyran-4-yl | 1.20–1.40(m, 3H), 1.80–2.00(m, 4H), 3.25–3.60(m, 4H), 3.70–4.50(m, 3H), 7.45–7.55(m, 3H) |
| Ia.156 | 2,6-$Cl_2$ | n-$C_3H_7$ | tetrahydro-2H-pyran-4-yl | 0.80–1.05(m, 3H), 1.50–2.05(m, 6H), 3.25–3.55(m, 4H), 3.70–4.50(m, 3H), 7.43–7.57(m, 3H) |
| Ia.157 | 2,6-$Cl_2$ | i-$C_3H_7$ | tetrahydro-2H-pyran-4-yl | 1.47(d, 6H), 1.65–2.40 (m, 4H), 3.36(t, 2H), 3.50–3.67(m, 1H), 3.70–3.90(m, 1H), 4.00–4.12(m, 2H), 7.25–7.45(m, 3H) |
| Ia.199 | 2-Cl, 6-$CH_3$ | $CH_3$ | tetrahydro-2H-pyran-4-yl | 1.70–2.00(m, 4H), 2.28(s, 3H), 3.02(s, 3H), 3.25–3.60(m, 2H), 3.70–3.85 and 4.35–4.55(2m, together 1H), 3.95–4.15(m, 2H), 7.24–7.44(m, 3H) |
| Ia.200 | 2-Cl, 6-$CH_3$ | $C_2H_5$ | tetrahydro-2H-pyran-4-yl | 1.20–1.40(m, 3H), 1.75–2.00(m, 4H), 2.29(s, 3H), 3.30–3.60(m, 4H), 3.65–4.50(m, 3H), 7.22–7.45(m, 3H) |
| Ia.201 | 2-Cl, 6-$CH_3$ | n-$C_3H_7$ | tetrahydro-2H-pyran-4-yl | 0.80–1.05(m, 3H), 1.55–2.05(m, 6H), 2.29(s, 3H), 3.25–3.60(m, 4H), 3.70–4.50(m, 3H), |

TABLE 4-continued

I

[Structure: phenyl-X_n attached to tetrazolinone-C(=O)-N(R²)(Het)]

| No. | $X_n$ | $R^2$ | Het | $^1$H NMR [ppm]/MS [m/z] |
|---|---|---|---|---|
| Ia.202 | 2-Cl, 6-Cl$_3$ | i-C$_3$H$_7$ | tetrahydro-2H-pyran-4-yl | 7.28–7.45(m, 3H) 1.48(s, 6H), 1.70–2.30 (m, 4H), 2.29(s, 3H), 3.30–3.45(m, 2H), 3.50–3.67(m, 1H), 3.70–3.90(m, 1H), 4.00–4.12(m, 2H), 7.25–7.45(m, 3H) |
| Ia.226 | 3-Cl, 4-i-C$_3$H$_7$ | CH$_3$ | tetrahydro-2H-pyran-4-yl | 1.28(d, 6H), 1.78–2.04 (m, 4H), 3.04(s, 3H), 3.33–3.60(m, 2H), 3.44(sept., 1H) 3.70–4.55(m, 3H), 7.43(d, 1H), 7.80 (dd, 1H), 7.94(d, 1H) |
| Ia.227 | 3-Cl, 4-i-C$_3$H$_7$ | C$_2$H$_5$ | tetrahydro-2H-pyran-4-yl | 1.20–1.40(m, 3H), 1.28(d, 6H), 1.80–2.05(m, 4H), 3.35–3.55(m, 5H), 3.70–4.50(m, 3H), 7.43(d, 1H), 7.81 (dd, 1H), 7.96(d, 1H) |
| Ia.228 | 3-Cl, 4-i-C$_3$H$_7$ | n-C$_3$H$_7$ | tetrahydro-2H-pyran-4-yl | 0.80–1.00(m, 3H), 1.28(d, 6H), 1.60–2.10(m, 6H), 3.28–3.53(m, 4H), 3.45(sept., 1H), 3.70–4.45 (m, 3H), 7.43(d, 1H), 7.81(dd, 1H), 7.95 (d, 1H) |
| Ia.229 | 3-Cl, 4-i-C$_3$H$_7$ | i-C$_3$H$_7$ | tetrahydro-2H-pyran-4-yl | 1.28(d, 6H), 1.45(s, 6H), 1.65–2.30(m, 4H), 3.34–3.40(m, 2H), 3.43(sept., 1H), 3.40–3.68(m, 1H), 3.75–3.90 (m, 1H), 4.00–4.13 (m, 2H), 7.43(d, 1H), 7.80(dd, 1H), 7.94 (d, 1H) |
| Ia.388 | 2-CF$_3$ | CH$_3$ | tetrahydro-2H-pyran-4-yl | 1.75–2.00(m, 4H), 2.95–3.10(m, 3H), 3.25–3.60(m, 2H), 3.60–3.80 and 4.40–4.55(2m, together 1H), 3.97–4.15(m, 2H), 7.57(d, 1H), 7.72 (t, 1H), 7.79(t, 1H), 7.89(d, 1H) |
| Ia.389 | 2-CF$_3$ | C$_2$H$_5$ | tetrahydro-2H-pyran-4-yl | 1.20–1.45(m, 3H), 1.80–2.05(m, 4H), 3.30–3.55(m, 4H), 3.40–4.50(m, 3H), 7.57(d, 1H), 7.72(t, 1H), 7.80 (t, 1H), 7.89(d, 1H) |
| Ia.391 | 2-CF$_3$ | i-C$_3$H$_7$ | tetrahydro-2H-pyran-4-yl | 1.47(d, 6H), 1.70–2.40(m, 4H), 3.38(t, 2H), 3.47–3.66(m, 1H), 3.70–3.90(m, 1H), 3.98–4.11(m, 2H), 7.57(d, 1H), 7.73 (t, 1H), 7.80(t, 1H), 7.89(d, 1H) |
| Ib.3 | H | n-C$_3$H$_7$ | tetrahydrofuran-3-yl | 0.85–1.00(m, 3H), 1.65–1.90(m, 2H), 2.05–2.20(m, 1H), 2.30–2.46(m, 1H), 3.30–3.51(m, 2H), 3.60–4.18(m, 4H), 4.45–4.70(m, 1H), 7.41(t, 1H), 7.52 (t, 2H), 7.91(d, 2H) |
| Ib.12 | 2-F | n-C$_3$H$_7$ | tetrahydrofuran-3-yl | 0.80–1.05(m, 3H), 1.50–1.90(m, 2H), 2.05–2.20(m, 1H), 2.34–2.43(m, 1H), 3.32–3.50(m, 2H), 3.60–4.15(m, 4H), 4.45–4.75(m, 1H), 7.27–7.36(m, 2H), 7.49–7.59(m, 2H) |
| Ib.21 | 2-Cl | n-C$_3$H$_7$ | tetrahydrofuran-3-yl | 0.80–1.02(m, 3H), 1.60–1.90(m, 2H), 2.05–2.20(m, 1H), 2.35–2.45(m, 1H), 3.34–3.50(m, 2H), 3.65–4.17(m, 4H), 4.45–4.90(m, 1H), 7.44–7.55(m, 3H), 7.61(d, 1H) |
| Ib.30 | 2-Br | n-C$_3$H$_7$ | tetrahydrofuran-3-yl | 0.80–1.02(m, 3H), 1.60–1.90(m, 2H), 2.00–2.25(m, 1H), 2.32–2.48(m, 1H), 3.31–3.52(m, 2H), 3.60–4.20(m, 4H), 4.40–4.80(m, 1H), 7.40–7.57(m, 3H), 7.79(d, 1H) |
| Ie.2 | H | C$_2$H$_5$ | tetrahydro-2H-thiopyran-4-yl | 1.13–1.40(m, 3H), 1.85–2.35(m, 4H), 2.60–2.95(m, 4H), 3.35–3.65 and 3.95–4.20(2m, together 3H), 7.92 (d, 2H) |
| Ie.3 | H | n-C$_3$H$_7$ | tetrahydro-2H-thiopyran-4-yl | 0.80–1.05(m, 3H), 1.55–1.85(m, 2H), 1.88–2.17(m, 2H), 2.19–2.35(m, 2H), 2.60–2.95(m, 2H), 3.25–3.45(m, 2H), 3.47–3.64 and 3.97–4.16(2m, together 3H), 7.41 (t, 1H), 7.52(t, 2H), 7.91(d, 2H) |
| Ie.10 | 2-F | CH$_3$ | tetrahydro-2H-thiopyran-4-yl | 1.85–2.05(m, 2H), 2.15–2.30(m, 2H), 2.65–2.97(m, 4H), 3.06(s, 3H), 3.40–3.60 and 4.15–4.30(2m, together 1H), 7.22–7.40(m, 2H), 7.47–7.60(m, 2H) |
| Ie.12 | 2-F | n-C$_3$H$_7$ | tetrahydro-2H- | 0.80–1.03(m, 3H), |

TABLE 4-continued

I

| No. | $X_n$ | $R^2$ | Het | $^1$H NMR [ppm]/ MS [m/z] |
|---|---|---|---|---|
| | | | thiopyran-4-yl | 1.54–1.83(m, 2H), 1.90–2.17(m, 2H), 2.18–2.40(m, 2H), 2.65–2.95(m, 4H), 3.30–3.44(m, 2H), 3.45–3.64 and 3.97–4.18(2m, together 3H), 7.25–7.39(m, 2H), 7.48–7.61(m, 2H) |
| Ie.19 | 2-Cl | $CH_3$ | tetrahydro-2H-thiopyran-4-yl | 1.85–2.10(m, 2H), 2.15–2.30(m, 2H), 2.65–2.95(m, 4H), 3.05(m, 3H), 3.40–3.60 and 4.15–4.30(2m, together 1H), 7.40–7.65(m, 4H) |
| Ie.20 | 2-Cl | $C_2H_5$ | tetrahydro-2H-thiopyran-4-yl | 1.15–1.40(m, 3H), 1.85–2.35(m, 4H), 2.60–2.95(m, 4H), 3.40–3.62 and 4.02–4.22(2m, together 3H), 7.40–7.65(m, 4H) |
| Ie.21 | 2-Cl | n-$C_3H_7$ | tetrahydro-2H-thiopyran-4-yl | 0.80–1.03(m, 3H), 1.55–1.82(m, 2H), 1.88–2.15(m, 2H), 2.20–2.35(m, 2H), 2.65–2.92(m, 4H), 3.30–3.43(m, 2H), 3.45–3.63 and 4.00–4.20(2m, together 3H), 7.43–7.63(m, 4H), |
| Ie.28 | 2-Br | $CH_3$ | tetrahydro-2H-thiopyran-4-yl | 1.90–2.10(m, 2H), 2.15–2.30(m, 2H), 2.65–2.95(m, 4H), 3.05(m, 3H), 3.40–3.60 and 4.15–4.30(2m, together 1H), 7.40–7.55(m, 3H), 7.79(d, 1H) |
| Ie.29 | 2-Br | $C_2H_5$ | tetrahydro-2H-thiopyran-4-yl | 1.15–1.40(m, 3H), 1.85–2.35(m, 4H), 2.60–2.95(m, 4H), 3.40–3.62 and 4.00–4.20(2m, together 3H), 7.35–7.55(m, 3H), 7.77(d, 1H) |
| Ie.30 | 2-Br | n-$C_3H_7$ | tetrahydro-2H-thiopyran-4-yl | 0.80–1.02(m, 3H), 1.55–1.82(m, 2H), 1.88–2.15(m, 2H), 2.17–2.35(m, 2H), 2.60–2.95(m, 4H), 3.30–3.43(m, 2H), 3.45–3.63 and 4.05–4.20(2m, together 3H), 7.40–7.55(m, 3H), 7.79(d, 1H) |
| Ie.38 | 2-$CH_3$ | $C_2H_5$ | tetrahydro-2H-thiopyran-4-yl | 1.15–1.40(m, 3H), 1.90–2.35(m, 4H), 2.30(s, 3H), |
| Ie.155 | 2,6-$Cl_2$ | $C_2H_5$ | tetrahydro-2H-thiopyran-4-yl | 2.60–2.95(m, 4H), 3.43–3.60 and 4.00–4.20(2m, together 3H), 7.30–7.47(m, 3H) 1.15–1.40(m, 3H), 1.90–2.35(m, 4H), 2.55–2.95(m, 4H), 3.40–3.60 and 4.05–4.25(2m, together 3H), 7.43–7.58(m, 3H) |
| Ie.156 | 2,6-$Cl_2$ | n-$C_3H_7$ | tetrahydro-2H-thiopyran-4-yl | 0.80–1.05(m, 3H), 1.50–1.84(m, 2H), 1.87–2.15(m, 2H), 2.17–2.30(m, 2H), 2.60–2.95(m, 4H), 3.25–3.55 and 4.05–4.20(2m, together 3H), 7.42–7.58(m, 3H) |
| Ie.199 | 2-Cl, 6-$CH_3$ | $CH_3$ | tetrahydro-2H-thiopyran-4-yl | 1.90–2.05(m, 2H), 2.15–2.30(m, 2H), 2.27(s, 3H), 2.65–2.95(m, 4H), 3.04(m, 3H), 3.40–3.60 and 4.15–4.30(2m, together 1H), 7.22–7.45(m, 3H) |
| Ie.200 | 2-Cl, 6-$CH_3$ | $C_2H_5$ | tetrahydro-2H-thiopyran-4-yl | 1.15–1.40(m, 3H), 1.85–2.40(m, 4H), 2.29(s, 3H), 2.55–2.95(m, 4H), 3.40–3.65 and 4.05–4.25(2m together 3H), 7.25–7.47(m, 3H) |
| Ie.201 | 2-Cl, 6-$CH_3$ | n-$C_3H_7$ | tetrahydro-2H-thiopyran-4-yl | 0.80–1.05(m, 3H), 1.55–1.85(m, 2H), 1.90–2.15(m, 2H), 2.17–2.40(m, 2H), 2.29(s, 3H), 2.60–2.95(m, 4H), 3.25–3.60 and 4.05–4.20(2m, together 3H), 7.25–7.45(m, 3H) |
| Ie.226 | 3-Cl, 4-i-$C_3H_7$ | $CH_3$ | tetrahydro-2H-thiopyran-4-yl | 1.28(d, 6H), 1.90–2.05(m, 2H), 2.15–2.30(m, 2H), 2.65–2.95(m, 4H), 3.04(m, 3H), 3.44(sept., 1H), 3.50–3.60 and 4.15–4.30(2m, together 1H), 7.43 (d, 1H), 7.79 (dd, 1H), 7.93(d, 1H) |
| Ie.227 | 3-Cl, 4-i-$C_3H_7$ | $C_2H_5$ | tetrahydro-2H-thiopyran-4-yl | 1.15–1.40(m, 3H), 1.28(d, 6H), 1.90–2.25(m, 4H), 2.62–2.95(m, 4H), 3.35–3.60 and 4.00–4.20(2m, together 3H), 3.45 |

TABLE 4-continued

I

| No. | $X_n$ | $R^2$ | Het | $^1$H NMR [ppm]/ MS [m/z] |
|---|---|---|---|---|
| Ie.228 | 3-Cl, 4-i-$C_3H_7$ | n-$C_3H_7$ | tetrahydro-2H-thiopyran-4-yl | 0.80–1.05(m, 3H), 1.28(d, 6H), 1.55–1.80(m, 2H), 1.90–2.15(m, 2H), 2.20–2.35(m, 2H), 2.65–2.90(m, 4H), 3.30–3.60 and 3.95–4.15(2m, together 3H), 3.44 (sept., 1H), 7.43 (d, 1H), 7.81(dd, 1H), 7.96(d, 1H) |
| Ie.388 | 2-$CF_3$ | $CH_3$ | tetrahydro-2H-thiopyran-4-yl | 1.75–2.12(m, 2H), 2.15–2.30(m, 2H), 2.60–2.98(m, 4H), 3.01 and 3.09(2s, together 3H), 3.35–3.60 and 4.15–4.30(2m, together 1H), 7.50–7.95(m, 4H) |
| Ie.389 | 2-$CF_3$ | $C_2H_5$ | tetrahydro-2H-thiopyran-4-yl | 1.10–1.40(m, 3H), 1.80–2.35(m, 4H), 2.55–2.95(m, 4H), 3.30–3.60 and 4.00–4.20(2m, together 3H), 7.58 (d, 1H), 7.72(t, 1H), 7.80(t, 1H), 7.90 (d, 1H) |
| If.228 | 3-Cl, 4-i-$C_3H_7$ | n-$C_3H_7$ | tetrahydrothio-phen-3-yl | 0.85–1.00(m, 3H), 1.28(d, 6H), 1.65–1.80(m, 2H), 2.00–2.45(m, 2H), 2.80–3.10(m, 4H), 3.25–3.45(m, 2H), 3.44(sept., 1H), 4.25–4.50(m, 1H), 7.43(d, 1H), 7.79 (dd, 1H), 7.93(d, 1H) |
| Ih.3 | H | n-$C_3H_7$ | 2,4-dimethyl-thiophen-3-yl | 0.98(t, 3H), 1.60–1.90(m, 2H), 2.17(s, 3H), 2.35 (s, 3H), 3.53(ddd, 1H), 3.81(ddd, 1H), 6.69(s, 1H), 7.35 (t, 1H), 7.46(t, 2H), 7.78(d, 2H) |
| Ih.12 | 2-F | n-$C_3H_7$ | 2,4-dimethyl-thiophen-3-yl | 0.98(t, 3H), 1.60–1.90(m, 2H), 2.17(s, 3H), 2.34 (s, 3H), 3.52(ddd, 1H), 3.82(ddd, 1H), 6.70(s, 1H), 7.17–7.30(m, 2H), 7.35–7.50(m, 2H) |
| Ih.21 | 2-Cl | n-$C_3H_7$ | 2,4-dimethyl-thiophen-3-yl | 0.99(t, 3H), 1.60–1.90(m, 2H), 2.17(s, 3H), 2.34 (s, 3H), 3.52 (ddd, 1H), 3.83 (ddd, 1H), 6.69 (s, 1H), 7.34–7.52 (m, 4H) |
| Ih.30 | 2-Br | n-$C_3H_7$ | 2,4-dimethyl-thiophen-3-yl | 0.98(t, 3H), 1.60–1.90(m, 2H), 2.18(s, 3H), 2.35 (s, 3H), 3.52 (ddd, 1H), 3.84 (ddd, 1H), 6.70 (s, 1H) 7.30–7.47 (m, 3H), 7.67(d, 1H) |
| Ih.39 | 2-$CH_3$ | n-$C_3H_7$ | 2,4-dimethyl-thiophen-3-yl | 0.98(t, 3H), 1.60–1.90(m, 2H), 2.01(s, 3H), 2.17 (s, 3H), 2.35(s, 3H), 3.54(ddd, 1H), 3.82 (ddd, 1H), 6.69 (s, 1H), 7.15–7.40 (m, 4H) |
| Ih.156 | 2,6-$Cl_2$ | n-$C_3H_7$ | 2,4-dimethyl-thiophen-3-yl | 0.98(t, 3H), 1.60–1.90(m, 2H), 2.18(s, 3H), 2.34 (s, 3H), 3.51 (ddd, 1H), 3.85 (ddd, 1H), 6.67 (s, 1H), 7.35–7.45 (m, 3H) |
| Ih.201 | 2-Cl, 6-$CH_3$ | n-$C_3H_7$ | 2,4-dimethyl-thiophen-3-yl | 0.98(t, 3H), 1.60–1.90(m, 2H), 2.08(s, 3H), 2.18 (s, 3H), 2.35(s, 3H), 3.52(ddd, 1H), 3.83 (ddd, 1H), 6.68 (s, 1H), 7.12–7.35 (m, 3H) |
| Ih.228 | 3-Cl, 4-i-$C_3H_7$ | n-$C_3H_7$ | 2,4-dimethyl-thiophen-3-yl | 0.98(t, 3H), 1.24 (d, 6H), 1.60–1.87 (m, 2H), 2.16(s, 3H), 2.34(s, 3H), 3.40 (sept., 1H), 3.53 (ddd, 1H), 3.81(ddd, 1H), 6.69(s, 1H), 7.37(d, 1H), 7.68 (dd, 1H), 7.80(d, 1H) |
| Ih.390 | 2-$CF_3$ | n-$C_3H_7$ | 2,4-dimethyl-thiophen-3-yl | 0.98(t, 3H), 1.60–1.90(m, 2H), 2.15(s, 3H), 2.33 (s, 3H), 3.52 (ddd, 1H), 3.82 (ddd, 1H), 6.70 (s, 1H), 7.39(d, 1H), 7.64(t, 1H), 7.70 (t, 1H), 7.80(d, 1H) |

TABLE 5

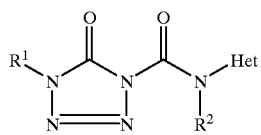

| No. | R¹ | R² | Het | $^1$H NMR [ppm]/ MS [m/z] |
|---|---|---|---|---|
| Ii.47 | CH$_2$—CH$_2$—Cl | C$_2$H$_5$ | tetrahydro-2H-pyran-4-yl | 1.13–1.37(m, 3H), 1.80–2.05(m, 4H), 3.30–3.55(m, 4H), 3.64–3.80 and 3.97–4.12(2m, together 3H), 3.90 (t, 2H), 4.32(t, 2H) |
| Ii.48 | CH$_2$—CH$_2$—Cl | n-C$_3$H$_7$ | tetrahydro-2H-pyran-4-yl | 0.75–1.00(m, 3H), 1.50–2.03(m, 6H), 3.22–3.50(m, 4H), 3.62–3.80 and 3.97–4.12(2m, together 3H), 3.90 (t, 2H), 4.32(t, 2H) |
| Ii.49 | CH$_2$—CH$_2$—Cl | i-C$_3$H$_7$ | tetrahydro-2H-pyran-4-yl | 1.44(s, 6H), 1.64–2.40(m, 4H), 3.37(t, 2H), 3.45–3.60(m, 1H), 3.70–3.85(m, 1H), 3.90(t, 2H), 4.00–4.12(m, 2H), 4.32(t, 2H) |
| In.47 | CH$_2$—CH$_2$—Cl | C$_2$H$_5$ | tetrahydro-2H-thiopyran-4-yl | 1.12–1.36(m, 3H), 1.90–2.12(m, 2H), 2.15–2.27(m, 2H), 2.60–2.90(m, 4H), 3.37–3.55 and 4.00–4.15(2m, together 3H), 3.90 (t, 2H), 4.32(t, 2H) |
| In.48 | CH$_2$—CH$_2$—Cl | n-C$_3$H$_7$ | tetrahydro-2H-thiopyran-4-yl | 0.80–1.00(m, 3H), 1.55–1.80(m, 2H), 1.87–2.10(m, 2H), 2.15–2.26(m, 2H), 2.65–2.90(m, 4H), 3.20–3.60 and 3.97–4.15(2m, together 3H), 3.90 (t, 2H), 4.32(t, 2H) |
| Iq. 48 | CH$_2$—CH$_2$—Cl | n-C$_3$H$_7$ | 2,4-dimethyl-thiophen-3-yl | 343 [M]* |

USE EXAMPLES

The herbicidal action of the substituted tetrazolinonecarboxamides of the formula I was demonstrated by greenhouse experiments:

The culture containers used were plastic pots containing loamy sand with approximately 3.0% of humus as substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants, unless this was adversely affected by the active ingredients.

For the post-emergence treatment, the test plants were first grown to a height of 3 to 15 cm, depending on the plant habit, and then treated with the active ingredients which had been suspended or emulsified in water. For this purpose, the test plants were either sown directly and grown in the same containers, or they were first grown separately as seedlings and transplanted into the test containers a few days prior to treatment. The application rate for the post-emergence treatment was 1.0 kg of a.s. (active substance)/ha.

Depending on the species, the plants were kept at 10 to 25° C. or 20 to 35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts, and 0 means no damage, or normal course of growth. Using the compound Ia. 20, for example, damage of 80 to 85% was achieved by the post-emergence method in the plant species listed below:

| Scientific Name | Common Name |
|---|---|
| *Alopecurus myosuroides* | blackgrass |
| *Echinochloa crus-galli* | barnyardgrass |

We claim:
1. A substituted tetrazolinonecarboxamide of the formula I

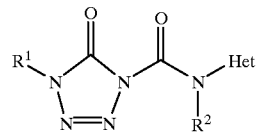

where the variables have the following meaning:
Het is furan-3-yl or thiophen-3-yl,
where the abovementioned heterocycles may carry one or two substituents selected from a group consisting of halogen, C$_1$–C$_6$-alkyl and C$_1$–C$_6$-haloalkyl;
R¹ is C$_1$–C$_6$-alkyl, C$_1$–C$_6$-haloalkyl, cyano-C$_1$–C$_4$-alkyl, C$_1$–C$_4$-alkoxy-C$_1$–C$_4$-alkyl, C$_1$–C$_4$-haloalkoxy-C$_1$–C$_4$-alkyl, C$_1$–C$_4$-alkylthio-C$_1$–C$_4$-alkyl, C$_1$–C$_4$-haloalkylthio-C$_1$–C$_4$-alkyl, C$_1$–C$_4$-alkylsulfonyl-C$_1$–C$_4$-alkyl, C$_1$–C$_4$-haloalkylsulfonyl-C$_1$–C$_4$-alkyl, C$_2$–C$_6$-alkenyl, cyano-C$_3$–C$_6$-alkenyl, C$_2$–C$_6$-haloalkenyl, C$_3$–C$_6$-alkynyl, C$_3$–C$_8$-cycloalkyl, C$_3$–C$_8$-cycloalkyl-C$_1$–C$_4$-alkyl, C$_5$–C$_8$-cycloalkenyl, C$_5$–C$_8$-cycloalkenyl-C$_1$–C$_4$-alkyl, phenyl, phenyl-C$_1$–C$_4$-alkyl, 3- to 7-membered heterocyclyl, which may contain a carbonyl or thiocarbonyl ring member, or 3- to 7-membered heterocyclyl-C$_1$–C$_4$-alkyl, which may contain a carbonyl or thiocarbonyl ring member, where the cycloalkyl rings, cycloalkenyl rings, phenyl rings or heterocyclyl rings may in each case be unsubstituted or carry one to four substituents, in each case selected from the group consisting of halogen, cyano, nitro, C$_1$–C$_4$-alkyl, C$_2$–C$_6$-alkenyl, C$_2$–C$_6$-alkynyl, C$_1$–C$_4$-haloalkyl, C$_1$–C$_4$-alkoxy, C$_1$–C$_4$-haloalkoxy, C$_3$–C$_6$-alkenyloxy, C$_3$–C$_6$-alkynyloxy, C$_1$–C$_4$-alkoxycarbonyl-C$_1$–C$_4$-alkoxy, C$_1$–C$_4$-alkylthio, C$_1$–C$_4$-haloalkylthio, C$_1$–C$_4$-alkylsulfonyl, C$_1$–C$_4$-haloalkylsulfonyl, C$_1$–C$_4$-alkoxycarbonyl, C$_1$–C$_4$-alkylcarbonyl, C$_1$–C$_4$-haloalkylcarbonyl, C$_1$–C$_4$-alkylcarbonyloxy and C$_1$–C$_4$-haloalkylcarbonyloxy, and where the heterocyclyl rings are in each case saturated, partially saturated or completely unsaturated and aromatic and contain one to three heteroatoms selected from a group consisting of one to three nitrogen atoms, one or two oxygen atoms and one or two sulfur atoms, $R^2$ is hydrogen, $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl, which may contain a carbonyl or thiocarbonyl ring member, or 3- to 7-membered heterocyclyl-$C_1$–$C_4$-alkyl, which may contain a carbonyl or thiocarbonyl ring member, where the cycloalkyl rings, phenyl rings or heterocyclyl rings are in each case unsubstituted or carry one to four substituents, in each case selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, $C_1$–$C_4$-alkoxycarbonyl, $C_1$–$C_4$-alkylcarbonyl, $C_1$–$C_4$-haloalkylcarbonyl, $C_1$–$C_4$-alkylcarbonyloxy and $C_1$–$C_4$-haloalkylcarbonyloxy, and where the heterocyclyl rings are in each case saturated, partially saturated or completely unsaturated and aromatic and contain one to three heteroatoms selected from a group consisting of one to three nitrogen atoms, one or two oxygen atoms and one or two sulfur atoms.

2. A process for preparing substituted tetrazolinonecarboxamides of the formula I as claimed in claim 1, which comprises reacting a tetrazolinone of the formula II

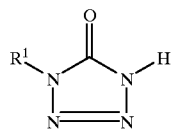

in the presence of a base with a carbamoyl chloride of the formula III

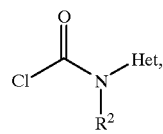

or initially deprotonating a tetrazolinone of the formula II with a base and subsequently reacting it with a carbamoyl chloride of the formula III.

3. A process for preparing substituted tetrazolinonecarboxamides of the formula I as claimed in claim 1, which comprises reacting a tetrazolinonecarbonyl chloride of the formula VI

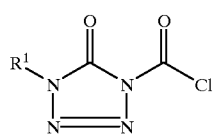

in the presence of a base with an amine of the formula V

4. A carbamoyl chloride of the formula III

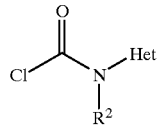

wherein

Het is furan-3-yl or thiophen-3-yl, where the abovementioned heterocycles may carry one or two substituents selected from a group consisting of halogen, $C_1$–$C_6$-alkyl and $C_1$–$C_6$-haloalkyl;

$R^2$ is $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl, which may contain a carbonyl or thiocarbonyl ring member, or 3- to 7-membered heterocyclyl-$C_1$–$C_4$-alkyl, which may contain a carbonyl or thiocarbonyl ring member, where the cycloalkyl rings, phenyl rings or heterocyclyl rings are in each case unsubstituted or carry one to four substituents, in each case selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, $C_1$–$C_4$-alkoxycarbonyl, $C_1$–$C_4$-alkylcarbonyl, $C_1$–$C_4$-haloalkylcarbonyl, $C_1$–$C_4$-alklcarbonyloxy and $C_1$–$C_4$-haloalkylcarbonyloxy, and where the heterocyclyl rings are in each case saturated, partically saturated or completely unsaturated and aromatic and contain one to three heteroatoms selected from a group consisting of one to three nitrogen atoms, one or two oxygen atoms and one or two sulfur atoms.

5. A process for preparing the carbamoyl chloride of formula III defined in claim 4, which comprises reacting an amine of formula V $R^2$—NH—Het  (V)

or an acid addition salt of the amine with a phosgenating agent selected from the group of phosqene, disphosgene and triphosgene.

6. A herbicidal composition which comprises a herbicidally effective amount of at least one substituted triazolinonecarboxamide of the formula I as claimed in claim 1, and at least one customary additive.

7. A process for preparing herbicidally active compositions, which comprises mixing a herbicidally effective amount of at least one substituted tetrazolinone carboxamide of the formula I as claimed in claim 1 with at least one customary additive.

8. A method for controlling undesirable vegetation, which comprises allowing a herbicidally effective amount of at least one substituted tetrazolinone carboxamide of the formula I as claimed in claim 1 to act on plants, their habitat or on seed.

9. The tetrazolinonecarboxamide of formula I defined in claim 1, wherein $R^1$ is $C_1$–$C_6$-alkyl, $C_1$–$C_6$-haloalkyl, cyano-$C_1$–$C_4$-alkyl, $C_1$–$C_4$-alkoxy-$C_1$–$C_4$-alkyl, $C_1$–$C_4$-haloalkoxyl-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_1$–$C_4$-alkylsulfonyl-$C_1$14 $C_4$-alkyl, $C_1$–$C_4$-haloalkylsulfonyl-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, $C_3$–$C_8$-cycloalkyl, $C_3$–$C_8$-cycloalkyl- $C_1$–$C_4$-alkyl, $C_5$–$C_8$-cycloalkenyl, $C_5$–$C_8$-cycloalkenyl-$C_1$–$C_4$-alkyl, phenyl, phenyl-$C_1$–$C_4$-alkyl, 3- to 7-membered heterocyclyl which may contain a carbonyl or thiocarbonyl ring member, or 3- to 7- membered heterocyclyl-$C_1$–$C_4$-alkyl which may contain a carbonyl or thiocarbonyl ring member, where the cycloalkyl rings, cycloalkenyl rings, phenyl rings and heterocyclyl rings are in each case unsubstituted or carry one to four substituents selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, $C_1$–$C_4$-alkoxycarbonyl, $C_1$–$C_4$-alkylcarbonyl, $C_1$–$C_4$-haloalkylcarbonyl, $C_1$–$C_4$-alkylcarbonyloxy and $C_1$–$C_4$-haloalkylcarbonyloxy.

10. The tetrazolinonecarboxamide of formula I defined in claim 1, wherein $R^1$ is $C_1$–$C_6$-alkyl, $C_1$–$C_6$-haloalkyl, cyano-$C_1$–$C_4$-alkyl, $C_3$–$C_6$-alkenyl, $C_3$–$C_6$-haloalkenyl, $C_3$–$C_6$-alkynyl, $C_3$–$C_8$-cycloalkyl, $C_3$–$C_8$-cycloalkyl-$C_1$–$C_4$-alkyl, $C_5$–$C_8$-cycloalkenyl, $C_5$–$C_8$-cycloalkenyl-$C_1$–$C_4$-alkyl, phenyl, phenyl-$C_1$–$C_4$-alkyl, 3- to 7-membered heterocyclyl which may contain a carbonyl or thiocarbonyl ring member, or 3- to 7-membered heterocyclyl-$C_1$–$C_4$-alkyl which may contain a carbonyl or thiocarbonyl ring member, where the cycloalkyl rings, cycloalkenyl rings, phenyl rings and heterocyclyl rings are in each case unsubstituted or carry one to four substituents selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl and $C_1$–$C_4$-alkylcarbonyl.

11. The tetrazolinonecarboxamide of formula I defined in claim 1, wherein $R^1$ is $C_1$–$C_6$-alkyl, $C_1$–$C_6$-haloalkyl, $C_2$–$C_6$-alkenyl, $C_2$–$C_6$-haloalkenyl, $C_3$–$C_8$-cycloalkyl, $C_5$–$C_8$-cycloalkenyl, phenyl, phenyl-$C_1$–$C_4$-alkyl or 3- to 7-membered heterocyclyl which may contain a carbonyl or thiocarbonyl ring member, where the cycloalkyl rings, cycloalkenyl rings, phenyl rings and heterocyclyl rings are in each case unsubstituted or carry one to four substituents selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl and $C_1$–$C_4$-alkylcarbonyl.

12. The tetrazolinonecarboxamide of formula I defined in claim 1, wherein $R^1$ is $C_1$–$C_6$-alkyl, $C_1$–$C_6$-haloalkyl, $C_3$–$C_8$-cycloalkyl, $C_5$–$C_8$-cycloalkenyl, phenyl or $C_3$–$C_7$-membered heterocyclyl which may contain a carbonyl or thiocarbonyl ring member, where the cycloalkyl rings, cycloalkenyl rings, phenyl rings and heterocyclyl rings are in each case be unsubstituted or carry one to four substituents selected from the group consisting of halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl and $C_1$–$C_4$-alkylcarbonyl.

13. The tetrazolinonecarboxamide of formula I defined in claim 1, wherein $R^1$ is phenyl which is unsubstituted or carries one to four substituents selected from the group consisting of halogen, cyano, nitro, $C_1$–$C_4$-alkyl, $C_1$–$C_4$-halo-alkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl and $C_1$–$C_4$-alkylcarbonyl.

14. The tetrazolinonecarboxamide of formula I defined in claim 1, wherein $R^2$ is hydrogen, $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, phenyl or benzyl.

15. The tetrazolinonecarboxamide of formula I defined in claim 1, wherein $R^2$ is $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, phenyl or benzyl.

\* \* \* \* \*

UNITED STATES PATENT AND TRADEMARK OFFICE
CERTIFICATE OF CORRECTION

PATENT NO.    : 6,277,790 B1
DATED         : August 21, 2001
INVENTOR(S)   : Zagar et al.

It is certified that error appears in the above-identified patent and that said Letters Patent is hereby corrected as shown below:

Column 56, claim 4,
Line 33, "partically" should be -- partially --.

Column 56, claim 5,
Line 44, "phosqene" should be -- phosgene --.

Column 56, claim 9,
Line 64, "$C_1 4C_4$-alkyl" should be -- $C_1$-$C_4$-alkyl --.

Signed and Sealed this

Twenty-sixth Day of February, 2002

Attest:

JAMES E. ROGAN
Attesting Officer    Director of the United States Patent and Trademark Office